(12) United States Patent
Mak et al.

(10) Patent No.: US 9,493,561 B2
(45) Date of Patent: Nov. 15, 2016

(54) ANTIBODIES TO TOSO

(71) Applicant: University Health Network, Toronto (CA)

(72) Inventors: Tak W. Mak, Toronto (CA); Xiuqiu Lai, Toronto (CA); Michael W. Tusche, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 14/322,551

(22) Filed: Jul. 2, 2014

(65) Prior Publication Data

US 2015/0010542 A1 Jan. 8, 2015

Related U.S. Application Data

(60) Provisional application No. 61/842,766, filed on Jul. 3, 2013.

(51) Int. Cl.
*C07K 16/00* (2006.01)
*C07K 16/28* (2006.01)

(52) U.S. Cl.
CPC ..... *C07K 16/2803* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 6,683,168 B1 | 1/2004 | Rothstein et al. | |
| 6,727,350 B2 | 4/2004 | Nolan et al. | |
| 6,855,495 B1 | 2/2005 | Payan | |
| 7,645,449 B2 | 1/2010 | Stassi et al. | |
| 2008/0295190 A1 | 11/2008 | Wong et al. | |
| 2010/0099742 A1 | 4/2010 | Stassi et al. | |
| 2012/0148581 A1 | 6/2012 | Xiong et al. | |
| 2013/0281356 A1 | 10/2013 | Tusche et al. | |

FOREIGN PATENT DOCUMENTS

| WO | WO 2008/154351 A1 | 12/2008 |
|---|---|---|
| WO | WO 2013/136193 A2 | 9/2013 |

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
Colman P. M., Research in Immunology, 145:33-36, 1994.*
MacCallum et al, J. Mol. Biol., 262, 732-745, 1996.*
Pascalis et al, Journal of Immunology, 2002, vol. 169, pp. 3076-3084.*
Casset et al, Biochemical and Biophysical Research Communications, 2003, vol. 307, pp. 198-205.*
Bellone, M. et al., "Ways to enhance lymphocyte trafficking into tumors and fitness of tumor infiltrating lymphocytes," *Frontiers in Oncology*, Sep. 11, 2013, vol. 3, Article 231, pp. 1-15.
Brenner, D. et al., "Toso controls encephalitogenic immune responses by dendritic cells and regulatory T cells," *PNAS*, Jan. 11, 2014, vol. 111, No. 3, pp. 1060-1065.
Burkholder, B. et al., "Tumor-induced perturbations of cytokines and immune cell networks," *Biochimica et Biophysica Acta*, 2014, vol. 1845, pp. 182-201.
Callahan, M.K. et al., "At the Bedside: CTLA-4- and PD-1-blocking antibodies in cancer immunotherapy," *Journal of Leukocyte Biology*, Jul. 2013, vol. 94, pp. 41-53.
Fan, C-W., et al, "Blockade of phospholipid scramblase 1 with its N-terminal domain antibody reduces tumorigenesis of colorectal carcinomas in vitro and in vivo," *Journal of Translational Medicine*, 2012, vol. 10, No. 254, pp. 1-13.
Vire, B. et al., "TOSO, the Fcμ Receptor, is Highly Expressed on Chronic Lymphocytic Leukemia B Cells, Internalizes upon IgM Binding, Shuttles to the Lysosome, and is Downregulated in Response to TLR Activation," *The Journal of Immunology*, 2011, vol. 187, pp. 4040-4050.
Walsh, D. et al., "Pattern recognition receptors—Molecular orchestrators of inflammation in inflammatory bowel disease," *Cytokine & Growth Factor Reviews*, 2013, vol. 24, pp. 91-104.
Aggarwal, A. et al., "Gene Expression Profiling Reveals Dysregulation of Innate Immune Genes in Synovial Fluid Mononuclear Cells of Patients With Enthesitis Related Arthritis," *Arthritis & Rheumatism*, Nov. 2011, vol. 63, Abstract Supplement, 1 page.
Dharmadhikari, G. et al., "The Fas apoptotic inhibitory protein TOSO induces proliferation in human beta cells," *Diabetologia*, 2009, vol. 52 (Suppl 1) S1-S550, Abstract No. 199, p. S88.
Dharmadhikari, G. et al., "TOSO promotes β-cell proliferation and protects from apoptosis," *Molecular Metabolism*, 2012, vol. 1, pp. 70-78.
Evan, G.I. et al., "Isolation of Monoclonal Antibodies Specific for Human c-*myc* Proto-Oncogene Product," *Molecular and Cellular Biology*, Dec. 1985, vol. 5, No. 12, pp. 3610-3616.
Field, J. et al., "Purification of a *RAS*-Responsive Adenylyl Cyclase Complex from *Saccharomyces cerevisiae* by Use of n Epitope Addition Method," *Molecular and Cellular Biology*, May 1988, vol. 8, No. 5, pp. 2159-2165.
GenBank Accession No. NM_000632, "*Homo sapiens* integrin, alpha M (complement component 3 receptor 3 subunit) (ITGAM), transcript variant 2 mRNA," Sep. 14, 2013, 7 pages.
GenBank Accession No. NM_001014843, "Rattus norvegicus Fas apoptotic inhibitory molecule 3 (Faim3), mRNA," Sep. 1, 2013, 2 pages.
GenBank Accession No. NM_001142473, "*Homo sapiens* Fas apoptotic inhibitory molecule 3 (FAIM3), transcript variant 3, mRNA," Aug. 19, 2013, 4 pages.
GenBank Accession No. NM_001193338, "*Homo sapiens* Fas apoptotic inhibitory molecule 3 (FAIM3), transcript variant 4, mRNA," Aug. 25, 2013, 4 pages.
GenBank Accession No. NM_005449, "*Homo sapiens* Fas apoptotic inhibitory molecule 3 (FAIM3), transcript variant 1, mRNA," Aug. 19, 2013, 5 pages.
GenBank Accession No. NM_026976, "Mus musculus Fas apoptotic inhibitory molecule 3 (Faim3), mRNA," Aug. 22, 2013, 3 pages.
GenBank Accession No. NP_000623, integrin alpha-M isoform 2 precursor [*Homo sapiens*], Sep. 14, 2013, 4 pages.

(Continued)

*Primary Examiner* — Mark Halvorson

(57) ABSTRACT

The present invention provides methods and compositions for modulating Toso activity and treating diseases and disorders in which Toso is implicated. Such methods and compositions include the use of one or more antibodies that bind to a Toso protein or to a ligand of a Toso protein.

5 Claims, 5 Drawing Sheets

(56) References Cited

OTHER PUBLICATIONS

GenBank Accession No. NP_00104843, fas apoptotic inhibitory molecule 3 precursor [Rattus norvegicus], Sep. 1, 2013, 2 pages.
GenBank Accession No. NP_001135945, "fas apoptotic inhibitory molecule 3 isoform b [Homo sapiens]," Aug. 19, 2013, 3 pages.
GenBank Accession No. NP_001180267, "fas apoptotic inhibitory molecule 3 isoform c precursor [Homo sapiens]," Aug. 25, 2013, 3 pages.
GenBank Accession No. NP_005440, "fas apoptotic inhibitory molecule 3 isoform a precursor [Homo sapiens]," Aug. 19, 2013, 3 pages.
GenBank Accession No. NP_081252, "fas apoptotic inhibitory molecule 3 precursor [Mus musculus]," Aug. 22, 2013, 2 pages.
Hirano, N. et al., "Engagement of CD83 ligand induces prolonged expansion of CD8+ T cells and preferential enrichment for antigen specificity," *Blood*, Feb. 15, 2006, vol. 107, No. 4, pp. 1528-1536.
Hitoshi, Y. et al., "Toso, a Cell Surface, Specific Regulator of Fas-Induced Apoptosis in T Cells," *Immunity*, Apr. 1998, vol. 8, pp. 461-471.
Honjo, K. et al., "Is Toso an antiapoptotic protein or an Fc receptor for IgM?" Blood, Feb. 16, 2012, vol. 119, No. 7, pp. 1789-1790.
Honjo, K. et al., "Is Toso/IgM Fc receptor (FcμR) expressed by innate immune cells," PNAS, Jul. 9, 2013, vol. 110, No. 28, pp. E2540-E2541.
Hopp, T.P, et al., "A Short Polypeptide Marker Sequence Useful for Recombinant Protein Identification and Purification," *Bio/Technology*, Oct. 1988, vol. 6, pp. 1204-1210.
International Search Report for International Patent Application No. PCT/CA2014/000537 mailed Sep. 29, 2014, 7 pages.
Kubagawa, H. et al., "The Old but New IgM Fc Receptor (FcμR)," in Fc Receptors, Current Topics in Microbiology and Immunology 382, 2014, Daëron, M. et al. (eds.), Springer International Publishing Switzerland, pp. 3-28.
Lang, P.A. et al., "Aggravation of viral hepatitis by platelet-derived serotonin," *Nature Medicine*, Jul. 2008, vol. 14, No. 7, pp. 756-761.
Lang, K.S. et al., "Reply to Honjo et al.: Functional relevant expression of Toso on granulocytes," PNAS, Jul. 9, 2013, vol. 110, No. 28, pp. E2542-E2543.
Lutz-Freyermuth, C. et al., "Quantitative determination that one of two potential RNA-binding domains of the A protein component of the U1 small nuclear ribonucleoprotein complex binds with high affinity to stem-loop II of U1 RNA," *Proc. Natl. Acad. Sci. USA*, Aug. 1990, vol. 87, pp. 6393-6397.

Martin, G.A. et al., "GAP Domains Responsible for Ras p21-Dependent Inhibition of Muscarinic Atrial K+ Channel Currents," *Science*, Jan. 10, 1992, vol. 255, pp. 192-194.
MedlinePlus, "Autoimmune disorders: MedlinePlus Medical Encyclopedia," located at <http:www.nlm.nig.gov/medlineplus/ency/article/000816.htm>, 4 pages.
Nguyen, X-H. et al., "Toso regulates the balance between apoptotic and nonapoptotic receptor signaling by facilitating RIP1 ubiquitination," *Blood*, Jul. 21, 2011, vol. 118, No. 3, pp. 598-608.
Nguyen, X-H. et al., "Antiapoptotic function of Toso (Faim3) in death receptor signaling," Blood, Feb. 16, 2012, vol. 119, No. 7, pp. 1790-1791.
Oettgen, H.C. et al., "IgE regulation and roles in asthma pathogenesis," *J Allergy Clin Immunol*, 2001, vol. 107, pp. 429-440.
Paborsky, L.R. et al., "Mammalian cell transient expression of tissue factor for the production of antigen," *Protein Engineering*, 1990, vol. 3, No. 6, pp. 547-553.
Shima, H. et al., "Identification of TOSO/FAIM3 as an Fc receptor for IGM," *International Immunology*, 2009, vol. 22, No. 3, pp. 149-156.
Skinner, R.H. et al., "Use of the Glu-Glu-Phe C-terminal Epitope for Rapid Purification of the Catalytic Domain of Normal and Mutant ras GTPase-activating Proteins," *The Journal of Biological Chemistry*, Aug. 5, 1991, vol. 266, No. 22, pp. 14163-14166.
Sriram, S. et al., "Experimental Allergic Encephalomyelitis: A Misleading Model of Multiple Sclerosis," *Ann Neurol*, 2005, vol. 58, pp. 939-945.
Steinman, L., et al., "How to Successfully Apply Animal Studies in Experimental Allergic Encephalomyelitis to Research on Multiple Sclerosis," *Ann Neurol*, 2006, vol. 60, pp. 12-21.
Stern, B. et al., "Improving mammalian cell factories: The selection of signal peptide has a major impact on recombinant protein synthesis and secretion in mammalian cells," *Trends in Cell & Molecular Biology*, 2007, vol. 2, pp. 1-17.
Topalian, S.L. et al., "Safety, Activity, and Immune Correlates of Anti-PD-1 Antibody in Cancer," *The New England Journal of Medicine*, Jun. 28, 2012, vol. 366, No. 26, pp. 2443-2454.
Zhang, L. et al., "Alteration in the IL-2 signal peptide affects secretion of proteins in vitro and in vivo," *The Journal of Gene Medicine*, 2005, vol. 7, pp. 354-365.
Achiron, A. et al., "Impaired Expression of Peripheral Blood Apoptotic-Related Gene Transcripts in Acute Multiple Sclerosis Relapse," *Ann. N.Y. Acad. Sci.*, 2007, vol. 1107, pp. 155-167.

* cited by examiner

FIG 1

Toso-binding scFv heavy and light chain amino acid sequences

VH = variable heavy chain; VL = variable light chain; underlined sequences identify CDRs in order of CDR1 (first underlined group in sequence), CDR2 (second underlined group in sequence), CDR3 (third underlined group in sequence)

| Phage clone's name | Sequence's name | sequence |
|---|---|---|
| 3kr7 | 3kr7-VH | EVQLVQSGGGLVQPGGSLRLSCVAS<u>DFFMNYN</u>MNWVRQAPGKGLEWLSF<u>IDTSYTTY</u>YADSVRGRFTISRDNSKKSLFLQM NTLTDDDTAVYFCA<u>RDYYGSSYWGGHYFHAMDY</u>WGQGTPVTVSSASTKGPK (SEQ ID NO: 1) |
| | 3kr7-VL | EIVLTQSPATLSLSSPGERATLSCRAS<u>QSVGTS</u>LAWYQQIPGQAPSLLIH<u>DAS</u>NRASGIPARFSGSGSGTDFTLTINSLEPEDFAVYY C<u>QQRSNGPPSWT</u>FGQGTKVEIKRTVAAPSVFAA (SEQ ID NO: 2) |
| k-2-5 | k-2-5-VH | AGAAGAVWGDVVHPGGSLRISCEGSGS<u>GFSESDFG</u>IHWVRQAPGKGLEWVAV<u>VRYDGSKE</u>YYADSVKGRFTISRDNARNTVHL ELDSLRSEDTAVYFCA<u>KDEMARWAYVDWLPHLHHSYGMDY</u>WGQGTTVIVSSASTKGPK (SEQ ID NO: 3) |
| | k-2-5-VL | VEIVLTQSPATLSVSPGERATLSCRAS<u>QSVSSN</u>LAWYQQKPDQAPRLLIY<u>GAS</u>TRATGIPARFSGSGSGTEFTLTISSLQSEDFAVY YC<u>QQYNNWPYT</u>FGQGTKLEIK RTVAAPSVF (SEQ ID NO: 4) |
| 5/7k5 | 5/7k5-VH | AGAAGAVWGDVVHPGGSLRISCEGSGS<u>GFSESDFG</u>IHWVRQAPGKGLEWVAV<u>VRYDGSKE</u>YYADSVKGRFTISRDNARNTVHL ELDSLRSEDTAVYFCA<u>KDEMARWAYVDWLPHLHHSYGMDY</u>WGQGTTVIVSSASTKGPK (SEQ ID NO: 5) |
| | 5/7k5-VL | VEIVLTQSPATLSVSPGERATLSCRAS<u>QSVSSN</u>LAWYQQKPDQAPRLLIY<u>GAS</u>TRATGIPARFSGSGSGTEFTLTISSLQSEDFAVY YC<u>QQYNNWPYT</u>FGQGTKLEIN ELWLHHLS (SEQ ID NO: 6) |
| 5/7k1 | 5/7k1-VH | QVQLVQSGGGLFQPGGSLRLSCAAS<u>GFTFSNWW</u>MHWVRQAPGKGLVWVSR<u>IKRDATST</u>TYGDSVKGRFTISRDNAKNTLYL QMKSLRVDDTAVYYC<u>VREGGYTYGG</u>VYYYNGMDVWGQGTTVTVSSAASTKGPK (SEQ ID NO: 7) |
| | 5/7k1-VL | DIEMTQSPDSLAVSLGERATINCKS<u>SQSVFSSSYEDY</u>LAWYQQKPGQAPKLLIY<u>WAS</u>TRESGVPDRFTGSGSGTDFTLTISSLQ VEDVAVYYCQ<u>QYYEPYT</u>FGQGTRLEIKRTVAAHMSSRP (SEQ ID NO: 8) |
| 5/7k6 | 5/7k6-VH | EVQLVQSGGGLVQPGGSLRLSCVAS<u>DFFMNYN</u>MNWVRQAPGKGLEWLSF<u>IDTSYTTY</u>YADSVRGRFTISRDNSKKSLFLQM NTLTDDDTAVYFCA<u>RDYYGSSYWGGHYFHAMDY</u>WGQGTPVTVSSASTKGPK (SEQ ID NO: 9) |
| | 5/7k6-VL | VEIVLTQSPATLSSSPGERATLSCRAS<u>QSVGTS</u>LAWYQQIPGQAPSLLIH<u>DAS</u>NRASGIPARFSGSGSGTDFTLTINSLEPEDFAVY YC<u>QQRSTGLRVGR</u>SAKGPRWKSNGTVAAPSVF (SEQ ID NO: 10) |
| 5/15kL24 | 5/15kL24-VH | GGAAVESGGGLVQPGGSLRLSCVAS<u>GFTFSSYD</u>MIWVRQAPGKGLEWVSA<u>ISGSGGS</u>PYYADSVRGRFTISRDNSKGTLFLQ MNSLRAEDTAVYFCA<u>KPYTSGWYY</u>VGCDSWGQGTLVTVSSASTKGPK (SEQ ID NO: 11) |
| | 5/15kL24-VL | VEIVLTQSPRTLSLSPGERATLSCRAS<u>QSVSSY</u>LAWYQQRPGQAPRLLYGA<u>SS</u>RATGIPDRFSGSGSGTDFTLTISRLEPEDFAV YYC<u>QQYGSSPWT</u>FGQGTKVEIKRDCGCTICL (SEQ ID NO: 12) |
| 5/15kL26 | 5/15kL26-VH | GGAAVESGGGLVQPGGSLRLSCAAS<u>GFTFSDCA</u>MGWVRQAPGKGPEWVAA<u>ISGSGLST</u>YYTGSVKGRFSISRDNSKSTMFLQ |

| Phage clone's name | Sequence's name | sequence |
|---|---|---|
| 5/15kL30 | 5/15kL26-VL | MDSLSAGDTALYYCTKAPWDYYGSGNTDHFDHWGQGTLVTVSSASTKGPK (SEQ ID NO: 13) |
| | 5/15kL30-VH | VEIVLTQSPATLSLSPGERATLSCRASQSVRSYLAWYRQRPGQAPRLLIYDATYRAAGIPARISGSGSGTDFTLTISSLEPEDFAVYY CQQRNNWPLTFGGGTKVEIRRLWLHHLS (SEQ ID NO: 14) |
| | 5/15kL30-VL | GGAAVGVWGRLGTAWGSLRLSCTATGFTFSSHAMSWVRQAPGKGPEWVSASGRGSSINYADSVKGLFTVSRDNFKNMLSL QMNSLRADDTAVYYCAKGLAPEYWGQGTLVTVSSASTKGPK (SEQ ID NO: 15) |
| k-4.15 | | VEIVMTQSPATLSLSPGERATLSCRASQSVSSYLAWYQQKPGQAPRLLIYDASNRATGIPARFSGSGSGTDFTLTISSLEPEDFAV YYCQQRSNWPPYSFGQGTKLEIKRKLWLHHLS (SEQ ID NO: 16) |
| | k-4.15-VH | GGAAVESGGELRKPGESLKLSCQTSGYDFANFWIGWVRQMPGKGLEWVGIIYPDSDVNYSPGFQGHVAISADKSISTVYLE WSSLKASDSGIYYCTRRYSGAOLGVDSWGLGTLVTVSSASTRAQ (SEQ ID NO: 17) |
| | k-4.15-VL | RRVLTQSPDTLSLSPGERVTLSCRASQRVMTGYLAXYQQKPGQAPRLLIYGASRRATGVPDRFSGSGSGTDFTLSISRVGPDDF AIYYCQQHGTSPYTFGQGXRLXIK RTVAATICL (SEQ ID NO: 18) |
| k-4.16 | k-4.16-VH | QVQLVQSGAEVKKPGASVKVSCKASGYTFTSYGISWVRQAPGQGLEWMGWISVYNGNTNYAQNLQGRVTMTDTSTSTAY MELXSLRSDDTAVYYCARDGLRWLRPTGMDYWGQGTLVTVSSASTKGPK (SEQ ID NO: 19) |
| | k-4.16-VL | VDIEMTQSPSSLSASVGDRVTITCQASQDYHSLNWFQQKPGKAPKLLIYDASNLETGVPSRFSGXGSGTDFTFTIXSLQPEXFAT YYCQQYDNWPITFGQGTRLEIK RTVAHLS (SEQ ID NO: 20) |
| k-4.18 | k-4.18-VH | AGAIVQSGGGLVQPGGSLRLSCSASGFTFSSYAMHWVRQAPGKGLEYVSAISSSGINTYADSVKGGFTISRDNSKNTLFLQM SSLRVEDTAVYYCVKGSGWGYQQYYGMDVWGPRDHGHRFLRLHQGPK (SEQ ID NO: 21) |
| | k-4.18-VL | VDIMTQSPDSLAVSLGERATINCKSSQSVLVRSMKKAYLAWYQQKPGCQPPKLLTYWASTRESGVPDRFTGSGSRTDFTLTISS LQAEDVAVYYCQQYYGTPLTFGGGTKVEIK RRLWLHHLS (SEQ ID NO: 22) |
| k-4.20 | k-4.20-VH | AGQLVQSGAEARRPGASVKVSCKASGYSLSDYSVHWVRQTRDQGLEWMGWINPKTGGTTYAQNFQARVTMTRDTSINTAY MELRRLRYDDTGVYFCARPGFCTIDMCHDFDSWGHGSLITVSSASTKGPK (SEQ ID NO: 23) |
| | k-4.20-VL | VDIVMTQTPLSLPVTLGQPASISCRSSQRLVYSDGNTYLNWFQQRPGQSPRRLIYKVSNRDSGVPDRFSGSGSGTAFTLKISRVE AEDVGIYYCMQSSTDWPWTFGQGTRVEIK RTVAAPSVF (SEQ ID NO: 24) |
| k-4.17 | k-4.17-VH | QVQLQQSGAEVKRPGASVKVSCKASGYTFSDYYMYWVRQAPGQRLEWMGRINPKTGGTNYAQHFQGRVTMTRDTSISTAY MEFSRLTSDDTAVYYCARRSNLYYDYGMDVWGQGTTVVSSASTKGPK (SEQ ID NO: 25) |
| | k-4.17-VL | VDIVMTQAPLSLAVSLGERATINCKSSRSVLYTSTNRYLLAWYQQKPGQPPKLLIYWASTRESGVPDRFSGSSGTDFTLTISSV QAEDVAVYYCQQYYMPPYTFGQGTRLEIK KTVAAPSVF (SEQ ID NO: 26) |
| L-1-13 | L-1-13-VH | QVQLQQSGPGLVRPSETLSLACSVSGALVTNTAYYWGWFRQSPGQGLEWIGCYANGRTYTNPSLKSRVSLIDQSRQRFSLN LTSATATDTAVYYCVRLVPKBTATLWYIDVWGKGTTVTVSSGGASAPK (SEQ ID NO: 27) |
| | L-1-13-VL | VQSALTQPASASASLGASVKLTCTLSSGHSSYAIAWHQQQPEKGPRYLMKLNSDGSHSKGNGIPDRFSGSSSGAERYLTISSLQS EDEADYYCQTWGTGIWVVFGGGTKLTVLGQPKAPPSVTLFPPSS (SEQ ID NO: 28) |
| 1R2kr3 | 1R2kr3-VH | QVQLQQSGAEVRKPGSSVNVSCKASGDTSSYAISWVRQAPGQGLEWMGRINPIPRTTYAQKFQDRATITADISTSTVYMDL |

FIG 1 (cont.)

| Phage clone's name | Sequence's name | sequence |
|---|---|---|
| | | SSLTSEDTAVYYCARDCSGGSCFRDDAFDWGQGIMVTVSSASTKGPK (SEQ ID NO: 29) |
| | 1R2kr3-VL | ILSQAPLSLSASIGDSVTITCRASQSVSDYLNWYQQKPGKAPKLLIYAASSLQSGVPSRFIGSGSGTDFTLTISSLQPEXFATYYCQQ SYTTAYTFGQGTKLEIQRXXAAPSVF (SEQ ID NO: 30) |
| K3-22 | K3-22-VH | QVQLQQSGAEVRKPGSSVNVSCKASGDTSSIYAISWVRQAPGQGLEWMGRINWPIPRITYAQKFQDRATITADISTSTVYMDL SSLTSEDTAVYYCARDCSGGSCFRDDAFDWGQGIMVTVSSASTKGPK (SEQ ID NO: 31) |
| | K3-22-VL | ILSQAPLSLSASIGDSVTITCRASQSVSDYLNWYQQKPGKAPKLLIYAASSLQSGVPSRFIGSGSGTDFTLTISSLQPEDFATYYCQ QSYTTAYTFGQGTKLEIQRTVAAPSVF (SEQ ID NO: 32) |
| k-2-48 | k-2-48-VH | QVQLVQSGAEVKKPGASVKVSCKASGYTLTSYDVNWVRQATGQGLEWMGWMNPNSGNTGYAQKFQGRVTMTRNTSIGT AYMELNSLTSDDTAVYYCARGRIWHYYGLDVWGHGTTVTVSSASTKGPK (SEQ ID NO: 33) |
| | k-2-48-VL | VEIVLTQSPATLSLSPGERATLSCRASQSVSSYLAWYQQKPGQAPRLLIYDASNRATGIPARFSGSGSGTDFTLTISSLEPEDFAVY YCQQRSNWPWITFGQGTKVEIKRTVAAPSVF (SEQ ID NO: 34) |
| K3-24 | K3-24-VH | MAEVQLVQSGGGLVQPGGSLRLSCVASDFFNIYWMNWVRQAPGKGLEWLSFIDTSTYTYYADSVRGRFTISRDNSKKSLFL QMNTLTDDDTAVYFCARDRYGSSYWGAHYFHAMDYWGQGTPVTVSSASTKGPK (SEQ ID NO: 35) |
| | K3-24-VL | VEIVLTQSPATLSSSPGERATLSCRASQSVGTSLAWYQQIPGQAPSLLIHDASNRASGIPARFSGSGSGTDFTLTINSLEPEXFAVY YCQQRSAGPPSWTFGQGTKVEIKRTVAAPSVF (SEQ ID NO: 36) |
| 5/15L28 | 5/15L28-VH | AGAAGAVWGRPGQAGGSLRLSCAAAGFSFSSYNLNWVRQAPGKGLEWILSSESSGSSYIYYADSVKGRFTISRDNAKNSLYLQ MNSLRAEDTAVYYCTRDRYYHDSDEYYDADGFDWGQGTLVTVSSASTKGPK (SEQ ID NO: 37) |
| | 5/15L28-VL | VDILMTQSPSSLSASVGDRVTITCRASQSYSYLNWYQQKPGKAP*LLIYAASLQSGVPSRFSGSGSGTDFTLTISSLQPEDFATY YCQQSYSTLSLSAEGPRWRSNELWLHHLS (SEQ ID NO: 38) |
| 5/15kL19 | 5/15kL19-VH | EVQLLESGEGLVQPGGSLRLSCAAS GFTFNTYAMSWVRQVPGKGLEWVSSISANGGTTYYGDSVRGRFTISRDNAKNTLYLQ MNSLTAEDTAKYYCARDHLWFGEYYFDCWGQGTLVSVSSLHQGPK (SEQ ID NO: 39) |
| | 5/15kL19-VL | VDIEMTQSPDSLAVSLGERATINCKSSQSVESSSSEDYLAWYQQKPGQAPKLLIYWASTRESGVPDRFTGSGSGTDFTLTISSL QVEDVAVYYCQQYYHTFGQGTRLEI*TNCGCTICL (SEQ ID NO: 40) |
| k-5.10 | k-5.10-VH | GGAVVQSGGGMVKPGASVKVSCKASGFTFDAWMIWVRQAPGKGLEWVGRIKSRTGGGTTDYAAPVQGRFTISRDDSKAT VYLQMNSLNTEDTAVYFCVWSGHWMFGHWGQGTLVTVSSASTKGPK (SEQ ID NO: 41) |
| | k-5.10-VL | VDIVMTQAPLSSPVTLGQPASISCRSSQSLVHSDGNTYLSWLQQRPGQPPRLLIYKISNRFSGSQTDSVAVGQGQISH*KSAGW KLRMSGFITACKLMWLTLLARGXSWRSKKTVAAPSVF (SEQ ID NO: 42) |
| k-2-42 | k-2-42-VH | QVQLVQSGAEVKKPGASVKVSCKASGYTLTSYDVNWVRQATGQGLEWMGWMNPNSGNTGYAQKFQGRVTMTRNTSIGT AYMELNSLTSDDTAVYYCARGRIWHYYGLDVWATGPRSPSPQPPPRAQ (SEQ ID NO: 43) |
| | k-2-42-VL | VDIVMTQTPLSLSASVGDRVTITCRANQDISNYLNWYCQKPRKAPMLLIYAASSLQSGVPSRFSGSGSGTDFTLTISSLQPEDFAT YYCQQSYSTPETFGQGTKVEIK RTVAAPSVF (SEQ ID NO: 44) |
| 1R2kr30 | 1R2kr30-VH | GGLVQPGGSLRLSCVASDFFNIYWMNWVRQAPGKGLEWLSFIDTSTYTYYADSVRGRFTISRDNSKKKSLFLQMNTLTDDDT |

FIG 1 (cont.)

| Phage clone's name | Sequence's name | sequence |
|---|---|---|
|  |  | AVYFC*AWDRYG*SSYWGATISTWTSGGKGPRSPSPQPPPRAQ (SEQ ID NO: 45) |
|  | 1R2kr30-VL | RRYCDDSGSTLTVCICRRQSHITCRAS*QSESS*YLNWYQQKPGKAPKLLIY*AAS*SLQSGVPSRFSGSGSGTDFTLTISSLQPEDFATY YC*QQSYSTPCT*FGQGTKLEIK RTVAAPSVF (SEQ ID NO: 46) |
| K1 | K1-VH | AGELVQSGAEVRKPGESLQISCTAS*GYIFTDYYM*IGWVRQMPGKGLESMGII*YPGDSET**SSPSFQGQVIMSVDKYRNIAYLQW NSLKASDTATYFC*ARH*GRGYC*GGGSCQ*GTLIDMWGQGTLLTVSAASTKGPK (SEQ ID NO: 47) |
|  | K1-VL | VDIEMTQSPDSLAVSLGERATINCKSS*QSVFSSYSDDY*LAWYQQKPGQAPKLLIY*WAST*RESGVPDRFTGSGSGTDFTLTISSL QVEDVAVYYC*QQYYITPIT*FGQGTRLEIK RTVAAHMSS (SEQ ID NO: 48) |
| L1 | L1-VH | AGELVQSGAEVRKPGESLQISCTAS*GYIFTDYYM*IGWVRQMPGKGLESMGII*YPGDSET**SSPSFQGQVIMSVDKYRNIAYLQW NSLKASDTATYFC*ARH*GRGYC*GGGSCQ*GTLIDMWGQGTLLTVSAASTKGPK (SEQ ID NO: 49) |
|  | L1-VL | VSELTQDPAVSVALGQTGRITCQGD*SLRTY*YANWYQQKPGQAPVLVIY*AKTS*GPQGSQTDSLAPAQETQLT*PSLGAQAEDES DYYC*NSRDSSDNLVV*FGGGTKLTVRGQPKAAPRALCSTPL (SEQ ID NO: 50) |
| k-2-32 | k-2-32-VH | QVQLVQSGAEVKKPGASVKVSCKAS*GYTLTSY*DVNWVRQATGQGLEWMGWM*NPNSGNT*GYAQKFQGRVTMTRNTSIGT AYMELNSLTSDDTAVYYC*ARGRSNM*YYGLDY*WGHGTITVTVSSASPRAQ (SEQ ID NO: 51) |
|  | k-2-32-VL | RRYCETQAPLSLSASVGDRVTITCQAS*QDISN*YLNWYQQKPGKAPKLLIY*DASN*LETGGPSRFSGSGSGTDFTFTISSLQPEDIAT YYC*QQYDNLPPGSP*SAKGHDRRLNELWLHHLS (SEQ ID NO: 52) |
| L-8.2 | L-8.2-VH | AGELVQSGAEVRKPGESLQISCTAS*GYIFTDYYM*IGWVRQMPGKGLESMGII*YPGDSET**SSPSFQGQVIMSVDKYRNIAYLQW NSLKASDTATYFC*ARH*GRGYC*GGGSCQ*GTLIDMWGQGTLLTVSAASTKGPK (SEQ ID NO: 53) |
|  | L-8.2-VL | VSELTQDPAVSVALGQTGRITCQGD*SLRTY*ANWYQQKPGQAPVLVIY*AKN*KRPSGIPDRFSGSSSGNTAYLTITGAQAXDESD YYC*NSRDSSDNLVV*FGGGTKLTVLGQPKAAPSGTLFHPP (SEQ ID NO: 54) |
| L-8.6 | L-8.6-VH | AGELVQSGAEVRKPGESLQISCTAS*GYIFTDYYM*IGWVRQMPGKGLESMGII*YPGDSET**SSPSFQGQVIMSVDKYRNIAYLQW NSLKASDTATYFC*ARH*GRGYC*GGGSCQ*GTLIDMWGQGTLLTVSAASTKGPK (SEQ ID NO: 55) |
|  | L-8.6-VL | VSELTQDPAVSVALGQTGRITCQGD*SLRTY*YANWYQQKPGQAPVLVIY*AKTS*GPQGSQTDSLAPAQETQLT*PSLGAQAEDES DYYC*NSRDSSDNLVV*FGGGTKLTVLGHPKAAPSGTLFHPP (SEQ ID NO: 56) |
| L-8.17 | 8.17-VH | AGELVQSGAEVRKPGESLQISCTAS*GYIFTDYYM*IGWVRQMPGKGLESMGII*YPGDSET**SSPSFQGQVIMSVDKYRNIAYLQW NSLKASDTATYFC*ARH*GRGYC*GGGSCQ*GTLIDMWGQGTLLTVSAASTKGPK (SEQ ID NO: 57) |
|  | 8.17-VL | VSELTQDPAVSVALGQTGRITCQGD*SLRTY*ANWYQQKPGQAPVLVIY*AKN*KRPSGIPDRFSGSSSGNTAYLTITGAQAEDESD YYC*NSRDSSDNLVV*FGGGTKLTVLGQPKAAPSGTLFPPSS (SEQ ID NO: 58) |

Non-Toso binding scFV heavy and light chain amino acid sequences

VH = variable heavy chain; VL = variable light chain; underlined sequences identify CDRs in order of CDR1 (first underlined group in sequence), CDR2 (second underlined group in sequence), CDR3 (third underlined group in sequence)

| Phage clone's name | Sequence's name | sequence |
|---|---|---|
| K3-13 | K3-13-VH | AGTAAAVWGRLGTAGGSLRLSRTASGFTFSNYAMSWVRQAPGKGLQWVSGISATGVSTYYADSVKGRFAISRDNSKSTVFLQM NSLRAEDTAIYYCAKYRIAIEVAYDYWGQGTLVTVSSASTKGPK (SEQ ID NO: 59) |
| | K3-13-VL | LRLHSSLAASVGDRVTITCRASQSVSTYLNWYQQLPGKAPKLLISGASTLQSGVPSRFSGSGSGTDFTLTISSLQPEDSALYFCQQSYI YLTFGGGTRVEIKRLWLHHLS (SEQ ID NO: 60) |
| 5/7k12 | 5/7k12-VH | QVQLVQSGGGLVQPGGSLRLSCVASEFFWYAMNWVRQAPGKGLEWLSFIDTSTYTYYADSVMGRFTISRDNSKKSLFLQM NTLTDEDTAVYFCAMDRYGSSYWGGHYEHAMDYWGQGTPVTVSSASTKGPK (SEQ ID NO: 61) |
| | 5/7k12-VL | VEIVLTQSPPTLSVSPGERATLSCRASQSVSSMLAWYQQKPGQAPRLLIYGASTRATGIPARFSGSGSGTEFTLTISSLQPEDFATYYC QQSYSTPITFGQGTRLEIKRTVAAPSV (SEQ ID NO: 62) |
| k-5.2 | k-5.2-VH | AGAAGAVWGGSVQPGGSLRLSCVASGFSINGYDLSWVRQARGKGLEWVSYSPTGTTTRYSDSVKGRFTISRDNAKNSLHLQM NSLQDGDTAVYYCARHWMWGQGTLVTVSSASTKGPKLEEGEFSEA (SEQ ID NO: 63) |
| | k-5.2-VL | RRYCDAQTPLSLPVTLGQPASISCRSSQSLVYSDGNTYLNWFQQRPGQSPRRLIYKVENRDSGVPDRFSGSGSGTDFTLKISRVEAE DVGVYYCMQGTHWPPYTFGQGTRLEIKRTVAAPSVF (SEQ ID NO: 64) |
| L-4.4 | L-4.4-VH | QVQLVQSGGAEVKKPGESLKISCKASGYSFTNYWIAWVRQMPGKGLEWMGIYPGDLETRYRPSFQGQVTISADKSLSTAYLQWS SLEASDTATYYCARAHYYDTTAYSLYYYPMDVWGQGPRSSSPQQPPRAQ (SEQ ID NO: 65) |
| | L-4.4-VL | VSYELTQPPSVSVSPGQTASITCSGDKLLGEKYVCWYQQKPGQSPVAVIYQDDSKRPSGIPERFSASNSANTATLTISGTQAMDEADY YCQAAWDQAWDSNTVFGGGTRLTVLSQPKAAHSVTLFPPSS (SEQ ID NO: 66) |
| k-4.13 | K-4.13-VH | EVQLLESGGGLVQPGGSQRLSCAASGFEESDYDMHWVRQTGKGLEWVSGIGTASDIHYAGTVKGRFTISRENARNSLYLQMN SLRAGDTAVYYCVRGSIAAHVVGINMDVWGRGTTVTVSSASTKGPK (SEQ ID NO: 67) |
| | k-4.13-VL | VDIEMTQSPSSLSASVGDRVTITCRASQSISSYLNWYQQKPGKAPKLLIYAASLQSGVPSRFSGSGSGTDFTLTISSLQPEDFATYYC QQSYSTPYTFGQGTKLEIEDCGCTICLRGRWIQRYQS*NC*KL (SEQ ID NO: 68) |
| L-8.4 | L-8.4-VH | AGELVQSGAEVRKPGESLQISCTASGYFTDYWIGWVRQMPGKGLESMGIIYPGDSET*SSPSFQGQVIMSVDKYRNIAYLQWN XLKASDTATYFCARMERGYCGGGSCQGTLDAWGQGTLLTVSAASTKGPK(SEQ ID NO: 69) |
| | L-8.4-VL | VSELTQDPAVSVALGQTGRITCQGDKLTYANWYQQKPGQAPVLVIYAKNKRPSGIPDRFSGSSSGNTAYLTITGAQAEDESDYY CNSRDSSDNLVVFGGGTKLTVLGSAQGCPLGHSVPPSS (SEQ ID NO: 70) |

ANTIBODIES TO TOSO

CROSS REFERENCES TO RELATED APPLICATIONS

The present application claims the benefit of U.S. Provisional Application No. 61/842,766, filed Jul. 3, 2013, the content of which is expressly incorporated herein by reference in its entirety for all purposes.

BACKGROUND OF THE INVENTION

Toso or Faim3 (Fas Apoptotic inducing molecule 3) is a single membrane spanning cell surface receptor originally characterized through a retroviral overexpression screen in Jurkat cells, a T cell leukemic line, as a mediator of Fas-induced apoptotic cell death (Hitoshi, Y., et al., Toso, a cell surface, specific regulator of Fas-induced apoptosis in T cells. Immunity, 1998. 8(4): p. 461-71). Subsequent studies have suggested that Toso is the elusive receptor for IgM. The expression of Toso also seems to correlate with particularly aggressive forms of Chronic Lymphocytic Leukemia, or CLL. Modulation of Toso activity may also affect immune system disorders.

There is a need for molecules that are able to modulate Toso activity.

SUMMARY OF THE INVENTION

Accordingly, the present invention provides methods and compositions for modulating Toso activity and treating diseases and disorders in which Toso is implicated.

In one aspect, the present invention provides antibodies that bind to Toso or to a ligand of Toso.

In a further aspect, the present invention provides an antibody comprising a heavy chain variable region comprising any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57.

In a further embodiment, the present invention provides an antibody comprising a heavy chain variable region having a sequence with at least about 95% sequence identity to any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, wherein the antibody binds Toso.

In a further aspect, the present invention provides an antibody comprising a light chain variable region comprising any one of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58.

In a further embodiment, the present invention provides an antibody comprising a light chain variable region having a sequence with at least about 95% sequence identity to any one of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, wherein the antibody binds Toso.

In a further aspect, the present invention provides an antibody comprising: a first heavy chain CDR comprising any of the CDR1 sequences listed in Table 1, a second heavy chain CDR comprising any of the CDR2 sequences listed in Table 1, a third heavy chain CDR comprising any of the CDR3 sequences listed in Table 1, a first light chain CDR comprising any of the CDR1 sequences listed in Table 2, a second light chain CDR comprising any of the CDR2 sequences listed in Table 2, and a third light chain CDR comprising any of the CDR3 sequences listed in Table 2, wherein said antibody binds Toso.

In a still further aspect, the antibodies described herein encompass humanized antibodies.

In a still further aspect, the present invention provides a nucleic acid encoding an antibody in accordance with any of the above-described antibodies.

In a yet further aspect, the present invention provides an expression vector, that encodes an antibody in accordance with any of the above-described antibodies.

In a still further aspect, the present invention provides a method of making an antibody in accordance with any of the above-described antibodies, where the method includes the step of providing a cell comprising a nucleic acid encoding the antibody, where the cell is cultured under conditions suitable for expression of the antibody.

In a yet further aspect, the present invention provides methods for treating a Toso-associated disease that include treating a subject in need thereof with an antibody in accordance with any of the above-described antibodies

BRIEF DESCRIPTION OF THE DRAWINGS

FIG. 1 provides sequences of antibodies that bind to Toso. Asterisks denote stop codons, which can in some embodiments be removed by protein engineering methods known in the art to allow for expression of the full length sequence.

FIG. 2 provides sequences of antibodies that do not bind to Toso. Asterisks denote stop codons, which can in some embodiments be removed by protein engineering methods known in the art to allow for expression of the full length sequence.

DETAILED DESCRIPTION OF THE INVENTION

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

In order that the application may be more completely understood, several definitions are set forth below. Such definitions are meant to encompass grammatical equivalents.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

A "composition" may include any substance comprising an agent or compound and is also intended to encompass any combination of an agent or compound and other substances, including a carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

As used herein, the term "patient" or "subject" intends an animal, a mammal or yet further a human patient. For the purpose of illustration only, a mammal includes but is not limited to a human, a simian, a murine, a bovine, an equine, a porcine or an ovine.

As used herein, the term "oligonucleotide" or "polynucleotide" refers to a short polymer composed of deoxyribonucleotides, ribonucleotides or any combination thereof. Oligonucleotides are generally at least about 10, 15, 20, 25, 30, 40, 50, 60, 70, 80, 90, 100 or more nucleotides in length. An oligonucleotide may be used as a primer or as a probe.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

The term "isolated" as used herein refers to molecules or biological or cellular materials being substantially free from other materials, e.g., greater than 70%, or 80%, or 85%, or 90%, or 95%, or 98%. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source and which allow the manipulation of the material to achieve results not achievable where present in its native or natural state, e.g., recombinant replication or manipulation by mutation. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides, e.g., with a purity greater than 70%, or 80%, or 85%, or 90%, or 95%, 98%, or 99%. The term "isolated" is also used herein to refer to cells or tissues that are isolated from other cells or tissues and is meant to encompass both cultured and engineered cells or tissues.

A "recombinant" nucleic acid refers an artificial nucleic acid that is created by combining two or more sequences that would not normally occur together. In one embodiment, it is created through the introduction of relevant DNA into an existing organismal DNA, such as the plasmids of bacteria, to code for or alter different traits for a specific purpose, such as antibiotic resistance. A "recombinant" polypeptide is a polypeptide that is derived from a recombinant nucleic acid.

As used herein, the term "promoter" refers to a nucleic acid sequence sufficient to direct transcription of a gene. Also included in the invention are those promoter elements which are sufficient to render promoter dependent gene expression controllable for cell type specific, tissue specific or inducible by external signals or agents.

In some embodiments, a promoter is an inducible promoter or a discrete promoter. Inducible promoters can be turned on by a chemical or a physical condition such as temperature or light. Examples of chemical promoters include, without limitation, alcohol-regulated, tetracycline-regulated, steroid-regulated, metal-regulated and pathogenesis-related promoters. Examples of discrete promoters can be found in, for examples, Wolfe et al. Molecular Endocrinology 16(3): 435-49.

As used herein, the term "regulatory element" refers to a nucleic acid sequence capable of modulating the transcription of a gene. Non-limiting examples of regulatory element include promoter, enhancer, silencer, poly-adenylation signal, transcription termination sequence. Regulatory element may be present 5' or 3' regions of the native gene, or within an intron.

Various proteins are also disclosed herein with their GenBank Accession Numbers for their human proteins and coding sequences. However, the proteins are not limited to human-derived proteins having the amino acid sequences represented by the disclosed GenBank Accession Nos, but may have an amino acid sequence derived from other animals, particularly, a warm-blooded animal (e.g., rat, guinea pig, mouse, chicken, rabbit, pig, sheep, cow, monkey, etc.).

As used herein, the term "Toso", "FAIM3" or "Fas apoptotic inhibitory molecule 3" refers to a protein having an amino acid sequence substantially identical to any of the representative Toso sequences, including any and all versions of GenBank Accession Nos. NP_001135945 (human isoform b), NP_001180267 (human isoform c), NP_005440 (human isoform a), NP_081252 (mouse) or NP_001014843 (rat). Suitable cDNA encoding Toso are provided at GenBank Accession Nos. NM_001142473, NM_001193338, NM_005449, NM_026976, and NM_001014843.

As used herein, the term "biological activity of Toso" or "Toso activity" refers to any biological activity associated with the full length native Toso protein. In some embodiments, the biological activity of Toso refers to binding to an IgM antibody. In further embodiments, the biological activity of Toso refers to inhibiting CD11b or CD18 activity. In yet further embodiments, the biological activity of Toso refers to increasing the activation threshold of granulocytes. Activation threshold can be measured by number of activated granulocytes from bone marrow. In further embodiments, the biological activity of Toso includes the activation of dendritic cells and their ability to present antigen to T cells. In further embodiments, the biological activity of Toso includes inhibition of apoptosis or enhancement of TNF signaling. In some embodiments, the Toso biological activity is equivalent to the activity of a protein having an amino acid sequence represented by GenBank Accession No. NP_001135945, NP_001180267, NP_005440, NP_081252 or NP_001014843, including any and all versions of these accession numbers.

As used herein, the term "treating" refers to administering a pharmaceutical composition for the purpose of improving the condition of a patient by reducing, alleviating, reversing, or preventing at least one adverse effect or symptom of a disease or disorder.

As used herein, the term "preventing" refers to identifying a subject (i.e., a patient) having an increased susceptibility to a disease but not yet exhibiting symptoms of the disease, and administering a therapy according to the principles of this disclosure. The preventive therapy is designed to reduce the likelihood that the susceptible subject will later become symptomatic or that the disease will be delay in onset or progress more slowly than it would in the absence of the preventive therapy. A subject may be identified as having an increased likelihood of developing the disease by any appropriate method including, for example, by identifying a family history of the disease or other degenerative brain disorder, or having one or more diagnostic markers indicative of disease or susceptibility to disease.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, most preferably, a human.

As used herein, the term "substantially identical", when referring to a protein or polypeptide, is meant one that has at least 80%, 85%, 90%, 95%, or 99% sequence identity to a reference amino acid sequence. The length of comparison is preferably the full length of the polypeptide or protein, but is generally at least 10, 15, 20, 25, 30, 40, 50, 60, 80, or 100 or more contiguous amino acids. A "substantially identical" nucleic acid is one that has at least 80%, 85%, 90%, 95%, 96%, 97%, 98% or 99% sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

As used herein, an "amino acid substitution" or "substitution" refers to the replacement of an amino acid at a particular position in a starting polypeptide sequence with another amino acid. For example, the substitution M23Y refers to a variant polypeptide in which the methionine at position 23 is replaced with a tyrosine.

A "biological equivalent" of a protein or nucleic acid refers to a protein or nucleic acid that is substantially identical to the protein or nucleic acid by amino acid or nucleic acid sequence or that has an equivalent biological activity.

As used herein, the term "effective amount" refers to a quantity of compound (e.g., an antibody or biologically active fragment thereof) delivered with sufficient frequency to provide a medical benefit to the patient. In one embodiment, an effective amount of a protein is an amount sufficient to treat or ameliorate a symptom of a disease.

A "population" of cells refers to a collection of more than one cell that is identical (clonal) or non-identical in phenotype and/or genotype.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker.

The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells and have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. In general, the term "antibody" includes any polypeptide that includes at least one constant domain, including, but not limited to, CH1, CH2, CH3 and CL.

Antibodies that find use in the present invention can take on a number of formats as described herein, including traditional antibodies as well as antibody derivatives, fragments and mimetics.

The antibodies can be polyclonal or monoclonal and can be isolated from any suitable biological source, e.g., murine, rat, sheep and canine.

A monoclonal antibody is an antibody produced by a single clone of cells or a hybridoma, and therefore is a single pure homogeneous type of antibody.

A hybridoma is a cell that is produced in the laboratory from the fusion of an antibody-producing lymphocyte and a non-antibody producing cancer cell, usually a myeloma or lymphoma. A hybridoma proliferates and produces a continuous supply of a specific monoclonal antibody.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

"Isotype" as used herein is meant any of the subclasses of immunoglobulins defined by the chemical and antigenic characteristics of their constant regions. It should be understood that therapeutic antibodies can also comprise hybrids of isotypes and/or subclasses.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233# designates a deletion of glutamic acid at position 233. Additionally, EDA233- or EDA233# designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino acid sequence that encodes it. Preferably, the protein variant has at least one amino acid modification compared to the parent protein, e.g. from about one to about seventy amino acid modifications, and preferably from about one to about five amino acid modifications compared to the parent. In some embodiments the parent polypeptide, for example an Fc parent polypeptide, is a human wild type sequence, such as the Fc region from IgG1, IgG2, IgG3 or IgG4, although human sequences with variants can also serve as "parent polypeptides". The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids. Examples include U.S. Pat. No. 6,586,207; WO 98/48032; WO 03/073238; U52004-0214988A1; WO 05/35727A2; WO 05/74524A2; J. W. Chin et al., (2002), Journal of the American Chemical Society 124:9026-9027; J. W. Chin, & P. G. Schultz, (2002), Chem Bio Chem 11:1135-1137; J. W. Chin, et al., (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g. not an amino acid that is coded for by DNA); as will be appreciated by those in the art. For example, homophenylalanine, citrulline, ornithine and norleucine are considered synthetic amino acids for the purposes of the invention, and both D- and L-(R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635): 964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 in IgG1 (also referred to as Asn297 or N297) is a residue at position 297 in the human antibody IgG1.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein. By "Fv" or "Fv fragment" or "Fv region" as used herein is meant a polypeptide that comprises the VL and VH domains of a single antibody.

By "non-naturally occurring modification" as used herein is meant an amino acid modification that is not isotypic. For example, because none of the IgGs comprise a serine at position 434, the substitution 434S in IgG1, IgG2, IgG3, or IgG4 (or hybrids thereof) is considered a non-naturally occurring modification.

By "effector function" as used herein is meant a biochemical event that results from the interaction of an antibody Fc region with an Fc receptor or ligand. Effector functions include but are not limited to ADCC, ADCP, and CDC.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "position" as used herein is meant a location in the sequence of a protein. Positions may be numbered sequentially, or according to an established format, for example the EU index for antibody numbering.

By "target antigen" as used herein is meant the molecule that is bound specifically by the variable region of a given antibody. A target antigen may be a protein, such as the Toso protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the V.kappa., V.lamda., and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

Although the present invention is described primarily with reference to specific embodiments, it is also envisioned that other embodiments will become apparent to those skilled in the art upon reading the present disclosure, and it is intended that such embodiments be contained within the present inventive methods.

I. Overview of the Invention

The present invention is directed to methods and compositions for modulating the activity of the Toso protein (which is also interchangeably referred to herein as "Toso" or "Toso receptor" or "Faim3" or "FCMR"). Methods and compositions of the present invention may be used in accordance with and in some embodiments in combination with other known methods of modulating activity of the Toso protein, such as those described in, for example, U.S. Ser. No. 13/831,031, filed on Mar. 14, 2013, which is hereby incorporated by reference in its entirety for all purposes and in particular for any disclosure, claims, figures, or other teachings related to methods and compositions for modulating activity of the Toso protein.

In some embodiments, the methods and compositions of the invention increase activity of the Toso protein. In other embodiments, the methods and compositions of the invention inhibit activity of the Toso protein.

In certain aspects, compositions for modulating the activity of the Toso protein include agents that bind to the Toso protein or to a ligand of the Toso protein. In further embodiments, the compositions of the invention include an antibody that binds to the Toso protein or to a ligand of the Toso protein.

The present invention is further directed to methods of treating disorders and diseases by administering an antibody that modulates the activity of Toso in a subject. As will be discussed in further detail herein, antibodies of the invention can be used to treat subjects suffering from without limitation Type II diabetes, an autoimmune disorder (including without limitation Type 1 diabetes, multiple sclerosis, or rheumatoid arthritis), asthma, allergy, chronic obstructive pulmonary disease ("COPD"), hyper-IgM syndrome, CLL, lupus, or a neutrophilia-associated disorder (including without limitation neutropenia, severe congenital neutropenia, cyclical neutropenia, antibody mediated neutropenia, reticular dysgenesis, leukocyte adhesion deficiency, familiar myeloproliferative disease, chronic myelogenous leukemia, familiar cold urticaria and leukocytosis, and chronic granulomatous disease).

II. Antibodies to Toso

Antibodies of the invention modulate Toso activity. In some embodiments, antibodies of the invention increase Toso activity. In other embodiments, antibodies of the invention decrease Toso activity. In some embodiments, antibodies of the invention bind directly to the Toso protein. In other embodiments, antibodies of the invention bind to a ligand of the Toso protein. In further embodiments, antibodies of the invention bind or otherwise interact with an intermediate protein or other molecule and indirectly affect Toso activity through that interaction with the intermediate protein or other molecule.

Methods of preparing antibodies are generally known in the art. For example, U.S. Pat. No. 6,727,350 discusses Toso antibodies and methods for preparing the same, and is hereby incorporated by reference in its entirety for all purposes and in particular for all teachings related to antibodies directed to the Toso protein.

In some embodiments, antibodies of the invention are identified by phage display screening using methods known in the art and described in further detail herein. Such methods will in further embodiments include producing a fully human antibody by cloning the results of the phage display screening into an expression vector for human IgG.

Antibodies that find use in the present invention can take on a number of formats as described herein, including traditional antibodies as well as antibody derivatives, fragments and mimetics, described below. In general, the term "antibody" includes any polypeptide that includes at least one constant domain, including, but not limited to, CH1, CH2, CH3 and CL.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to the IgG class, which has several subclasses, including, but not limited to IgG1, IgG2, IgG3, and IgG4. Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)).

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning."

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

Antibody Fragments

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference). The antibody fragments may be modified. For example, the molecules may be stabilized by the incorporation of disulphide bridges linking the VH and VL domains (Reiter et al., 1996, Nature Biotech. 14:1239-1245, entirely incorporated by reference).

Chimeric and Humanized Antibodies

In some embodiments, the scaffold components can be a mixture from different species. As such, if the protein is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region.

Toso Antibodies and Variants

As used herein, the term "Toso antibody" refers to any antibody that binds to Toso or binds to a ligand of Toso, including antibodies comprising any of the sequences described herein and variants thereof.

In certain aspects, Toso antibodies of the invention include antibodies comprising CDR sequences as provided in FIG. 1 and below in Tables 1 and 2.

TABLE 1

CDR sequences of Toso antibodies-heavy chain

| Clone | CDR1 | CDR2 | CDR3 |
|---|---|---|---|
| 3kr7 | DFIFNNYN (SEQ ID NO: 71) | IDTSTYTT (SEQ ID NO: 72) | ARDRYGSSYWGGHYFHAMDV (SEQ ID NO: 73) |
| k-2-5 | GFSFSDFG (SEQ ID NO: 74) | VRYDGSKE (SEQ ID NO: 75) | AKDEMARWAYVDWLPHLHHSYGMDV (SEQ ID NO: 76) |
| 5/7k5 | GFSFSDFG (SEQ ID NO: 77) | VRYDGSKE (SEQ ID NO: 78) | AKDEMARWAYVDWLPHLHHSYGMDV (SEQ ID NO: 79) |
| 5/7k1 | GFTFSNHW (SEQ ID NO: 80) | IKRDATST (SEQ ID NO: 81) | VREGGYTYGGVYYYNGMDV (SEQ ID NO: 82) |
| 5/7k6 | DFIFNNYN (SEQ ID NO: 83) | IDTSTYTT (SEQ ID NO: 84) | ARDRYGSSYWGGHYFHAMDV (SEQ ID NO: 85) |
| 5/15kL24 | GFTFSSYD (SEQ ID NO: 86) | ISGSGGSP (SEQ ID NO: 87) | AKPYTSGWYVGCDS (SEQ ID NO: 88) |
| 5/15kL26 | GFTFSDCA (SEQ ID NO: 89) | ISGSGLST (SEQ ID NO: 90) | TKAPWDYYGSGNTDHFDH (SEQ ID NO: 91) |
| 5/15kL30 | GFTFSSHA (SEQ ID NO: 92) | ISGRGSSI (SEQ ID NO: 93) | AKGLADFDY (SEQ ID NO: 94) |
| k-4.15 | GYDFANFW (SEQ ID NO: 95) | IYPDDSDV (SEQ ID NO: 96) | TRRYSGAQLGVDS (SEQ ID NO: 97) |
| k-4.16 | GYTFTSYG (SEQ ID NO: 98) | ISVYNGNT (SEQ ID NO: 99) | ARDGLRWLRPTGMDV (SEQ ID NO: 100) |

TABLE 1-continued

CDR sequences of Toso antibodies-heavy chain

| Clone | CDR1 | CDR2 | CDR3 |
|---|---|---|---|
| k-4.18 | GFTFSSYA (SEQ ID NO: 101) | ISSSGTNT (SEQ ID NO: 102) | VKGSGVGYQYYYGMDV (SEQ ID NO: 103) |
| k-4.20 | GYSLSDYS (SEQ ID NO: 104) | INPKTGGT (SEQ ID NO: 105) | ARPGFCTIDNCHDFFDS (SEQ ID NO: 106) |
| k-4.17 | GYTFSDYY (SEQ ID NO: 107) | INPKTGGT (SEQ ID NO: 108) | ARRSLNLYYDYGMDV (SEQ ID NO: 109) |
| L-1-13 | GALVTNTAYY (SEQ ID NO: 110) | IYANGRT (SEQ ID NO: 111) | VRLVPKRTATLHYYIDV (SEQ ID NO: 112) |
| 1R2kr3 | GDTSSIYA (SEQ ID NO: 113) | INPIPRIT (SEQ ID NO: 114) | ARDCSGGSCFRQDAFDI (SEQ ID NO: 115) |
| K3-22 | GDTSSIYA (SEQ ID NO: 116) | INPIPRIT (SEQ ID NO: 117) | ARDCSGGSCFRQDAFDI (SEQ ID NO: 118) |
| k-2-48 | GYTLTSYD (SEQ ID NO: 119) | MNPNSGNT (SEQ ID NO: 120) | ARGRSIINHYYGLDV (SEQ ID NO: 121) |
| K3-24 | DFIFNNYN (SEQ ID NO: 122) | IDTSTYTT (SEQ ID NO: 123) | ARDRYGSSYWGGHYFHAMDV (SEQ ID NO: 124) |
| 5/15L28 | GFSFSSYN (SEQ ID NO: 125) | ISSGSSYI (SEQ ID NO: 126) | TRDRYYHDSDEYYDADGFDV (SEQ ID NO: 127) |
| 5/15kL19 | GFTFNTYA (SEQ ID NO: 128) | ISANGGTT (SEQ ID NO: 129) | ARDHLWFGEYIFDC (SEQ ID NO: 130) |
| k-5.10 | GFTFTDAW (SEQ ID NO: 131) | IKSRTGGGTT (SEQ ID NO: 132) | VWSGRNWFGH (SEQ ID NO: 133) |
| k-2-42 | GYTLTSYD (SEQ ID NO: 134) | MNPNSGNT (SEQ ID NO: 135) | ARGRSIINHYYGLDV (SEQ ID NO: 136) |
| 1R2kr30 | DFIFNNYN (SEQ ID NO: 137) | IDTSTYTT (SEQ ID NO: 138) | ARDRYGSSYWGATISTLWT (SEQ ID NO: 139) |
| K1 | GYIFTDYW (SEQ ID NO: 140) | IYPGDSET (SEQ ID NO: 141) | ARHGRGYCGGGSCQGTLIDN (SEQ ID NO: 142) |
| L1 | GYIFTDYW (SEQ ID NO: 143) | IYPGDSET (SEQ ID NO: 144) | ARHGRGYCGGGSCQGTLIDN (SEQ ID NO: 145) |
| k-2-32 | GYTLTSYD (SEQ ID NO: 146) | MNPNSGNT (SEQ ID NO: 147) | ARGRSIINHYYGLDV (SEQ ID NO: 148) |
| L-8.2 | GYIFTDYW (SEQ ID NO: 149) | IYPGDSET (SEQ ID NO: 150) | ARHGRGYCGGGSCQGTLIDN (SEQ ID NO: 151) |
| L-8.6 | GYIFTDYW (SEQ ID NO: 152) | IYPGDSET (SEQ ID NO: 153) | ARHGRGYCGGGSCQGTLIDN (SEQ ID NO: 154) |
| L-8.17 | GYIFTDYW (SEQ ID NO: 155) | IYPGDSET (SEQ ID NO: 156) | ARHGRGYCGGGSCQGTLIDN (SEQ ID NO: 157) |

TABLE 2

CDR sequences of Toso antibodies-light chain

| Clone | CDR1 | CDR2 | CDR3 |
|---|---|---|---|
| 3kr7 | QSVGTS (SEQ ID NO: 158) | DAS (SEQ ID NO: 159) | QQRSNGPPSWT (SEQ ID NO: 160) |
| k-2-5 | QSVSSN (SEQ ID NO: 161) | GAS (SEQ ID NO: 162) | QQYNNWPYT (SEQ ID NO: 163) |
| 5/7k5 | QSVSSN (SEQ ID NO: 164) | GAS (SEQ ID NO: 165) | QQYNNWPYT (SEQ ID NO: 166) |

TABLE 2-continued

CDR sequences of Toso antibodies-light chain

| Clone | CDR1 | CDR2 | CDR3 |
| --- | --- | --- | --- |
| 5/7k1 | QSVFSSSYSEDY (SEQ ID NO: 167) | WAS (SEQ ID NO: 168) | QYYITPIT (SEQ ID NO: 169) |
| 5/7k6 | QSVGTS (SEQ ID NO: 170) | DAS (SEQ ID NO: 171) | QQRSTGLRVGR (SEQ ID NO: 172) |
| 5/15kL24 | QSVSSSY (SEQ ID NO: 173) | GAS (SEQ ID NO: 174) | QQYGSSPWT (SEQ ID NO: 175) |
| 5/15kL26 | QSVRSY (SEQ ID NO: 176) | DAT (SEQ ID NO: 177) | QQRNNWPLT (SEQ ID NO: 178) |
| 5/15kL30 | QSVSSY (SEQ ID NO: 179) | DAS (SEQ ID NO: 180) | QQRSNWPPYS (SEQ ID NO: 181) |
| k-4.15 | QRVNTGY (SEQ ID NO: 182) | GAS (SEQ ID NO: 183) | QQHGTSPYT (SEQ ID NO: 184) |
| k-4.16 | QDITHS (SEQ ID NO: 185) | DAS (SEQ ID NO: 186) | QQYDNVPIT (SEQ ID NO: 187) |
| k-4.18 | QNVLYNSNKKNY (SEQ ID NO: 188) | WAS (SEQ ID NO: 189) | QQYYGTPLT (SEQ ID NO: 190) |
| k-4.20 | QRLVYSDGNTY (SEQ ID NO: 191) | KVS (SEQ ID NO: 192) | MQSSTDWPWT (SEQ ID NO: 193) |
| k-4.17 | RSVLYTSTNRYL (SEQ ID NO: 194) | WAS (SEQ ID NO: 195) | QQYYNPPVYT (SEQ ID NO: 196) |
| L-1-13 | SGHSSYAI (SEQ ID NO: 197) | LNSDGSH (SEQ ID NO: 198) | QTWGTGIHWV (SEQ ID NO: 199) |
| 1R2kr3 | QSVSDY (SEQ ID NO: 200) | AAS (SEQ ID NO: 201) | XQSYTTAYT (SEQ ID NO: 202) |
| K3-22 | QSVSDY (SEQ ID NO: 203) | AAS (SEQ ID NO: 204) | QQSYTTAYT (SEQ ID NO: 205) |
| k-2-48 | QSVSSY (SEQ ID NO: 206) | DAS (SEQ ID NO: 207) | QQRSNWPWT (SEQ ID NO: 208) |
| K3-24 | QSVGTS (SEQ ID NO: 209) | DAS (SEQ ID NO: 210) | QQRSNGPPSWT (SEQ ID NO: 211) |
| 5/15L28 | QSISSY (SEQ ID NO: 212) | AAS (SEQ ID NO: 213) | QQSYSTLSL (SEQ ID NO: 214) |
| 5/15kL19 | QSVFSSSYSEDY (SEQ ID NO: 215) | WAS (SEQ ID NO: 216) | QQYYITPIT (SEQ ID NO: 217) |
| k-5.10 | QSLVHSDGNTY (SEQ ID NO: 218) | KIS (SEQ ID NO: 219) | CKLHNFLTL (SEQ ID NO: 220) |
| k-2-42 | QSISNY (SEQ ID NO: 221) | AAS (SEQ ID NO: 222) | QQSYSTPET (SEQ ID NO: 223) |
| 1R2kr30 | QSISSY (SEQ ID NO: 224) | AAS (SEQ ID NO: 225) | QQSYSTPCT (SEQ ID NO: 226) |
| K1 | QSVFSSSYSEDY (SEQ ID NO: 227) | WAS (SEQ ID NO: 228) | QQYYITPIT (SEQ ID NO: 229) |
| L1 | SLRTYY (SEQ ID NO: 230) | AKT (SEQ ID NO: 231) | NSRDSSDNLW (SEQ ID NO: 232) |
| k-2-32 | QDISNY (SEQ ID NO: 233) | DAS (SEQ ID NO: 234) | QQYDNLPPGSP (SEQ ID NO: 235) |
| L-8.2 | SLRTYY (SEQ ID NO: 236) | AKN (SEQ ID NO: 237) | NSRDSSDNLW (SEQ ID NO: 238) |
| L-8.6 | SLRTYY (SEQ ID NO: 239) | AKT (SEQ ID NO: 240) | NSRDSSDNLW (SEQ ID NO: 241) |

TABLE 2-continued

CDR sequences of Toso antibodies-light chain

| Clone | CDR1 | CDR2 | CDR3 |
|---|---|---|---|
| L-8.17 | SLRTYY (SEQ ID NO: 242) | AKN (SEQ ID NO: 243) | NSRDSSDNLW (SEQ ID NO: 244) |

In further embodiments, Toso antibodies of the invention comprise variants of the CDR sequences as provided in FIG. 1. In general, variants can include any number of modifications, as long as the function of the protein is still present, as described herein. That is, in the case of amino acid variants generated with the CDRs of any of the antibodies comprising sequences as provided in FIG. 1, for example, the antibody should still specifically bind to Toso or a ligand of Toso. Similarly, if amino acid variants are generated with the Fc region, for example, the variant antibodies should maintain the required receptor binding functions for the particular application or indication of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications, with from 1-2, 1-3 and 1-4 also finding use in many embodiments.

In some embodiments, one or more amino acid modifications are made in one or more of the CDRs of the Toso antibodies of the invention as provided in FIG. 1 and Tables 1 and 2. In general, only 1 or 2 or 3-amino acids are substituted in any single CDR, and generally no more than from 4, 5, 6, 7, 8 9 or 10 changes are made within a set of CDRs. However, it should be appreciated that any combination of no substitutions, 1, 2 or 3 substitutions in any CDR for a particular antibody can be independently and optionally combined with any other substitution.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be done to increase the binding affinity of the antibody for the antigen by at least about 10% to 50-100-150% or more, or from 1 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation by variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155: 1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of antibodies 3kr7, k-2-5, 5/7k5, 5/7k1, 5/7k6, 5/15kL24, 5/15kL26, 5/15kL30, k-4.15, k-4.16, k-4.18, k-4.20, k-4.17, L-1-13, 1R2kr3, K3-22, k-2-48, K3-24, 5/15L28, 5/15kL19, k-5.10, k-2-42, 1R2kr30, K1, L1, k-2-32, L-8.2, L-8.6, L-8.17, for which sequences of the heavy and light chains are provided in FIG. 1. In addition, amino acid modifications can also independently and optionally be made in any region outside the CDRs, including framework and constant regions.

In some embodiments, the Toso antibodies (also referred to herein as "anti-Toso" or "anti-Toso antibodies") of the invention are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in US 2004/013210, US 2005/0054832, US 2006/0024298, US 2006/0121032, US 2006/0235208, US 2007/0148170, U.S. Pat. No. 6,737,056, 7,670, 600, 6,086,875 all of which are expressly incorporated by reference in their entirety, and in particular for specific amino acid substitutions that increase binding to Fc receptors.

In further aspects, Toso antibodies of the invention comprise any of the full length heavy or light chain sequences provided in FIG. 1. In further embodiments, Toso antibodies of the invention comprise sequences with a sequence identity of about 70%, 75%, 80%, 85%, 90%, 91%, 92%, 93%, 94%, 95%, 96%, 97%, 98%, 99% and 100% identity to any of the full length heavy or light chain sequences provided in FIG. 1.

In still further aspects, Toso antibodies of the invention comprise consensus sequences that encompass CDR sequences as provided in FIG. 1 and Tables 1 and 2. Such consensus sequences can be identified through alignments of the CDR sequences and through the use of tools available on public databases.

In exemplary embodiments, Toso antibodies of the invention comprise a heavy chain CDR1 comprising the following consensus sequence: G-X1-TFS-X2-Y-X3, wherein X1 is F, D or Y, X2 is N, D or S, and X3 is A, G, W or N.

In further embodiments, Toso antibodies of the invention comprise a heavy chain CDR2 comprising the following consensus sequence: I-X1-PSG-X2-T-X3, wherein X1 is S, D, or Y, X2 is G or D, and X3 is T or P.

In still further embodiments, Toso antibodies of the invention comprise a light chain CDR1 comprising the following consensus sequence: Q-S-X1-S-X2-Y, wherein X1 is V or I, and X2 is S, D or N.

In still further embodiments, Toso antibodies of the invention comprise a light chain CDR3 comprising the following consensus sequence: QQ-X1-Y-X2-TP-X3-T, wherein X1 is Y, R or S, X2 is N, G, T, S or I, and X3 is L, I, E, or C.

As will be appreciated, although methods are known in the art for identifying antibodies to a particular protein, not all antibodies identified in such methods will bind to the protein of interest. Thus, one aspect of the present invention is the identification of antibodies that bind to Toso as distinguished from antibodies that do not bind to Toso—see for example the heavy and light chain sequences of the antibodies of FIG. 1, which are from antibodies that do bind to Toso, as opposed to the heavy and light chain sequences of the antibodies in FIG. 2, which do not bind to Toso.

In further aspects, the present invention provides an expression vector encoding an antibody or protein according to any of the sequences described herein and in accordance with any of the sequences provided in FIG. 1.

In still further aspects, the present invention provides a method of making an antibody or protein according to any of the sequences described herein and in accordance with any of the sequences provided in FIG. 1, the method comprising providing a cell comprising a nucleic acid encoding that antibody or protein, where the cell is cultured under conditions suitable for expression of the antibody or protein.

In still further aspects, the present invention provides a method of treating a Toso-associated disease, the method comprising treating a subject in need thereof with an antibody or protein according to any of the sequences described herein and in accordance with any of the sequences provided in FIG. 1.

In yet further aspects, the antibodies of the invention find use in a variety of applications, including diagnosis of Toso-related diseases and treatment thereof.

Additional Modifications to Toso Antibodies

In addition to any of the modifications and variants outlined above, other modifications can be made. For example, the molecules may be stabilized by the incorporation of disulphide bridges linking the VH and VL domains (Reiter et al., 1996, Nature Biotech. 14:1239-1245, entirely incorporated by reference for all purposes and in particular for all teachings regarding modifications of molecules, including antibodies). In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Another type of covalent modification is alterations in glycosylation. In another embodiment, the antibodies disclosed herein can be modified to include one or more engineered glycoforms. By "engineered glycoform" as used herein is meant a carbohydrate composition that is covalently attached to the antibody, wherein said carbohydrate composition differs chemically from that of a parent antibody. Engineered glycoforms may be useful for a variety of purposes, including but not limited to enhancing or reducing effector function.

Engineered glycoforms may be generated by a variety of methods known in the art (Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (Potelligent® technology [Biowa, Inc., Princeton, N.J.]; GlycoMAb® glycosylation engineering technology [Glycart Biotechnology AG, Zurich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example 20090317869, hereby incorporated by reference in its entirety. Engineered glycoform typically refers to the different carbohydrate or oligosaccharide; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various non proteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

III. Methods of Modulating Toso Activity

In one aspect, the present invention is directed to methods of modulating Toso activity. In one embodiment, methods of modulating Toso activity comprise inhibiting Toso activity. In other embodiments, methods of modulating Toso activity comprise increasing Toso activity.

In some embodiments, methods of the present invention involve directly modulating Toso activity. In an exemplary embodiment, such methods include applying an agent that binds to Toso, such as an antibody.

In further embodiments, Toso activity is modulated by a combination of mechanisms, for example by administering a composition comprising an agent that binds to Toso in combination with a composition comprising an agent that binds to cognate ligands of Toso or with a second agent that binds to Toso. In an exemplary embodiment, such a combination may include without limitation a Toso antibody and a soluble Toso protein, such as the soluble Toso protein described in U.S. Ser. No. 13/831,031, filed on Mar. 14, 2013, which is hereby incorporated by reference in its entirety for all purposes and in particular for any disclosure, claims, figures, or other teachings related to a soluble Toso protein.

As will be appreciated, methods of modulating Toso activity can include the use of any of the compositions described herein in any combination, including an antibody comprising any one or more of SEQ ID NOs. 1-62 as well as any variants or modifications thereof as described herein.

V. Methods of Treating Disorders

In one aspect and in accordance with any of the above, the present invention provides methods of treating disorders by treating subjects in need thereof with a composition that modulates Toso activity, where in preferred embodiments that composition includes one or more Toso antibodies.

In a specific embodiment and in accordance with any of the above, the present invention provides methods of treating disorders by treating subjects in need thereof with a composition that includes a Toso antibody. Without being limited by theory, one potential mechanism by which the Toso antibody is an effective treatment for these disorders is through modulating Toso activity. In certain embodiments, methods of treating disorders in accordance with the present invention includes administering a therapeutically effective amount of any of the Toso antibodies described herein, including antibodies comprising any one or more of SEQ ID NOs: 1-62 or any variants thereof. In further embodiments, the soluble Toso proteins used to treat disorders, including diabetes, multiple sclerosis, asthma, and cancer include an antibody comprising a heavy or light chain sequence with about 70%, 75%, 80%, 85%, 90%, 91%, 92%, 93%, 94%, 95%, 96%, 97%, 98%, 99% identity to any one of SEQ ID NOs: 1-28. Such antibodies may further be modified in accordance with the methods described herein, including chemical modifications, for the treatment of any of the disorders described herein.

In further aspects, the present invention is directed to methods of treating disorders and diseases by administering a Toso antibody or variant thereof to a subject. Antibodies of the invention can be used to treat subjects suffering from without limitation: an autoimmune disorder (including without limitation Type 1 diabetes, multiple sclerosis, or rheumatoid arthritis), Type 2 diabetes, asthma, allergy chronic obstructive pulmonary disease ("COPD"), hyper-IgM syndrome, lupus, cancer, or a neutrophilia-associated disorder (including without limitation neutropenia, severe congenital neutropenia, cyclical neutropenia, antibody mediated neutropenia, reticular dysgenesis, leukocyte adhesion deficiency, familiar myeloproliferative disease, chronic myelogenous leukemia, familiar cold urticaria and leukocytosis, and chronic granulomatous disease). As will be appreciated, any of the Toso antibodies described herein, singly or in any combination, can be used to treat any of these disorders or diseases.

As discussed above, in some embodiments, soluble Toso proteins of the invention are used to treat cancer. In further embodiments, methods of treating cancer in accordance with the invention include methods of inhibiting tumor invasion and/or metastasis by modulating Toso activity. In exemplary embodiments, compositions of the invention are used to treat any one of the group of an adenocarcinoma, a leukemia, a lymphoma, a melanoma, a myeloma, a sarcoma or a teratocarcinoma in subjects in need thereof. In further embodiments, compositions of the invention are used to treat subjects suffering from a cancer in one or more of adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid or uterus.

EXAMPLE 1

Human Naïve Phage scFv Library Construction

Peripheral blood mononuclear cells (PBMCs) were obtained from donated and commercially available blood samples. PBMCs were separated using Ficoll-Paque™ PLUS (GE Healthcare). Total RNA was then isolated from the separated PBMCs using Trizol and mRNA was then purified from the Total RNA using Dynabeads® mRNA Purification Kit for mRNA Purification from Total RNA Preps (Ambion).

First strand cDNA synthesis from the mRNA was conducted using SuperScript III First-Strand Synthesis System for RT-PCR (Invitrogen). The cDNA library was pooled and the concentration measured.

Variable kappa-, lambda- and gamma-chain genes were amplified separately using 60-90 ng of cDNA as template and 2.5 µl each of the provided constant and available region DNA primer set 1 (F2000, Progen), 25 µl of 2×terra PCR buffer, 1 µl of terra polymerase mix, at a total volume of 50 µl. PCR conditions: 95° C. for 30 sec (denatureation), 55° C. 1 min (annealing), and 75° C. for 1 min (extension), total 30 cycles. At the beginning of the first cycle, the reaction mixture was incubated at 95° C. for 3 min and at the end of the last cycle incubated at 75° C. for 5 min.

To introduce restriction sites, PCRs were performed in a total of 50 µl containing: 1 µl of the PCR product of variable gene (kappa-, lambda- and gamma-chain genes were used as templates respectively), 2.5 µl each of the provided constant and variable region DNA primer set 2 (F2000, Progen), 25 µl of 2×terra PCR buffer, 1 µl of terra polymerase mix. PCR conditions: 95° C. for 30 sec (denaturation), 57° C. for 1 min (annealing), and 75° C. for 1 min (extension), total 14 cycles. At the beginning of the first cycle, incubation at 95° C. for 3 min and at the end of the last cycle incubation at 75° C. for 5 min. The PCR product was purified using gel DNA extraction kit (Clontech). The purified kappa, lambda and gamma DNA respectively were pooled.

Light chain DNA was cloned into phagemid vector pSEX81 by: digesting 10 µg phagemid vector pSEX81 (Progen) by adding 25 µl of Buffer H, 6 µl of NotI (40 u/µl) and 0.5 µl of RNase A (10 µg) at a total volume of 224 µl·mix and incubating for 8 min at 37° C., then adding 20 µl of MluI (10 u/µl), incubated for 6 minutes at 37° C. Following that, alkaline phosphatase (CIP) was added, and incubation continued for 15 minutes at 37° C. Then, 0.25 µl of 0.5M pH8.0 EDTA was added, followed by incubation for 20 min at 65° C. The mixture was run out on a gel and the gel band containing the MluI/NotI-pSEX81-fragment was cut and extracted using a gel DNA extraction kit. 1.5 µg of the pooled kappa- and the pooled lambda-chain PCR products, respectively were then digested by adding 7.5 µl of buffer H, 0.9 µl of NotI (40 u/µl), incubating for 20 min at 37° C., and then adding 3 µl of MluI (10 u/µl), followed by further incubation for 40 minutes at 37° C. A 1.5% agarose gel was run with the reaction products and the band at 400 bp was cut and purified using a gel DNA extraction kit. The digested vector (pSEX81) and insert (kappa- or lambda-variable chain genes) were ligated using a molar ratio between 1:1 and 1:3. The reaction mixture included 50 ng DNA, 1 U of T4 ligase, ligation buffer and $H_2O$ to a final volume of 15 µl. Overnight incubation at 16° C. was followed by precipitation of the DNA by adding 1/10 volume of 3M sodium acetate, 20 µg glycogen, 2.5× volume of absolute ethanol. Incubation for 1.5 hour at −20° C. was followed by sedimenting of the precipitate by centrifugation for 30 minutes at 13,000 rpm. The pellet was washed with 80% ethanol at least twice, and then the pellet was allowed to dry at room temperature. The dried pellet was resuspended in 2-5 µl H2O.

Heavy chain DNA was then cloned into the pSEX81 vectors containing the light chain DNA by: digesting 10 µg of light chain containing vectors (kappa-pSEX81 and lambda-pSEX81) respectively with 10 µl of HindIII (10 u/µl), 25 µl of Buffer H, 0.5 µl of RNAse A (10 µg) in a total volume 230 µl, incubating for 20 min at 37° C., then, adding 10 µl of NcoI (10 u/µl), then incubating 90 minutes at 37° C. The remaining procedures for digesting the vectors are the same as described above. For digesting the heavy chain insert, 1 µg of the pooled gamma chain PCR products was digested with 7.5 ul of 10× buffer H, 2.7 ul of HindIII (10 u/ul), 4 ul of NcoI (10 u/ul) at a total volume of 75 µl, followed by incubation for 4 hours at 37° C., and then by incubation for 20 min at 65° C. The digested DNA was purified using a gel DNA extraction kit. Ligation and precipitation of the DNA was completed as described above.

Library stocks were created by: 1.5 µl of one ligation reaction was used for the electroporation of 40 µl electrocompetent *E. coli* XL-blue (Stratagene). Each transformation of the ligated DNA library was plated onto SOB-GA agar plates and incubated 30° C. overnight. 6 ml 2×YT-GA medium was added to each plate and the bacteria were scraped into the medium. The cells were pooled and made into glycerol stocks.

EXAMPLE 2

Biopanning of library

An inoculated culture was grown at 37° C. with shaking at 250 rpm until an $A_{600}$ Of 0.1 was reached. M13K07 helper phage was added, and then the culture was incubated for 15 minutes at 37° C. without shaking, then 1 hour at 37° C. with shaking at 250 rpm. Cells were pelleted for 10 min at 1500 g and then resuspended in 400 ml of 2×YT-AK medium. The suspension was grown overnight at 30° C. with shaking at 250 rpm. The culture was spun and phage was then precipitated using a PEG solution. Phage was titerated. Glycerol stocks could be made or the libraries could be used directly for panning.

Two wells in a nunc 96-well plate were coated with 200 µl/well, 100 µg/ml of purified Toso-Fc in PBS; two wells were coated with 200 µl of 100 µg/ml rhIgG Fc (Sino Biological Inc.); 200 µl of 5% milk PBS (MPBS) was added to another 2 wells (without antigen), and the plate was incubated overnight at 4° C.

0.6 ml of $10^{12}$ pfu/ml phages was removed from the naïve libraries to a 1.5 ml tubes, protein G beads were added to the tubes, and then tubes were incubated on a rotary for overnight at 4° C.

The Toso-Fc coated wells were emptied the next morning and washed 3 times with PBST and block with 250 ul of 5% MPBS, followed by incubation for 2 hours at room temperature.

The rhIgG Fc (Sino Biological Inc.) coated wells were emptied. The phage-protein G beads solution was centrifuged and 100 µl supernatant was transferred to each of the two rhIgG Fc coated wells. 100 ug/ml rhIgG Fc, 100 µl/well was added (Sino Biological Inc.), and incubated at room temperature for 1 hour.

The non-protein coated wells were emptied and the phage solution was transferred to non-protein coated wells separately and incubated for 1 hour at room temperature.

The blocking buffer was removed from the Toso-Fc-coated wells and then washed several times with PBST. The 200 µl phage solution was transferred to the Toso-Fc-coated wells and incubated for 1.5 hours at room temperature.

The Toso-Fc-coated wells were emptied and washed several times with PBST. The phage was eluted by adding 200 µl 100 mM triethylamine to each of the two wells follow by 10 minutes of incubation.

The eluted phage was transferred to 2×1.5 ml tubes containing 800 ul of 1M Tris-HCl (pH7.5) to neutralize the pH.

2×10 ul of eluted phage was used to do titration. The remaining eluted phage was used to infect 10 ml fresh TG1 cells ($OD_{600}$=0.4). 200 ul of this sample was spread on a 2×YT agar plate containing 100 ul/ml of ampicillin and 1% glucose, grown overnight at 32° C. The remaining infected cells were incubated at 37° C. with shaking at 250 rpm for 1 hour, following which the volume was increased to 110 ml with 2×YT medium containing 100 ug/ml amp, followed by incubation at 37° C. with shaking at 250 rpm.

M13KO7 helper phages (100 µl of $10^{12}$ pfu) were added to the infected culture and grown at 37° C., also. Kanamycin was added to the culture at a final concentration of 50 µg/ml. This culture was incubated overnight at 37° C., with shaking at 250 rpm for the next round of panning.

Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. An antibody comprising a heavy chain comprising the amino acid sequence of SEQ ID NO: 1 and a light chain comprising the amino acid sequence of SEQ ID NO: 2.

2. An antibody comprising a heavy chain comprising the amino acid sequence of SEQ ID NO: 3 and a light chain comprising the amino acid sequence of SEQ ID NO: 4.

3. An antibody comprising a heavy chain comprising the amino acid sequence of SEQ ID NO: 5 and a light chain comprising the amino acid sequence of SEQ ID) NO: 6.

4. An antibody comprising a heavy chain comprising the amino acid sequence of SEQ ID NO: 7 and a light chain comprising the amino acid sequence of SEQ ID NO: 8.

5. An antibody comprising a heavy chain comprising the amino acid sequence of SEQ ID NO: 9 and a light chain comprising the amino acid sequence of SEQ ID NO: 10.

* * * * *

SEQUENCE LISTING

```
<160> NUMBER OF SEQ ID NOS: 244

<210> SEQ ID NO 1
<211> LENGTH: 134
<212> TYPE: PRT
<213> ORGANISM: Artificial Sequence
<220> FEATURE:
<223> OTHER INFORMATION: Toso-binding variable heavy chain

<400> SEQUENCE: 1

Glu Val Gln Leu Val Gln Ser Gly Gly Gly Leu Val Gln Pro Gly Gly
1               5                   10                  15

Ser Leu Arg Leu Ser Cys Val Ala Ser Asp Phe Ile Phe Asn Asn Tyr
            20                  25                  30

Asn Met Asn Trp Val Arg Gln Ala Pro Gly Lys Gly Leu Glu Trp Leu
        35                  40                  45

Ser Phe Ile Asp Thr Ser Thr Tyr Thr Thr Tyr Tyr Ala Asp Ser Val
    50                  55                  60

Arg Gly Arg Phe Thr Ile Ser Arg Asp Asn Ser Lys Lys Ser Leu Phe
65                  70                  75                  80

Leu Gln Met Asn Thr Leu Thr Asp Asp Asp Thr Ala Val Tyr Phe Cys
                85                  90                  95

Ala Arg Asp Arg Tyr Gly Ser Ser Tyr Trp Gly Gly His Tyr Phe His
            100                 105                 110

Ala Met Asp Val Trp Gly Gln Gly Thr Pro Val Thr Val Ser Ser Ala
        115                 120                 125

Ser Thr Lys Gly Pro Lys
    130

<210> SEQ ID NO 2
<211> LENGTH: 120
<212> TYPE: PRT
<213> ORGANISM: Artificial Sequence
<220> FEATURE:
<223> OTHER INFORMATION: Toso-binding variable light chain

<400> SEQUENCE: 2

Glu Ile Val Leu Thr Gln Ser Pro Ala Thr Leu Ser Ser Ser Pro Gly
1               5                   10                  15

Glu Arg Ala Thr Leu Ser Cys Arg Ala Ser Gln Ser Val Gly Thr Ser
            20                  25                  30

Leu Ala Trp Tyr Gln Gln Ile Pro Gly Gln Ala Pro Ser Leu Leu Ile
        35                  40                  45

His Asp Ala Ser Asn Arg Ala Ser Gly Ile Pro Ala Arg Phe Ser Gly
    50                  55                  60

Ser Gly Ser Gly Thr Asp Phe Thr Leu Thr Ile Asn Ser Leu Glu Pro
65                  70                  75                  80

Glu Asp Phe Ala Val Tyr Tyr Cys Gln Gln Arg Ser Asn Gly Pro Pro
                85                  90                  95
```

```
Ser Trp Thr Phe Gly Gln Gly Thr Lys Val Glu Ile Lys Arg Thr Val
                100                 105                 110

Ala Ala Pro Ser Val Phe Ala Ala
        115                 120

<210> SEQ ID NO 3
<211> LENGTH: 139
<212> TYPE: PRT
<213> ORGANISM: Artificial Sequence
<220> FEATURE:
<223> OTHER INFORMATION: Toso-binding variable heavy chain

<400> SEQUENCE: 3

Ala Gly Ala Ala Gly Ala Val Trp Gly Asp Val His Pro Gly Gly
1               5                   10                  15

Ser Leu Arg Ile Ser Cys Glu Gly Ser Gly Phe Ser Phe Ser Asp Phe
            20                  25                  30

Gly Ile His Trp Val Arg Gln Ala Pro Gly Lys Gly Leu Glu Trp Val
            35                  40                  45

Ala Val Val Arg Tyr Asp Gly Ser Lys Glu Tyr Tyr Ala Asp Ser Val
        50                  55                  60

Lys Gly Arg Phe Thr Ile Ser Arg Asp Asn Ala Arg Asn Thr Val His
65                  70                  75                  80

Leu Glu Leu Asp Ser Leu Arg Ser Glu Asp Thr Ala Val Tyr Phe Cys
                85                  90                  95

Ala Lys Asp Glu Met Ala Arg Trp Ala Tyr Val Asp Trp Leu Pro His
                100                 105                 110

Leu His His Ser Tyr Gly Met Asp Val Trp Gly Gln Gly Thr Thr Val
            115                 120                 125

Ile Val Ser Ser Ala Ser Thr Lys Gly Pro Lys
            130                 135

<210> SEQ ID NO 4
<211> LENGTH: 117
<212> TYPE: PRT
<213> ORGANISM: Artificial Sequence
<220> FEATURE:
<223> OTHER INFORMATION: Toso-binding variable light chain

<400> SEQUENCE: 4

Val Glu Ile Val Leu Thr Gln Ser Pro Ala Thr Leu Ser Val Ser Pro
1               5                   10                  15

Gly Glu Arg Ala Thr Leu Ser Cys Arg Ala Ser Gln Ser Val Ser Ser
            20                  25                  30

Asn Leu Ala Trp Tyr Gln Gln Lys Pro Asp Gln Ala Pro Arg Leu Leu
            35                  40                  45

Ile Tyr Gly Ala Ser Thr Arg Ala Thr Gly Ile Pro Ala Arg Phe Ser
        50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Asn Asn Trp Pro
                85                  90                  95

Tyr Thr Phe Gly Gln Gly Thr Lys Leu Glu Ile Lys Arg Thr Val Ala
                100                 105                 110

Ala Pro Ser Val Phe
        115

<210> SEQ ID NO 5
```

```
<211> LENGTH: 139
<212> TYPE: PRT
<213> ORGANISM: Artificial Sequence
<220> FEATURE:
<223> OTHER INFORMATION: Toso-binding variable heavy chain

<400> SEQUENCE: 5

Ala Gly Ala Ala Gly Ala Val Trp Gly Asp Val Val His Pro Gly Gly
 1               5                  10                  15

Ser Leu Arg Ile Ser Cys Glu Gly Ser Gly Phe Ser Phe Ser Asp Phe
            20                  25                  30

Gly Ile His Trp Val Arg Gln Ala Pro Gly Lys Gly Leu Glu Trp Val
        35                  40                  45

Ala Val Val Arg Tyr Asp Gly Ser Lys Glu Tyr Tyr Ala Asp Ser Val
    50                  55                  60

Lys Gly Arg Phe Thr Ile Ser Arg Asp Asn Ala Arg Asn Thr Val His
65                  70                  75                  80

Leu Glu Leu Asp Ser Leu Arg Ser Glu Asp Thr Ala Val Tyr Phe Cys
                85                  90                  95

Ala Lys Asp Glu Met Ala Arg Trp Ala Tyr Val Asp Trp Leu Pro His
            100                 105                 110

Leu His His Ser Tyr Gly Met Asp Val Trp Gly Gln Gly Thr Thr Val
        115                 120                 125

Ile Val Ser Ser Ala Ser Thr Lys Gly Pro Lys
    130                 135

<210> SEQ ID NO 6
<211> LENGTH: 116
<212> TYPE: PRT
<213> ORGANISM: Artificial Sequence
<220> FEATURE:
<223> OTHER INFORMATION: Toso-binding variable light chain

<400> SEQUENCE: 6

Val Glu Ile Val Leu Thr Gln Ser Pro Ala Thr Leu Ser Val Ser Pro
 1               5                  10                  15

Gly Glu Arg Ala Thr Leu Ser Cys Arg Ala Ser Gln Ser Val Ser Ser
            20                  25                  30

Asn Leu Ala Trp Tyr Gln Gln Lys Pro Asp Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Asn Asn Trp Pro
                85                  90                  95

Tyr Thr Phe Gly Gln Gly Thr Lys Leu Glu Ile Asn Glu Leu Trp Leu
            100                 105                 110

His His Leu Ser
        115

<210> SEQ ID NO 7
<211> LENGTH: 133
<212> TYPE: PRT
<213> ORGANISM: Artificial Sequence
<220> FEATURE:
<223> OTHER INFORMATION: Toso-binding variable heavy chain

<400> SEQUENCE: 7
```

```
Gln Val Gln Leu Val Gln Ser Gly Gly Gly Leu Phe Gln Pro Gly
1               5                   10                  15

Ser Leu Arg Leu Ser Cys Ala Ala Ser Gly Phe Thr Phe Ser Asn His
            20                  25                  30

Trp Met His Trp Val Arg Gln Ala Pro Gly Lys Gly Leu Val Trp Val
            35                  40                  45

Ser Arg Ile Lys Arg Asp Ala Thr Ser Thr Thr Tyr Gly Asp Ser Val
50                  55                  60

Lys Gly Arg Phe Thr Ile Ser Arg Asp Asn Ala Lys Asn Thr Leu Tyr
65                  70                  75                  80

Leu Gln Met Lys Ser Leu Arg Val Asp Asp Thr Ala Val Tyr Tyr Cys
                85                  90                  95

Val Arg Glu Gly Gly Tyr Thr Tyr Gly Gly Val Tyr Tyr Asn Gly
            100                 105                 110

Met Asp Val Trp Gly Gln Gly Thr Thr Val Thr Val Ser Ala Ala Ser
            115                 120                 125

Thr Lys Gly Pro Lys
        130
```

<210> SEQ ID NO 8
<211> LENGTH: 124
<212> TYPE: PRT
<213> ORGANISM: Artificial Sequence
<220> FEATURE:
<223> OTHER INFORMATION: Toso-binding variable light chain

<400> SEQUENCE: 8

```
Asp Ile Glu Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Ser Ser
            20                  25                  30

Ser Tyr Ser Glu Asp Tyr Leu Ala Trp Tyr Gln Gln Lys Pro Gly Gln
            35                  40                  45

Ala Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Leu Gln Val Glu Asp Val Ala Val Tyr Tyr Cys Gln Gln
                85                  90                  95

Tyr Tyr Ile Thr Pro Ile Thr Phe Gly Gln Gly Thr Arg Leu Glu Ile
            100                 105                 110

Lys Arg Thr Val Ala Ala His Met Ser Ser Arg Pro
            115                 120
```

<210> SEQ ID NO 9
<211> LENGTH: 134
<212> TYPE: PRT
<213> ORGANISM: Artificial Sequence
<220> FEATURE:
<223> OTHER INFORMATION: Toso-binding variable heavy chain

<400> SEQUENCE: 9

```
Glu Val Gln Leu Val Gln Ser Gly Gly Gly Leu Val Gln Pro Gly Gly
1               5                   10                  15

Ser Leu Arg Leu Ser Cys Val Ala Ser Asp Phe Ile Phe Asn Asn Tyr
            20                  25                  30

Asn Met Asn Trp Val Arg Gln Ala Pro Gly Lys Gly Leu Glu Trp Leu
            35                  40                  45
```

-continued

Ser Phe Ile Asp Thr Ser Thr Tyr Thr Thr Tyr Tyr Ala Asp Ser Val
            50                  55                  60

Arg Gly Arg Phe Thr Ile Ser Arg Asp Asn Ser Lys Lys Ser Leu Phe
 65                  70                  75                  80

Leu Gln Met Asn Thr Leu Thr Asp Asp Thr Ala Val Tyr Phe Cys
                    85                  90                  95

Ala Arg Asp Arg Tyr Gly Ser Ser Tyr Trp Gly Gly His Tyr Phe His
            100                 105                 110

Ala Met Asp Val Trp Gly Gln Gly Thr Pro Val Thr Val Ser Ser Ala
            115                 120                 125

Ser Thr Lys Gly Pro Lys
        130

<210> SEQ ID NO 10
<211> LENGTH: 119
<212> TYPE: PRT
<213> ORGANISM: Artificial Sequence
<220> FEATURE:
<223> OTHER INFORMATION: Toso-binding variable light chain

<400> SEQUENCE: 10

Val Glu Ile Val Leu Thr Gln Ser Pro Ala Thr Leu Ser Ser Ser Pro
 1               5                  10                  15

Gly Glu Arg Ala Thr Leu Ser Cys Arg Ala Ser Gln Ser Val Gly Thr
            20                  25                  30

Ser Leu Ala Trp Tyr Gln Gln Ile Pro Gly Gln Ala Pro Ser Leu Leu
        35                  40                  45

Ile His Asp Ala Ser Asn Arg Ala Ser Gly Ile Pro Ala Arg Phe Ser
    50                  55                  60

Gly Ser Gly Ser Gly Thr Asp Phe Thr Leu Thr Ile Asn Ser Leu Glu
 65                  70                  75                  80

Pro Glu Asp Phe Ala Val Tyr Tyr Cys Gln Gln Arg Ser Thr Gly Leu
                    85                  90                  95

Arg Val Gly Arg Ser Ala Lys Gly Pro Arg Trp Lys Ser Asn Gly Thr
            100                 105                 110

Val Ala Ala Pro Ser Val Phe
        115

<210> SEQ ID NO 11
<211> LENGTH: 128
<212> TYPE: PRT
<213> ORGANISM: Artificial Sequence
<220> FEATURE:
<223> OTHER INFORMATION: Toso-binding variable heavy chain

<400> SEQUENCE: 11

Gly Gly Ala Ala Val Glu Ser Gly Gly Gly Leu Val Gln Pro Gly Gly
 1               5                  10                  15

Ser Leu Arg Leu Ser Cys Val Ala Ser Gly Phe Thr Phe Ser Ser Tyr
            20                  25                  30

Asp Met Ile Trp Val Arg Gln Ala Pro Gly Lys Gly Leu Glu Trp Val
            35                  40                  45

Ser Ala Ile Ser Gly Ser Gly Ser Pro Tyr Tyr Ala Asp Ser Val
        50                  55                  60

Arg Gly Arg Phe Thr Ile Ser Arg Asp Asn Ser Lys Gly Thr Leu Phe
 65                  70                  75                  80

Leu Gln Met Asn Ser Leu Arg Ala Glu Asp Thr Ala Val Tyr Phe Cys

```
                85                  90                  95
Ala Lys Pro Tyr Thr Ser Gly Trp Tyr Val Gly Cys Asp Ser Trp Gly
            100                 105                 110
Gln Gly Thr Leu Val Thr Val Ser Ser Ala Ser Thr Lys Gly Pro Lys
            115                 120                 125
```

<210> SEQ ID NO 12
<211> LENGTH: 118
<212> TYPE: PRT
<213> ORGANISM: Artificial Sequence
<220> FEATURE:
<223> OTHER INFORMATION: Toso-binding variable light chain

<400> SEQUENCE: 12

```
Val Glu Ile Val Leu Thr Gln Ser Pro Arg Thr Leu Ser Leu Ser Pro
1               5                   10                  15
Gly Glu Arg Ala Thr Leu Ser Cys Arg Ala Ser Gln Ser Val Ser Ser
                20                  25                  30
Ser Tyr Leu Ala Trp Tyr Gln Gln Arg Pro Gly Gln Ala Pro Arg Leu
            35                  40                  45
Leu Ile Tyr Gly Ala Ser Ser Arg Ala Thr Gly Ile Pro Asp Arg Phe
        50                  55                  60
Ser Gly Ser Gly Ser Gly Thr Asp Phe Thr Leu Thr Ile Ser Arg Leu
65                  70                  75                  80
Glu Pro Glu Asp Phe Ala Val Tyr Tyr Cys Gln Gln Tyr Gly Ser Ser
                85                  90                  95
Pro Trp Thr Phe Gly Gln Gly Thr Lys Val Glu Ile Lys Arg Asp Cys
            100                 105                 110
Gly Cys Thr Ile Cys Leu
        115
```

<210> SEQ ID NO 13
<211> LENGTH: 132
<212> TYPE: PRT
<213> ORGANISM: Artificial Sequence
<220> FEATURE:
<223> OTHER INFORMATION: Toso-binding variable heavy chain

<400> SEQUENCE: 13

```
Gly Gly Ala Ala Val Glu Ser Gly Gly Leu Val Gln Pro Gly Gly
1               5                   10                  15
Ser Leu Arg Leu Ser Cys Ala Ala Ser Gly Phe Thr Phe Ser Asp Cys
                20                  25                  30
Ala Met Gly Trp Val Arg Gln Ala Pro Gly Lys Gly Pro Glu Trp Val
            35                  40                  45
Ala Ala Ile Ser Gly Ser Gly Leu Ser Thr Tyr Tyr Thr Gly Ser Val
        50                  55                  60
Lys Gly Arg Phe Ser Ile Ser Arg Asp Asn Ser Lys Ser Thr Met Phe
65                  70                  75                  80
Leu Gln Met Asp Ser Leu Ser Ala Gly Asp Thr Ala Leu Tyr Tyr Cys
                85                  90                  95
Thr Lys Ala Pro Trp Asp Tyr Tyr Gly Ser Gly Asn Thr Asp His Phe
            100                 105                 110
Asp His Trp Gly Gln Gly Thr Leu Val Thr Val Ser Ser Ala Ser Thr
            115                 120                 125
Lys Gly Pro Lys
        130
```

-continued

```
<210> SEQ ID NO 14
<211> LENGTH: 116
<212> TYPE: PRT
<213> ORGANISM: Artificial Sequence
<220> FEATURE:
<223> OTHER INFORMATION: Toso-binding variable light chain

<400> SEQUENCE: 14

Val Glu Ile Val Leu Thr Gln Ser Pro Ala Thr Leu Ser Leu Ser Pro
1               5                   10                  15

Gly Glu Arg Ala Thr Leu Ser Cys Arg Ala Ser Gln Ser Val Arg Ser
                20                  25                  30

Tyr Leu Ala Trp Tyr Arg Gln Arg Pro Gly Gln Ala Pro Arg Leu Leu
            35                  40                  45

Ile Tyr Asp Ala Thr Tyr Arg Ala Ala Gly Ile Pro Ala Arg Ile Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Asn Asn Trp Pro
                85                  90                  95

Leu Thr Phe Gly Gly Gly Thr Lys Val Glu Ile Arg Arg Leu Trp Leu
            100                 105                 110

His His Leu Ser
        115

<210> SEQ ID NO 15
<211> LENGTH: 123
<212> TYPE: PRT
<213> ORGANISM: Artificial Sequence
<220> FEATURE:
<223> OTHER INFORMATION: Toso-binding variable heavy chain

<400> SEQUENCE: 15

Gly Gly Ala Ala Val Gly Val Trp Gly Arg Leu Gly Thr Ala Trp Gly
1               5                   10                  15

Ser Leu Arg Leu Ser Cys Thr Ala Thr Gly Phe Thr Phe Ser Ser His
                20                  25                  30

Ala Met Ser Trp Val Arg Gln Ala Pro Gly Lys Gly Pro Glu Trp Val
            35                  40                  45

Ser Ala Ile Ser Gly Arg Gly Ser Ser Ile Asn Tyr Ala Asp Ser Val
50                  55                  60

Lys Gly Leu Phe Thr Val Ser Arg Asp Asn Phe Lys Asn Met Leu Ser
65                  70                  75                  80

Leu Gln Met Asn Ser Leu Arg Ala Asp Asp Thr Ala Val Tyr Tyr Cys
                85                  90                  95

Ala Lys Gly Leu Ala Asp Phe Asp Tyr Trp Gly Gln Gly Thr Leu Val
            100                 105                 110

Thr Val Ser Ser Ala Ser Thr Lys Gly Pro Lys
        115                 120

<210> SEQ ID NO 16
<211> LENGTH: 118
<212> TYPE: PRT
<213> ORGANISM: Artificial Sequence
<220> FEATURE:
<223> OTHER INFORMATION: Toso-binding variable light chain

<400> SEQUENCE: 16

Val Glu Ile Val Met Thr Gln Ser Pro Ala Thr Leu Ser Leu Ser Pro
```

```
            1               5                  10                 15
Gly Glu Arg Ala Thr Leu Ser Cys Arg Ala Ser Gln Ser Val Ser Ser
                20                  25                 30

Tyr Leu Ala Trp Tyr Gln Gln Lys Pro Gly Gln Ala Pro Arg Leu Leu
            35                  40                 45

Ile Tyr Asp Ala Ser Asn Arg Ala Thr Gly Ile Pro Ala Arg Phe Ser
        50                  55                 60

Gly Ser Gly Ser Gly Thr Asp Phe Thr Leu Thr Ile Ser Ser Leu Glu
65                  70                  75                      80

Pro Glu Asp Phe Ala Val Tyr Tyr Cys Gln Gln Arg Ser Asn Trp Pro
                85                  90                 95

Pro Tyr Ser Phe Gly Gln Gly Thr Lys Leu Glu Ile Lys Arg Lys Leu
                100                 105                110

Trp Leu His His Leu Ser
        115
```

<210> SEQ ID NO 17
<211> LENGTH: 126
<212> TYPE: PRT
<213> ORGANISM: Artificial Sequence
<220> FEATURE:
<223> OTHER INFORMATION: Toso-binding variable heavy chain

<400> SEQUENCE: 17

```
            1               5                  10                 15
Gly Gly Ala Ala Val Glu Ser Gly Gly Glu Leu Arg Lys Pro Gly Glu

Ser Leu Lys Ile Ser Cys Gln Thr Ser Gly Tyr Asp Phe Ala Asn Phe
                20                  25                 30

Trp Ile Gly Trp Val Arg Gln Met Pro Gly Lys Gly Leu Glu Trp Val
            35                  40                 45

Gly Ile Ile Tyr Pro Asp Asp Ser Asp Val Asn Tyr Ser Pro Gly Phe
        50                  55                 60

Gln Gly His Val Ala Ile Ser Ala Asp Lys Ser Ile Ser Thr Val Tyr
65                  70                  75                      80

Leu Glu Trp Ser Ser Leu Lys Ala Ser Asp Ser Gly Ile Tyr Tyr Cys
                85                  90                 95

Thr Arg Arg Tyr Ser Gly Ala Gln Leu Gly Val Asp Ser Trp Gly Leu
                100                 105                110

Gly Thr Leu Val Thr Val Ser Ser Ala Ser Thr Arg Ala Gln
        115                 120                 125
```

<210> SEQ ID NO 18
<211> LENGTH: 118
<212> TYPE: PRT
<213> ORGANISM: Artificial Sequence
<220> FEATURE:
<223> OTHER INFORMATION: Toso-binding variable light chain
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 18

Arg Arg Ile Val Leu Thr Gln Ser Pro Asp Thr Leu Ser Leu Ser Pro
1               5                   10                  15

Gly Glu Arg Val Thr Leu Ser Cys Arg Ala Ser Gln Val Asn Thr
            20                  25                  30

Gly Tyr Leu Ala Xaa Tyr Gln Gln Lys Pro Gly Gln Ala Pro Arg Leu
            35                  40                  45

Leu Ile Tyr Gly Ala Ser Arg Arg Ala Thr Gly Val Pro Asp Arg Phe
50                  55                  60

Ser Gly Ser Gly Ser Gly Thr Asp Phe Thr Leu Ser Ile Ser Arg Val
65                  70                  75                  80

Gly Pro Asp Asp Phe Ala Ile Tyr Tyr Cys Gln Gln His Gly Thr Ser
            85                  90                  95

Pro Tyr Thr Phe Gly Gln Gly Xaa Arg Leu Xaa Ile Lys Arg Thr Val
            100                 105                 110

Ala Ala Thr Ile Cys Leu
            115

<210> SEQ ID NO 19
<211> LENGTH: 129
<212> TYPE: PRT
<213> ORGANISM: Artificial Sequence
<220> FEATURE:
<223> OTHER INFORMATION: Toso-binding variable heavy chain
<220> FEATURE:
<221> NAME/KEY: misc_feature
<222> LOCATION: (84)..(84)
<223> OTHER INFORMATION: Xaa can be any naturally occurring amino acid

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Val Tyr Asn Gly Asn Thr Asn Tyr Ala Gln Asn Leu
50                  55                  60

Gln Gly Arg Val Thr Met Thr Thr Asp Thr Ser Thr Ser Thr Ala Tyr
65                  70                  75                  80

Met Glu Leu Xaa Ser Leu Arg Ser Asp Asp Thr Ala Val Tyr Tyr Cys
            85                  90                  95

Ala Arg Asp Gly Leu Arg Trp Leu Arg Pro Thr Gly Met Asp Val Trp
            100                 105                 110

Gly Gln Gly Thr Thr Val Thr Val Ser Ser Ala Ser Thr Lys Gly Pro
            115                 120                 125

Lys

<210> SEQ ID NO 20
<211> LENGTH: 115
<212> TYPE: PRT
<213> ORGANISM: Artificial Sequence
<220> FEATURE:
<223> OTHER INFORMATION: Toso-binding variable light chain
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

```
<220> FEATURE:
<221> NAME/KEY: misc_feature
<222> LOCATION: (83)..(83)
<223> OTHER INFORMATION: Xaa can be any naturally occurring amino acid

<400> SEQUENCE: 20
```

| | | | | | | | | | | | | | | | |
|---|---|---|---|---|---|---|---|---|---|---|---|---|---|---|---|
| Val | Asp | Ile | Glu | Met | Thr | Gln | Ser | Pro | Ser | Ser | Leu | Ser | Ala | Ser | Val |
| 1 | | | | 5 | | | | | 10 | | | | | 15 | |
| Gly | Asp | Arg | Val | Thr | Ile | Thr | Cys | Gln | Ala | Ser | Gln | Asp | Ile | Thr | His |
| | | | 20 | | | | | 25 | | | | | 30 | | |
| Ser | Leu | Asn | Trp | Phe | Gln | Gln | Lys | Pro | Gly | Lys | Ala | Pro | Lys | Leu | Leu |
| | | | 35 | | | | | 40 | | | | | 45 | | |
| Ile | Tyr | Asp | Ala | Ser | Asn | Leu | Glu | Thr | Gly | Val | Pro | Ser | Arg | Phe | Ser |
| | | | 50 | | | | | 55 | | | | | 60 | | |
| Gly | Xaa | Gly | Ser | Gly | Thr | Asp | Phe | Thr | Phe | Thr | Ile | Xaa | Ser | Leu | Gln |
| 65 | | | | | 70 | | | | | 75 | | | | | 80 |
| Pro | Glu | Xaa | Phe | Ala | Thr | Tyr | Tyr | Cys | Gln | Gln | Tyr | Asp | Asn | Val | Pro |
| | | | | 85 | | | | | 90 | | | | | 95 | |
| Ile | Thr | Phe | Gly | Gln | Gly | Thr | Arg | Leu | Glu | Ile | Lys | Arg | Thr | Val | Ala |
| | | | 100 | | | | | 105 | | | | | 110 | | |
| His | Leu | Ser | | | | | | | | | | | | | |
| | | 115 | | | | | | | | | | | | | |

```
<210> SEQ ID NO 21
<211> LENGTH: 130
<212> TYPE: PRT
<213> ORGANISM: Artificial Sequence
<220> FEATURE:
<223> OTHER INFORMATION: Toso-binding variable heavy chain

<400> SEQUENCE: 21
```

| | | | | | | | | | | | | | | | |
|---|---|---|---|---|---|---|---|---|---|---|---|---|---|---|---|
| Ala | Gly | Ala | Leu | Val | Gln | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ser | Ala | Ser | Gly | Phe | Thr | Phe | Ser | Ser | Tyr |
| | | | 20 | | | | | 25 | | | | | 30 | | |
| Ala | Met | His | Trp | Val | Arg | Gln | Ala | Pro | Gly | Lys | Gly | Leu | Glu | Tyr | Val |
| | | | 35 | | | | | 40 | | | | | 45 | | |
| Ser | Ala | Ile | Ser | Ser | Ser | Gly | Thr | Asn | Thr | Tyr | Tyr | Ala | Asp | Ser | Val |
| | | | 50 | | | | | 55 | | | | | 60 | | |
| Lys | Gly | Gly | Phe | Thr | Ile | Ser | Arg | Asp | Asn | Ser | Lys | Asn | Thr | Leu | Phe |
| 65 | | | | | 70 | | | | | 75 | | | | | 80 |
| Leu | Gln | Met | Ser | Ser | Leu | Arg | Val | Glu | Asp | Thr | Ala | Val | Tyr | Tyr | Cys |
| | | | | 85 | | | | | 90 | | | | | 95 | |
| Val | Lys | Gly | Ser | Gly | Val | Gly | Tyr | Gln | Tyr | Tyr | Tyr | Gly | Met | Asp | Val |
| | | | 100 | | | | | 105 | | | | | 110 | | |
| Trp | Gly | Pro | Arg | Asp | His | Gly | His | Arg | Phe | Leu | Arg | Leu | His | Gln | Gly |
| | | | 115 | | | | | 120 | | | | | 125 | | |
| Pro | Lys | | | | | | | | | | | | | | |
| | 130 | | | | | | | | | | | | | | |

```
<210> SEQ ID NO 22
<211> LENGTH: 123
<212> TYPE: PRT
<213> ORGANISM: Artificial Sequence
<220> FEATURE:
<223> OTHER INFORMATION: Toso-binding variable light chain

<400> SEQUENCE: 22
```

| | | | | | | | | | | | | | | | |
|---|---|---|---|---|---|---|---|---|---|---|---|---|---|---|---|
| Val | Asp | Ile | Leu | Met | Thr | Gln | Ser | Pro | Asp | Ser | Leu | Ala | Val | Ser | Leu |

```
                 1               5                  10                  15
            Gly Glu Arg Ala Thr Ile Asn Cys Lys Ser Ser Gln Asn Val Leu Tyr
                            20                  25                  30

Asn Ser Asn Lys Lys Asn Tyr Leu Ala Trp Tyr Gln Gln Lys Pro Gly
                            35                  40                  45

Gln Pro Pro Lys Leu Leu Thr Tyr Trp Ala Ser Thr Arg Glu Ser Gly
                    50                  55                  60

Val Pro Asp Arg Phe Thr Gly Ser Gly Ser Arg Thr Asp Phe Thr Leu
             65                  70                  75                  80

Thr Ile Ser Ser Leu Gln Ala Glu Asp Val Ala Val Tyr Tyr Cys Gln
                            85                  90                  95

Gln Tyr Tyr Gly Thr Pro Leu Thr Phe Gly Gly Gly Thr Lys Val Glu
                            100                 105                 110

Ile Lys Arg Arg Leu Trp Leu His His Leu Ser
                            115                 120

<210> SEQ ID NO 23
<211> LENGTH: 131
<212> TYPE: PRT
<213> ORGANISM: Artificial Sequence
<220> FEATURE:
<223> OTHER INFORMATION: Toso-binding variable heavy chain

<400> SEQUENCE: 23

Ala Gly Gln Leu Val Gln Ser Gly Ala Glu Ala Arg Pro Gly Ala
 1               5                  10                  15

Ser Val Lys Val Ser Cys Lys Ala Ser Gly Tyr Ser Leu Ser Asp Tyr
                20                  25                  30

Ser Val His Trp Val Arg Gln Thr Arg Asp Gln Gly Leu Glu Trp Met
                35                  40                  45

Gly Trp Ile Asn Pro Lys Thr Gly Gly Thr Thr Tyr Ala Gln Asn Phe
        50                  55                  60

Gln Ala Arg Val Thr Met Thr Arg Asp Thr Ser Ile Asn Thr Ala Tyr
 65                  70                  75                  80

Met Glu Leu Arg Arg Leu Arg Tyr Asp Asp Thr Gly Val Tyr Phe Cys
                85                  90                  95

Ala Arg Pro Gly Phe Cys Thr Ile Asp Asn Cys His Asp Phe Phe Asp
                100                 105                 110

Ser Trp Gly His Gly Ser Leu Ile Thr Val Ser Ser Ala Ser Thr Lys
                115                 120                 125

Gly Pro Lys
        130

<210> SEQ ID NO 24
<211> LENGTH: 123
<212> TYPE: PRT
<213> ORGANISM: Artificial Sequence
<220> FEATURE:
<223> OTHER INFORMATION: Toso-binding variable light chain

<400> SEQUENCE: 24

Val Asp Ile Val Met Thr Gln Thr Pro Leu Ser Leu Pro Val Thr Leu
 1               5                  10                  15

Gly Gln Pro Ala Ser Ile Ser Cys Arg Ser Ser Gln Arg Leu Val Tyr
                20                  25                  30

Ser Asp Gly Asn Thr Tyr Leu Asn Trp Phe Gln Gln Arg Pro Gly Gln
                35                  40                  45
```

```
Ser Pro Arg Arg Leu Ile Tyr Lys Val Ser Asn Arg Asp Ser Gly Val
    50                  55                  60

Pro Asp Arg Phe Ser Gly Ser Gly Ser Gly Thr Ala Phe Thr Leu Lys
65                  70                  75                  80

Ile Ser Arg Val Glu Ala Glu Asp Val Gly Ile Tyr Tyr Cys Met Gln
                85                  90                  95

Ser Ser Thr Asp Trp Pro Trp Thr Phe Gly Gln Gly Thr Arg Val Glu
                100                 105                 110

Ile Lys Arg Thr Val Ala Ala Pro Ser Val Phe
            115                 120

<210> SEQ ID NO 25
<211> LENGTH: 129
<212> TYPE: PRT
<213> ORGANISM: Artificial Sequence
<220> FEATURE:
<223> OTHER INFORMATION: Toso-binding variable heavy chain

<400> SEQUENCE: 25

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Tyr Met Tyr Trp Val Arg Gln Ala Pro Gly Gln Arg Leu Glu Trp Met
            35                  40                  45

Gly Arg Ile Asn Pro Lys Thr Gly Gly Thr Asn Tyr Ala Gln His Phe
    50                  55                  60

Gln Gly Arg Val Thr Met Thr Arg Asp Thr Ser Ile Ser Thr Ala Tyr
65                  70                  75                  80

Met Glu Phe Ser Arg Leu Thr Ser Asp Asp Thr Ala Val Tyr Tyr Cys
                85                  90                  95

Ala Arg Arg Ser Leu Asn Leu Tyr Tyr Asp Tyr Gly Met Asp Val Trp
                100                 105                 110

Gly Gln Gly Thr Thr Val Ile Val Ser Ser Ala Ser Thr Lys Gly Pro
            115                 120                 125

Lys

<210> SEQ ID NO 26
<211> LENGTH: 124
<212> TYPE: PRT
<213> ORGANISM: Artificial Sequence
<220> FEATURE:
<223> OTHER INFORMATION: Toso-binding variable light chain

<400> SEQUENCE: 26

Val Asp Ile Val Met Thr Gln Ala Pro Leu Ser Leu Ala Val Ser Leu
1               5                   10                  15

Gly Glu Arg Ala Thr Ile Asn Cys Lys Ser Ser Arg Ser Val Leu Tyr
                20                  25                  30

Thr Ser Thr Asn Arg Tyr Leu Leu Ala Trp Tyr Gln Gln Lys Pro Gly
            35                  40                  45

Gln Pro Pro Lys Leu Leu Ile Tyr Trp Ala Ser Thr Arg Glu Ser Gly
    50                  55                  60

Val Pro Asp Arg Phe Ser Gly Ser Gly Ser Gly Thr Asp Phe Thr Leu
65                  70                  75                  80

Thr Ile Ser Ser Val Gln Ala Glu Asp Val Ala Val Tyr Tyr Cys Gln
                85                  90                  95
```

Gln Tyr Tyr Asn Pro Pro Val Tyr Thr Phe Gly Gln Gly Thr Arg Leu
                100                 105                 110

Glu Ile Lys Lys Thr Val Ala Ala Pro Ser Val Phe
            115                 120

<210> SEQ ID NO 27
<211> LENGTH: 132
<212> TYPE: PRT
<213> ORGANISM: Artificial Sequence
<220> FEATURE:
<223> OTHER INFORMATION: Toso-binding variable heavy chain

<400> SEQUENCE: 27

Gln Val Gln Leu Gln Gln Ser Gly Pro Gly Leu Val Arg Pro Ser Glu
1               5                   10                  15

Thr Leu Ser Leu Ala Cys Ser Val Ser Gly Ala Leu Val Thr Asn Thr
            20                  25                  30

Ala Tyr Tyr Trp Gly Trp Phe Arg Gln Ser Pro Gly Gln Gly Leu Glu
        35                  40                  45

Trp Ile Gly Cys Ile Tyr Ala Asn Gly Arg Thr Tyr Thr Asn Pro Ser
    50                  55                  60

Leu Lys Ser Arg Val Ser Leu Ser Ile Asp Gln Ser Arg Gln Arg Phe
65                  70                  75                  80

Ser Leu Asn Leu Thr Ser Ala Thr Ala Thr Asp Thr Ala Val Tyr Tyr
                85                  90                  95

Cys Val Arg Leu Val Pro Lys Arg Thr Ala Thr Leu His Tyr Tyr Ile
            100                 105                 110

Asp Val Trp Gly Lys Gly Thr Thr Val Thr Val Ser Ser Gly Ser Ala
        115                 120                 125

Ser Ala Pro Lys
    130

<210> SEQ ID NO 28
<211> LENGTH: 129
<212> TYPE: PRT
<213> ORGANISM: Artificial Sequence
<220> FEATURE:
<223> OTHER INFORMATION: Toso-binding variable light chain

<400> SEQUENCE: 28

Val Gln Ser Ala Leu Thr Gln Pro Ala Ser Ala Ser Leu Gly
1               5                   10                  15

Ala Ser Val Lys Leu Thr Cys Thr Leu Ser Ser Gly His Ser Ser Tyr
            20                  25                  30

Ala Ile Ala Trp His Gln Gln Pro Glu Lys Gly Pro Arg Tyr Leu
        35                  40                  45

Met Lys Leu Asn Ser Asp Gly Ser His Ser Lys Gly Asn Gly Ile Pro
    50                  55                  60

Asp Arg Phe Ser Gly Ser Ser Ser Gly Ala Glu Arg Tyr Leu Thr Ile
65                  70                  75                  80

Ser Ser Leu Gln Ser Glu Asp Glu Ala Asp Tyr Tyr Cys Gln Thr Trp
                85                  90                  95

Gly Thr Gly Ile His Trp Val Phe Gly Gly Thr Lys Leu Thr Val
            100                 105                 110

Leu Gly Gln Pro Lys Ala Pro Pro Ser Val Thr Leu Phe Pro Pro Ser
        115                 120                 125

Ser

```
<210> SEQ ID NO 29
<211> LENGTH: 131
<212> TYPE: PRT
<213> ORGANISM: Artificial Sequence
<220> FEATURE:
<223> OTHER INFORMATION: Toso-binding variable heavy chain

<400> SEQUENCE: 29

Gln Val Gln Leu Gln Gln Ser Gly Ala Glu Val Arg Lys Pro Gly Ser
1               5                   10                  15

Ser Val Asn Val Ser Cys Lys Ala Ser Gly Asp Thr Ser Ser Ile Tyr
            20                  25                  30

Ala Ile Ser Trp Val Arg Gln Ala Pro Gly Gln Gly Leu Glu Trp Met
        35                  40                  45

Gly Arg Ile Asn Pro Ile Pro Arg Ile Thr Thr Tyr Ala Gln Lys Phe
    50                  55                  60

Gln Asp Arg Ala Thr Ile Thr Ala Asp Ile Ser Thr Ser Thr Val Tyr
65                  70                  75                  80

Met Asp Leu Ser Ser Leu Thr Ser Glu Asp Thr Ala Val Tyr Tyr Cys
                85                  90                  95

Ala Arg Asp Cys Ser Gly Gly Ser Cys Phe Arg Gln Asp Ala Phe Asp
            100                 105                 110

Ile Trp Gly Gln Gly Ile Met Val Thr Val Ser Ser Ala Ser Thr Lys
        115                 120                 125

Gly Pro Lys
    130

<210> SEQ ID NO 30
<211> LENGTH: 114
<212> TYPE: PRT
<213> ORGANISM: Artificial Sequence
<220> FEATURE:
<223> OTHER INFORMATION: Toso-binding variable light chain
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (107)..(108)
<223> OTHER INFORMATION: Xaa can be any naturally occurring amino acid

<400> SEQUENCE: 30

Ile Leu Ser Gln Ala Pro Leu Ser Leu Ser Ala Ser Ile Gly Asp Ser
1               5                   10                  15

Val Thr Ile Thr Cys Arg Ala Ser Gln Ser Val Ser Asp Tyr Leu Asn
            20                  25                  30

Trp Tyr Gln Gln Lys Pro Gly Lys Ala Pro Lys Leu Leu Ile Tyr Ala
        35                  40                  45

Ala Ser Ser Leu Gln Ser Gly Val Pro Ser Arg Phe Ile Gly Ser Gly
    50                  55                  60

Ser Gly Thr Asp Phe Thr Leu Thr Ile Ser Ser Leu Gln Pro Glu Xaa
65                  70                  75                  80

Phe Ala Thr Tyr Tyr Cys Xaa Gln Ser Tyr Thr Thr Ala Tyr Thr Phe
                85                  90                  95

Gly Gln Gly Thr Lys Leu Glu Ile Gln Arg Xaa Xaa Ala Ala Pro Ser
            100                 105                 110
```

Val Phe

```
<210> SEQ ID NO 31
<211> LENGTH: 131
<212> TYPE: PRT
<213> ORGANISM: Artificial Sequence
<220> FEATURE:
<223> OTHER INFORMATION: Toso-binding variable heavy chain
```

<400> SEQUENCE: 31

Gln Val Gln Leu Gln Gln Ser Gly Ala Glu Val Arg Lys Pro Gly Ser
1               5                   10                  15

Ser Val Asn Val Ser Cys Lys Ala Ser Gly Asp Thr Ser Ser Ile Tyr
            20                  25                  30

Ala Ile Ser Trp Val Arg Gln Ala Pro Gly Gln Gly Leu Glu Trp Met
        35                  40                  45

Gly Arg Ile Asn Pro Ile Pro Arg Ile Thr Thr Tyr Ala Gln Lys Phe
50                  55                  60

Gln Asp Arg Ala Thr Ile Thr Ala Asp Ile Ser Thr Ser Thr Val Tyr
65                  70                  75                  80

Met Asp Leu Ser Ser Leu Thr Ser Glu Asp Thr Ala Val Tyr Tyr Cys
                85                  90                  95

Ala Arg Asp Cys Ser Gly Gly Ser Cys Phe Arg Gln Asp Ala Phe Asp
            100                 105                 110

Ile Trp Gly Gln Gly Ile Met Val Thr Val Ser Ser Ala Ser Thr Lys
        115                 120                 125

Gly Pro Lys
    130

```
<210> SEQ ID NO 32
<211> LENGTH: 114
<212> TYPE: PRT
<213> ORGANISM: Artificial Sequence
<220> FEATURE:
<223> OTHER INFORMATION: Toso-binding variable light chain
```

<400> SEQUENCE: 32

Ile Leu Ser Gln Ala Pro Leu Ser Leu Ser Ala Ser Ile Gly Asp Ser
1               5                   10                  15

Val Thr Ile Thr Cys Arg Ala Ser Gln Ser Val Ser Asp Tyr Leu Asn
            20                  25                  30

Trp Tyr Gln Gln Lys Pro Gly Lys Ala Pro Lys Leu Leu Ile Tyr Ala
        35                  40                  45

Ala Ser Ser Leu Gln Ser Gly Val Pro Ser Arg Phe Ile Gly Ser Gly
50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Thr Thr Ala Tyr Thr Phe
                85                  90                  95

Gly Gln Gly Thr Lys Leu Glu Ile Gln Arg Thr Val Ala Ala Pro Ser
            100                 105                 110

Val Phe

```
<210> SEQ ID NO 33
<211> LENGTH: 129
<212> TYPE: PRT
<213> ORGANISM: Artificial Sequence
<220> FEATURE:
```

<223> OTHER INFORMATION: Toso-binding variable heavy chain

<400> SEQUENCE: 33

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Leu Thr Ser Tyr
            20                  25                  30
Asp Val Asn Trp Val Arg Gln Ala Thr Gly Gln Gly Leu Glu Trp Met
        35                  40                  45
Gly Trp Met Asn Pro Asn Ser Gly Asn Thr Gly Tyr Ala Gln Lys Phe
    50                  55                  60
Gln Gly Arg Val Thr Met Thr Arg Asn Thr Ser Ile Gly Thr Ala Tyr
65                  70                  75                  80
Met Glu Leu Asn Ser Leu Thr Ser Asp Asp Thr Ala Val Tyr Tyr Cys
                85                  90                  95
Ala Arg Gly Arg Ser Ile Ile Asn His Tyr Tyr Gly Leu Asp Val Trp
            100                 105                 110
Gly His Gly Thr Thr Val Thr Val Ser Ser Ala Ser Thr Lys Gly Pro
        115                 120                 125
Lys

<210> SEQ ID NO 34
<211> LENGTH: 117
<212> TYPE: PRT
<213> ORGANISM: Artificial Sequence
<220> FEATURE:
<223> OTHER INFORMATION: Toso-binding variable light chain

<400> SEQUENCE: 34

Val Glu Ile Val Leu Thr Gln Ser Pro Ala Thr Leu Ser Leu Ser Pro
1               5                   10                  15
Gly Glu Arg Ala Thr Leu Ser Cys Arg Ala Ser Gln Ser Val Ser Ser
            20                  25                  30
Tyr Leu Ala Trp Tyr Gln Gln Lys Pro Gly Gln Ala Pro Arg Leu Leu
        35                  40                  45
Ile Tyr Asp Ala Ser Asn Arg Ala Thr Gly Ile Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Arg Ser Asn Trp Pro
                85                  90                  95
Trp Thr Phe Gly Gln Gly Thr Lys Val Glu Ile Lys Arg Thr Val Ala
            100                 105                 110
Ala Pro Ser Val Phe
        115

<210> SEQ ID NO 35
<211> LENGTH: 136
<212> TYPE: PRT
<213> ORGANISM: Artificial Sequence
<220> FEATURE:
<223> OTHER INFORMATION: Toso-binding variable heavy chain

<400> SEQUENCE: 35

Met Ala Glu Val Gln Leu Val Gln Ser Gly Gly Gly Leu Val Gln Pro
1               5                   10                  15
Gly Gly Ser Leu Arg Leu Ser Cys Val Ala Ser Asp Phe Ile Phe Asn
            20                  25                  30

```
Asn Tyr Asn Met Asn Trp Val Arg Gln Ala Pro Gly Lys Gly Leu Glu
            35                  40                  45

Trp Leu Ser Phe Ile Asp Thr Ser Thr Tyr Thr Tyr Tyr Ala Asp
 50                  55                  60

Ser Val Arg Gly Arg Phe Thr Ile Ser Arg Asp Asn Ser Lys Lys Ser
 65                  70                  75                  80

Leu Phe Leu Gln Met Asn Thr Leu Thr Asp Asp Thr Ala Val Tyr
                85                  90                  95

Phe Cys Ala Arg Asp Arg Tyr Gly Ser Ser Tyr Trp Gly Gly His Tyr
                100                 105                 110

Phe His Ala Met Asp Val Trp Gly Gln Gly Thr Pro Val Thr Val Ser
            115                 120                 125

Ser Ala Ser Thr Lys Gly Pro Lys
            130                 135
```

<210> SEQ ID NO 36
<211> LENGTH: 119
<212> TYPE: PRT
<213> ORGANISM: Artificial Sequence
<220> FEATURE:
<223> OTHER INFORMATION: Toso-binding variable light chain
<220> FEATURE:
<221> NAME/KEY: misc_feature
<222> LOCATION: (83)..(83)
<223> OTHER INFORMATION: Xaa can be any naturally occurring amino acid

<400> SEQUENCE: 36

```
Val Glu Ile Val Leu Thr Gln Ser Pro Ala Thr Leu Ser Ser Ser Pro
 1               5                  10                  15

Gly Glu Arg Ala Thr Leu Ser Cys Arg Ala Ser Gln Ser Val Gly Thr
            20                  25                  30

Ser Leu Ala Trp Tyr Gln Gln Ile Pro Gly Gln Ala Pro Ser Leu Leu
            35                  40                  45

Ile His Asp Ala Ser Asn Arg Ala Ser Gly Ile Pro Ala Arg Phe Ser
 50                  55                  60

Gly Ser Gly Ser Gly Thr Asp Phe Thr Leu Thr Ile Asn Ser Leu Glu
 65                  70                  75                  80

Pro Glu Xaa Phe Ala Val Tyr Tyr Cys Gln Gln Arg Ser Asn Gly Pro
                85                  90                  95

Pro Ser Trp Thr Phe Gly Gln Gly Thr Lys Val Glu Ile Lys Arg Thr
            100                 105                 110

Val Ala Ala Pro Ser Val Phe
            115
```

<210> SEQ ID NO 37
<211> LENGTH: 134
<212> TYPE: PRT
<213> ORGANISM: Artificial Sequence
<220> FEATURE:
<223> OTHER INFORMATION: Toso-binding variable heavy chain

<400> SEQUENCE: 37

```
Ala Gly Ala Ala Gly Ala Val Trp Gly Arg Pro Gly Gln Ala Gly Gly
 1               5                  10                  15

Ser Leu Arg Leu Ser Cys Ala Ala Ala Gly Phe Ser Phe Ser Ser Tyr
            20                  25                  30

Asn Leu Asn Trp Val Arg Gln Ala Pro Gly Lys Gly Leu Glu Trp Leu
            35                  40                  45
```

```
Ser Ser Ile Ser Ser Gly Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Thr Arg Asp Arg Tyr Tyr His Asp Ser Asp Glu Tyr Tyr Asp Ala Asp
                100                 105                 110

Gly Phe Asp Val Trp Gly Gln Gly Thr Leu Val Thr Val Ser Ser Ala
                115                 120                 125

Ser Thr Lys Gly Pro Lys
            130

<210> SEQ ID NO 38
<211> LENGTH: 115
<212> TYPE: PRT
<213> ORGANISM: Artificial Sequence
<220> FEATURE:
<223> OTHER INFORMATION: Toso-binding variable light chain

<400> SEQUENCE: 38

Val Asp Ile Leu Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser Ser
                20                  25                  30

Tyr Leu Asn Trp Tyr Gln Gln Lys Pro Gly Lys Ala Pro Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Leu Ser
                    85                  90                  95

Leu Ser Ala Glu Gly Pro Arg Trp Arg Ser Asn Glu Leu Trp Leu His
                100                 105                 110

His Leu Ser
        115

<210> SEQ ID NO 39
<211> LENGTH: 127
<212> TYPE: PRT
<213> ORGANISM: Artificial Sequence
<220> FEATURE:
<223> OTHER INFORMATION: Toso-binding variable heavy chain

<400> SEQUENCE: 39

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Ser Trp Val Arg Gln Val Pro Gly Lys Gly Leu Glu Trp Val
            35                  40                  45

Ser Ser Ile Ser Ala Asn Gly Thr Thr Tyr Tyr Gly Asp Ser Val
        50                  55                  60

Arg Gly Arg Phe Thr Ile Ser Arg Asp Asn Ala Lys Asn Thr Leu Tyr
 65                  70                  75                  80

Leu Gln Met Asn Ser Leu Thr Ala Glu Asp Thr Ala Lys Tyr Tyr Cys
                    85                  90                  95
```

```
Ala Arg Asp His Leu Trp Phe Gly Glu Tyr Ile Phe Asp Cys Trp Gly
                100                 105                 110

Gln Gly Thr Leu Val Ser Val Ser Ser Leu His Gln Gly Pro Lys
            115                 120                 125

<210> SEQ ID NO 40
<211> LENGTH: 122
<212> TYPE: PRT
<213> ORGANISM: Artificial Sequence
<220> FEATURE:
<223> OTHER INFORMATION: Toso-binding variable light chain

<400> SEQUENCE: 40

Val Asp Ile Glu Met Thr Gln Ser Pro Asp Ser Leu Ala Val Ser Leu
1               5                   10                  15

Gly Glu Arg Ala Thr Ile Asn Cys Lys Ser Ser Gln Ser Val Phe Ser
                20                  25                  30

Ser Ser Tyr Ser Glu Asp Tyr Leu Ala Trp Tyr Gln Gln Lys Pro Gly
            35                  40                  45

Gln Ala Pro Lys Leu Leu Ile Tyr Trp Ala Ser Thr Arg Glu Ser Gly
        50                  55                  60

Val Pro Asp Arg Phe Thr Gly Ser Gly Ser Gly Thr Asp Phe Thr Leu
65                  70                  75                  80

Thr Ile Ser Ser Leu Gln Val Glu Asp Val Ala Val Tyr Tyr Cys Gln
                85                  90                  95

Gln Tyr Tyr Ile Thr Pro Ile Thr Phe Gly Gln Gly Thr Arg Leu Glu
                100                 105                 110

Ile Thr Asn Cys Gly Cys Thr Ile Cys Leu
            115                 120

<210> SEQ ID NO 41
<211> LENGTH: 126
<212> TYPE: PRT
<213> ORGANISM: Artificial Sequence
<220> FEATURE:
<223> OTHER INFORMATION: Toso-binding variable heavy chain

<400> SEQUENCE: 41

Gly Gly Ala Val Val Gln Ser Gly Gly Gly Met Val Lys Pro Gly Gly
1               5                   10                  15

Ser Leu Arg Leu Ser Cys Ala Ala Ser Gly Phe Thr Phe Thr Asp Ala
                20                  25                  30

Trp Met Ile Trp Val Arg Gln Ala Pro Gly Lys Gly Leu Glu Trp Val
            35                  40                  45

Gly Arg Ile Lys Ser Arg Thr Gly Gly Thr Thr Asp Tyr Ala Ala
        50                  55                  60

Pro Val Gln Gly Arg Phe Thr Ile Ser Arg Asp Asp Ser Lys Ala Thr
65                  70                  75                  80

Val Tyr Leu Gln Met Asn Ser Leu Asn Thr Glu Asp Thr Ala Val Tyr
                85                  90                  95

Phe Cys Val Trp Ser Gly Arg Asn Trp Phe Gly His Trp Gly Gln Gly
                100                 105                 110

Thr Leu Val Thr Val Ser Ser Ala Ser Thr Lys Gly Pro Lys
            115                 120                 125

<210> SEQ ID NO 42
<211> LENGTH: 121
<212> TYPE: PRT
```

<213> ORGANISM: Artificial Sequence
<220> FEATURE:
<223> OTHER INFORMATION: Toso-binding variable light chain
<220> FEATURE:
<221> NAME/KEY: misc_feature
<222> LOCATION: (107)..(107)
<223> OTHER INFORMATION: Xaa can be any naturally occurring amino acid

<400> SEQUENCE: 42

Val Asp Ile Val Met Thr Gln Ala Pro Leu Ser Ser Pro Val Thr Leu
1               5                   10                  15

Gly Gln Pro Ala Ser Ile Ser Cys Arg Ser Ser Gln Ser Leu Val His
                20                  25                  30

Ser Asp Gly Asn Thr Tyr Leu Ser Trp Leu Gln Gln Arg Pro Gly Gln
            35                  40                  45

Pro Pro Arg Leu Leu Ile Tyr Lys Ile Ser Asn Arg Phe Ser Gly Ser
        50                  55                  60

Gln Thr Asp Ser Val Ala Val Gly Gln Gly Ile Ser His Lys Ser
65                  70                  75                  80

Ala Gly Trp Lys Leu Arg Met Ser Gly Phe Ile Thr Ala Cys Lys Leu
                85                  90                  95

His Asn Phe Leu Thr Leu Leu Ala Arg Gly Xaa Ser Trp Arg Ser Lys
            100                 105                 110

Lys Thr Val Ala Ala Pro Ser Val Phe
        115                 120

<210> SEQ ID NO 43
<211> LENGTH: 128
<212> TYPE: PRT
<213> ORGANISM: Artificial Sequence
<220> FEATURE:
<223> OTHER INFORMATION: Toso-binding variable heavy chain

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Asp Val Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Gly Thr Ala Tyr
65                  70                  75                  80

Met Glu Leu Asn Ser Leu Thr Ser Asp Asp Thr Ala Val Tyr Tyr Cys
                85                  90                  95

Ala Arg Gly Arg Ser Ile Ile Asn His Tyr Tyr Gly Leu Asp Val Trp
            100                 105                 110

Ala Thr Gly Pro Arg Ser Pro Ser Pro Gln Pro Pro Arg Ala Gln
        115                 120                 125

<210> SEQ ID NO 44
<211> LENGTH: 117
<212> TYPE: PRT
<213> ORGANISM: Artificial Sequence
<220> FEATURE:
<223> OTHER INFORMATION: Toso-binding variable light chain

<400> SEQUENCE: 44

Val Asp Ile Val Met Thr Gln Thr Pro Leu Ser Leu Ser Ala Ser Val

```
                1               5                  10                   15
            Gly Asp Arg Val Thr Ile Thr Cys Arg Ala Asn Gln Ser Ile Ser Asn
                            20                  25                  30

Tyr Leu Asn Trp Tyr Gln Gln Lys Pro Arg Lys Ala Pro Asn Leu Leu
                        35                  40                  45

Ile Tyr Ala Ala Ser Ser Leu Gln Ser Gly Val Pro Ser Arg Phe Ser
                    50                  55                  60

Gly Ser Gly Ser Gly Thr Asp Phe Thr Leu Thr Ile Ser Ser Leu Gln
            65                  70                  75                  80

Pro Glu Asp Phe Ala Thr Tyr Tyr Cys Gln Gln Ser Tyr Ser Thr Pro
                            85                  90                  95

Glu Thr Phe Gly Gln Gly Thr Lys Val Glu Ile Lys Arg Thr Val Ala
                        100                 105                 110

Ala Pro Ser Val Phe
                    115

<210> SEQ ID NO 45
<211> LENGTH: 125
<212> TYPE: PRT
<213> ORGANISM: Artificial Sequence
<220> FEATURE:
<223> OTHER INFORMATION: Toso-binding variable heavy chain

<400> SEQUENCE: 45

Gly Gly Leu Val Gln Pro Gly Gly Ser Leu Arg Leu Ser Cys Val Ala
            1               5                  10                   15

Ser Asp Phe Ile Phe Asn Asn Tyr Asn Met Asn Trp Val Arg Gln Ala
                            20                  25                  30

Pro Gly Lys Gly Leu Glu Trp Leu Ser Phe Ile Asp Thr Ser Thr Tyr
                        35                  40                  45

Thr Thr Tyr Tyr Ala Asp Ser Val Arg Gly Arg Phe Thr Ile Ser Arg
                    50                  55                  60

Asp Asn Ser Lys Lys Ser Leu Phe Leu Gln Met Asn Thr Leu Thr Asp
            65                  70                  75                  80

Asp Asp Thr Ala Val Tyr Phe Cys Ala Arg Asp Arg Tyr Gly Ser Ser
                            85                  90                  95

Tyr Trp Gly Ala Thr Ile Ser Thr Leu Trp Thr Ser Gly Gly Lys Gly
                        100                 105                 110

Pro Arg Ser Pro Ser Pro Gln Pro Pro Arg Ala Gln
                    115                 120                 125

<210> SEQ ID NO 46
<211> LENGTH: 117
<212> TYPE: PRT
<213> ORGANISM: Artificial Sequence
<220> FEATURE:
<223> OTHER INFORMATION: Toso-binding variable light chain

<400> SEQUENCE: 46

Arg Arg Tyr Cys Asp Asp Ser Gly Ser Thr Leu Thr Val Cys Ile Cys
            1               5                  10                   15

Arg Arg Gln Ser His Ile Thr Cys Arg Ala Ser Gln Ser Ile Ser Ser
                            20                  25                  30

Tyr Leu Asn Trp Tyr Gln Gln Lys Pro Gly Lys Ala Pro Lys Leu Leu
                        35                  40                  45

Ile Tyr Ala Ala Ser Ser Leu Gln Ser Gly Val Pro Ser Arg Phe Ser
                    50                  55                  60
```

```
Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Cys Thr Phe Gly Gln Gly Thr Lys Leu Glu Ile Lys Arg Thr Val Ala
            100                 105                 110

Ala Pro Ser Val Phe
            115
```

<210> SEQ ID NO 47
<211> LENGTH: 133
<212> TYPE: PRT
<213> ORGANISM: Artificial Sequence
<220> FEATURE:
<223> OTHER INFORMATION: Toso-binding variable heavy chain

<400> SEQUENCE: 47

```
Ala Gly Glu Leu Val Gln Ser Gly Ala Glu Val Arg Lys Pro Gly Glu
1               5                   10                  15

Ser Leu Gln Ile Ser Cys Thr Ala Ser Gly Tyr Ile Phe Thr Asp Tyr
                20                  25                  30

Trp Ile Gly Trp Val Arg Gln Met Pro Gly Lys Gly Leu Glu Ser Met
            35                  40                  45

Gly Ile Ile Tyr Pro Gly Asp Ser Glu Thr Ser Ser Pro Ser Phe Gln
50                  55                  60

Gly Gln Val Ile Met Ser Val Asp Lys Tyr Arg Asn Ile Ala Tyr Leu
65                  70                  75                  80

Gln Trp Asn Ser Leu Lys Ala Ser Asp Thr Ala Thr Tyr Phe Cys Ala
                85                  90                  95

Arg His Gly Arg Gly Tyr Cys Gly Gly Gly Ser Cys Gln Gly Thr Leu
            100                 105                 110

Ile Asp Asn Trp Gly Gln Gly Thr Leu Leu Thr Val Ser Ala Ala Ser
        115                 120                 125

Thr Lys Gly Pro Lys
        130
```

<210> SEQ ID NO 48
<211> LENGTH: 123
<212> TYPE: PRT
<213> ORGANISM: Artificial Sequence
<220> FEATURE:
<223> OTHER INFORMATION: Toso-binding variable light chain

<400> SEQUENCE: 48

```
Val Asp Ile Glu Met Thr Gln Ser Pro Asp Ser Leu Ala Val Ser Leu
1               5                   10                  15

Gly Glu Arg Ala Thr Ile Asn Cys Lys Ser Ser Gln Ser Val Phe Ser
                20                  25                  30

Ser Ser Tyr Ser Glu Asp Tyr Leu Ala Trp Tyr Gln Gln Lys Pro Gly
            35                  40                  45

Gln Ala Pro Lys Leu Leu Ile Tyr Trp Ala Ser Thr Arg Glu Ser Gly
50                  55                  60

Val Pro Asp Arg Phe Thr Gly Ser Gly Ser Gly Thr Asp Phe Thr Leu
65                  70                  75                  80

Thr Ile Ser Ser Leu Gln Val Glu Asp Val Ala Val Tyr Tyr Cys Gln
                85                  90                  95

Gln Tyr Tyr Ile Thr Pro Ile Thr Phe Gly Gln Gly Thr Arg Leu Glu
            100                 105                 110
```

-continued

Ile Lys Arg Thr Val Ala Ala His Met Ser Ser
            115                 120

<210> SEQ ID NO 49
<211> LENGTH: 133
<212> TYPE: PRT
<213> ORGANISM: Artificial Sequence
<220> FEATURE:
<223> OTHER INFORMATION: Toso-binding variable heavy chain

<400> SEQUENCE: 49

Ala Gly Glu Leu Val Gln Ser Gly Ala Glu Val Arg Lys Pro Gly Glu
1               5                   10                  15

Ser Leu Gln Ile Ser Cys Thr Ala Ser Gly Tyr Ile Phe Thr Asp Tyr
            20                  25                  30

Trp Ile Gly Trp Val Arg Gln Met Pro Gly Lys Gly Leu Glu Ser Met
        35                  40                  45

Gly Ile Ile Tyr Pro Gly Asp Ser Glu Thr Ser Ser Pro Ser Phe Gln
    50                  55                  60

Gly Gln Val Ile Met Ser Val Asp Lys Tyr Arg Asn Ile Ala Tyr Leu
65                  70                  75                  80

Gln Trp Asn Ser Leu Lys Ala Ser Asp Thr Ala Thr Tyr Phe Cys Ala
                85                  90                  95

Arg His Gly Arg Gly Tyr Cys Gly Gly Gly Ser Cys Gln Gly Thr Leu
            100                 105                 110

Ile Asp Asn Trp Gly Gln Gly Thr Leu Leu Thr Val Ser Ala Ala Ser
        115                 120                 125

Thr Lys Gly Pro Lys
    130

<210> SEQ ID NO 50
<211> LENGTH: 122
<212> TYPE: PRT
<213> ORGANISM: Artificial Sequence
<220> FEATURE:
<223> OTHER INFORMATION: Toso-binding variable light chain

<400> SEQUENCE: 50

Val Ser Glu Leu Thr Gln Asp Pro Ala Val Ser Val Ala Leu Gly Gln
1               5                   10                  15

Thr Gly Arg Ile Thr Cys Gln Gly Asp Ser Leu Arg Thr Tyr Tyr Ala
            20                  25                  30

Asn Trp Tyr Gln Gln Lys Pro Gly Gln Ala Pro Val Leu Val Ile Tyr
        35                  40                  45

Ala Lys Thr Ser Gly Pro Gln Gly Ser Gln Thr Asp Ser Leu Ala Pro
    50                  55                  60

Ala Gln Glu Thr Gln Leu Thr Pro Ser Leu Gly Ala Gln Ala Glu Asp
65                  70                  75                  80

Glu Ser Asp Tyr Tyr Cys Asn Ser Arg Asp Ser Ser Asp Asn Leu Val
                85                  90                  95

Val Phe Gly Gly Gly Thr Lys Leu Thr Val Arg Gly Gln Pro Lys Ala
            100                 105                 110

Ala Pro Arg Ala Leu Cys Ser Thr Pro Leu
        115                 120

<210> SEQ ID NO 51
<211> LENGTH: 128
<212> TYPE: PRT

```
<213> ORGANISM: Artificial Sequence
<220> FEATURE:
<223> OTHER INFORMATION: Toso-binding variable heavy chain

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Asp Val Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
50                  55                  60

Gln Gly Arg Val Thr Met Thr Arg Asn Thr Ser Ile Gly Thr Ala Tyr
65                  70                  75                  80

Met Glu Leu Asn Ser Leu Thr Ser Asp Asp Thr Ala Val Tyr Tyr Cys
                85                  90                  95

Ala Arg Gly Arg Ser Ile Ile Asn His Tyr Tyr Gly Leu Asp Val Trp
            100                 105                 110

Gly His Gly Thr Thr Val Thr Val Ser Ser Ala Ser Pro Arg Ala Gln
        115                 120                 125

<210> SEQ ID NO 52
<211> LENGTH: 118
<212> TYPE: PRT
<213> ORGANISM: Artificial Sequence
<220> FEATURE:
<223> OTHER INFORMATION: Toso-binding variable light chain

<400> SEQUENCE: 52

Arg Arg Tyr Cys Glu Thr Gln Ala Pro Leu Ser Leu Ser Ala Ser Val
1               5                   10                  15

Gly Asp Arg Val Thr Ile Thr Cys Gln Ala Ser Gln Asp Ile Ser Asn
            20                  25                  30

Tyr Leu Asn Trp Tyr Gln Gln Lys Pro Gly Lys Ala Pro Lys Leu Leu
        35                  40                  45

Ile Tyr Asp Ala Ser Asn Leu Glu Thr Gly Gly Pro Ser Arg Phe Ser
50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Tyr Asp Asn Leu Pro
                85                  90                  95

Pro Gly Ser Pro Ser Ala Lys Gly His Asp Arg Arg Leu Asn Glu Leu
            100                 105                 110

Trp Leu His His Leu Ser
        115

<210> SEQ ID NO 53
<211> LENGTH: 133
<212> TYPE: PRT
<213> ORGANISM: Artificial Sequence
<220> FEATURE:
<223> OTHER INFORMATION: Toso-binding variable heavy chain

<400> SEQUENCE: 53

Ala Gly Glu Leu Val Gln Ser Gly Ala Glu Val Arg Lys Pro Gly Glu
1               5                   10                  15

Ser Leu Gln Ile Ser Cys Thr Ala Ser Gly Tyr Ile Phe Thr Asp Tyr
            20                  25                  30
```

```
Trp Ile Gly Trp Val Arg Gln Met Pro Gly Lys Gly Leu Glu Ser Met
            35                  40                  45

Gly Ile Ile Tyr Pro Gly Asp Ser Glu Thr Ser Ser Pro Ser Phe Gln
 50                      55                  60

Gly Gln Val Ile Met Ser Val Asp Lys Tyr Arg Asn Ile Ala Tyr Leu
 65                  70                  75                  80

Gln Trp Asn Ser Leu Lys Ala Ser Asp Thr Ala Thr Tyr Phe Cys Ala
                 85                  90                  95

Arg His Gly Arg Gly Tyr Cys Gly Gly Ser Cys Gln Gly Thr Leu
                100                 105                 110

Ile Asp Asn Trp Gly Gln Gly Thr Leu Leu Thr Val Ser Ala Ala Ser
                115                 120                 125

Thr Lys Gly Pro Lys
        130

<210> SEQ ID NO 54
<211> LENGTH: 123
<212> TYPE: PRT
<213> ORGANISM: Artificial Sequence
<220> FEATURE:
<223> OTHER INFORMATION: Toso-binding variable light chain
<220> FEATURE:
<221> NAME/KEY: misc_feature
<222> LOCATION: (80)..(80)
<223> OTHER INFORMATION: Xaa can be any naturally occurring amino acid

<400> SEQUENCE: 54

Val Ser Glu Leu Thr Gln Asp Pro Ala Val Ser Val Ala Leu Gly Gln
 1               5                  10                  15

Thr Gly Arg Ile Thr Cys Gln Gly Asp Ser Leu Arg Thr Tyr Tyr Ala
                20                  25                  30

Asn Trp Tyr Gln Gln Lys Pro Gly Gln Ala Pro Val Leu Val Ile Tyr
             35                  40                  45

Ala Lys Asn Lys Arg Pro Ser Gly Ile Pro Asp Arg Phe Ser Gly Ser
         50                  55                  60

Ser Ser Gly Asn Thr Ala Tyr Leu Thr Ile Thr Gly Ala Gln Ala Xaa
 65                  70                  75                  80

Asp Glu Ser Asp Tyr Tyr Cys Asn Ser Arg Asp Ser Ser Asp Asn Leu
                 85                  90                  95

Val Val Phe Gly Gly Gly Thr Lys Leu Thr Val Leu Gly Gln Pro Lys
                100                 105                 110

Ala Ala Pro Ser Gly Thr Leu Phe His Pro Pro
            115                 120

<210> SEQ ID NO 55
<211> LENGTH: 133
<212> TYPE: PRT
<213> ORGANISM: Artificial Sequence
<220> FEATURE:
<223> OTHER INFORMATION: Toso-binding variable heavy chain

<400> SEQUENCE: 55

Ala Gly Glu Leu Val Gln Ser Gly Ala Glu Val Arg Lys Pro Gly Glu
 1               5                  10                  15

Ser Leu Gln Ile Ser Cys Thr Ala Ser Gly Tyr Ile Phe Thr Asp Tyr
                20                  25                  30

Trp Ile Gly Trp Val Arg Gln Met Pro Gly Lys Gly Leu Glu Ser Met
            35                  40                  45
```

Gly Ile Ile Tyr Pro Gly Asp Ser Glu Thr Ser Ser Pro Ser Phe Gln
    50                  55                  60

Gly Gln Val Ile Met Ser Val Asp Lys Tyr Arg Asn Ile Ala Tyr Leu
65                  70                  75                  80

Gln Trp Asn Ser Leu Lys Ala Ser Asp Thr Ala Thr Tyr Phe Cys Ala
                85                  90                  95

Arg His Gly Arg Gly Tyr Cys Gly Gly Ser Cys Gln Gly Thr Leu
                100                 105                 110

Ile Asp Asn Trp Gly Gln Gly Thr Leu Leu Thr Val Ser Ala Ala Ser
        115                 120                 125

Thr Lys Gly Pro Lys
    130

<210> SEQ ID NO 56
<211> LENGTH: 122
<212> TYPE: PRT
<213> ORGANISM: Artificial Sequence
<220> FEATURE:
<223> OTHER INFORMATION: Toso-binding variable light chain

<400> SEQUENCE: 56

Val Ser Glu Leu Thr Gln Asp Pro Ala Val Ser Val Ala Leu Gly Gln
1               5                   10                  15

Thr Gly Arg Ile Thr Cys Gln Gly Asp Ser Leu Arg Thr Tyr Tyr Ala
                20                  25                  30

Asn Trp Tyr Gln Gln Lys Pro Gly Gln Ala Pro Val Leu Val Ile Tyr
            35                  40                  45

Ala Lys Thr Ser Gly Pro Gln Gly Ser Gln Thr Asp Ser Leu Ala Pro
    50                  55                  60

Ala Gln Glu Thr Gln Leu Thr Pro Ser Leu Gly Ala Gln Ala Glu Asp
65                  70                  75                  80

Glu Ser Asp Tyr Tyr Cys Asn Ser Arg Asp Ser Ser Asp Asn Leu Val
                85                  90                  95

Val Phe Gly Gly Gly Thr Lys Leu Thr Val Leu Gly His Pro Lys Ala
                100                 105                 110

Ala Pro Ser Gly Thr Leu Phe His Pro Pro
        115                 120

<210> SEQ ID NO 57
<211> LENGTH: 133
<212> TYPE: PRT
<213> ORGANISM: Artificial Sequence
<220> FEATURE:
<223> OTHER INFORMATION: Toso-binding variable heavy chain

<400> SEQUENCE: 57

Ala Gly Glu Leu Val Gln Ser Gly Ala Glu Val Arg Lys Pro Gly Glu
1               5                   10                  15

Ser Leu Gln Ile Ser Cys Thr Ala Ser Gly Tyr Ile Phe Thr Asp Tyr
                20                  25                  30

Trp Ile Gly Trp Val Arg Gln Met Pro Gly Lys Gly Leu Glu Ser Met
            35                  40                  45

Gly Ile Ile Tyr Pro Gly Asp Ser Glu Thr Ser Ser Pro Ser Phe Gln
    50                  55                  60

Gly Gln Val Ile Met Ser Val Asp Lys Tyr Arg Asn Ile Ala Tyr Leu
65                  70                  75                  80

Gln Trp Asn Ser Leu Lys Ala Ser Asp Thr Ala Thr Tyr Phe Cys Ala
                85                  90                  95

Arg His Gly Arg Gly Tyr Cys Gly Gly Ser Cys Gln Gly Thr Leu
            100                 105                 110

Ile Asp Asn Trp Gly Gln Gly Thr Leu Leu Thr Val Ser Ala Ala Ser
        115                 120                 125

Thr Lys Gly Pro Lys
    130

<210> SEQ ID NO 58
<211> LENGTH: 124
<212> TYPE: PRT
<213> ORGANISM: Artificial Sequence
<220> FEATURE:
<223> OTHER INFORMATION: Toso-binding variable light chain

<400> SEQUENCE: 58

Val Ser Glu Leu Thr Gln Asp Pro Ala Val Ser Val Ala Leu Gly Gln
1               5                   10                  15

Thr Gly Arg Ile Thr Cys Gln Gly Asp Ser Leu Arg Thr Tyr Tyr Ala
            20                  25                  30

Asn Trp Tyr Gln Gln Lys Pro Gly Gln Ala Pro Val Leu Val Ile Tyr
        35                  40                  45

Ala Lys Asn Lys Arg Pro Ser Gly Ile Pro Asp Arg Phe Ser Gly Ser
    50                  55                  60

Ser Ser Gly Asn Thr Ala Tyr Leu Thr Ile Thr Gly Ala Gln Ala Glu
65                  70                  75                  80

Asp Glu Ser Asp Tyr Tyr Cys Asn Ser Arg Asp Ser Ser Asp Asn Leu
                85                  90                  95

Val Val Phe Gly Gly Gly Thr Lys Leu Thr Val Leu Gly Gln Pro Lys
            100                 105                 110

Ala Ala Pro Ser Gly Thr Leu Phe Pro Pro Ser Ser
        115                 120

<210> SEQ ID NO 59
<211> LENGTH: 127
<212> TYPE: PRT
<213> ORGANISM: Artificial Sequence
<220> FEATURE:
<223> OTHER INFORMATION: Toso-binding variable heavy chain

<400> SEQUENCE: 59

Ala Gly Thr Ala Ala Ala Val Trp Gly Arg Leu Gly Thr Ala Gly Gly
1               5                   10                  15

Ser Leu Arg Leu Ser Arg Thr Ala Ser Gly Phe Thr Phe Ser Asn Tyr
            20                  25                  30

Ala Met Ser Trp Val Arg Gln Ala Pro Gly Lys Gly Leu Gln Trp Val
        35                  40                  45

Ser Gly Ile Ser Ala Thr Gly Val Ser Thr Tyr Tyr Ala Asp Ser Val
    50                  55                  60

Lys Gly Arg Phe Ala Ile Ser Arg Asp Asn Ser Lys Ser Thr Val Phe
65                  70                  75                  80

Leu Gln Met Asn Ser Leu Arg Ala Glu Asp Thr Ala Ile Tyr Tyr Cys
                85                  90                  95

Ala Lys Tyr Arg Ile Ala Ile Glu Val Ala Tyr Asp Tyr Trp Gly Gln
            100                 105                 110

Gly Thr Leu Val Thr Val Ser Ser Ala Ser Thr Lys Gly Pro Lys
        115                 120                 125

<210> SEQ ID NO 60
<211> LENGTH: 110
<212> TYPE: PRT
<213> ORGANISM: Artificial Sequence
<220> FEATURE:
<223> OTHER INFORMATION: Toso-binding variable light chain

<400> SEQUENCE: 60

```
Leu Arg Leu His Ser Ser Leu Ala Ala Ser Val Gly Asp Arg Val Thr
1               5                   10                  15

Ile Thr Cys Arg Ala Ser Gln Ser Val Ser Thr Tyr Leu Asn Trp Tyr
            20                  25                  30

Gln Gln Leu Pro Gly Lys Ala Pro Lys Leu Leu Ile Ser Gly Ala Ser
        35                  40                  45

Thr Leu Gln Ser Gly Val Pro Ser Arg Phe Ser Gly Ser Gly Ser Gly
    50                  55                  60

Thr Asp Phe Thr Leu Thr Ile Ser Ser Leu Gln Pro Glu Asp Ser Ala
65                  70                  75                  80

Leu Tyr Phe Cys Gln Gln Ser Tyr Ile Tyr Leu Thr Phe Gly Gly Gly
                85                  90                  95

Thr Arg Val Glu Ile Lys Arg Leu Trp Leu His His Leu Ser
            100                 105                 110
```

<210> SEQ ID NO 61
<211> LENGTH: 134
<212> TYPE: PRT
<213> ORGANISM: Artificial Sequence
<220> FEATURE:
<223> OTHER INFORMATION: Toso-binding variable heavy chain

<400> SEQUENCE: 61

```
Gln Val Gln Leu Val Gln Ser Gly Gly Gly Leu Val Gln Pro Gly Gly
1               5                   10                  15

Ser Leu Arg Leu Ser Cys Val Ala Ser Glu Phe Ile Phe Asn Asn Tyr
            20                  25                  30

Asn Met Asn Trp Val Arg Gln Ala Pro Gly Lys Gly Leu Glu Trp Leu
        35                  40                  45

Ser Phe Ile Asp Thr Ser Thr Tyr Thr Thr Tyr Tyr Ala Asp Ser Val
    50                  55                  60

Met Gly Arg Phe Thr Ile Ser Arg Asp Asn Ser Lys Lys Ser Leu Phe
65                  70                  75                  80

Leu Gln Met Asn Thr Leu Thr Asp Glu Asp Thr Ala Val Tyr Phe Cys
                85                  90                  95

Ala Arg Asp Arg Tyr Gly Ser Ser Tyr Trp Gly Gly His Tyr Phe His
            100                 105                 110

Ala Met Asp Val Trp Gly Gln Gly Thr Pro Val Thr Val Ser Ser Ala
        115                 120                 125

Ser Thr Lys Gly Pro Lys
    130
```

<210> SEQ ID NO 62
<211> LENGTH: 116
<212> TYPE: PRT
<213> ORGANISM: Artificial Sequence
<220> FEATURE:
<223> OTHER INFORMATION: Toso-binding variable light chain

<400> SEQUENCE: 62

```
Val Glu Ile Val Leu Thr Gln Ser Pro Pro Thr Leu Ser Val Ser Pro
1               5                   10                  15
```

```
Gly Glu Arg Ala Thr Leu Ser Cys Arg Ala Ser Gln Ser Val Ser Ser
                20                  25                  30

Asn Leu Ala Trp Tyr Gln Gln Lys Pro Gly Gln Ala Pro Arg Leu Leu
                35                  40                  45

Ile Tyr Gly Ala Ser Thr Arg Ala Thr Gly Ile Pro Ala Arg Phe Ser
            50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Ile Thr Phe Gly Gln Gly Thr Arg Leu Glu Ile Lys Arg Thr Val Ala
            100                 105                 110

Ala Pro Ser Val
        115
```

<210> SEQ ID NO 63
<211> LENGTH: 128
<212> TYPE: PRT
<213> ORGANISM: Artificial Sequence
<220> FEATURE:
<223> OTHER INFORMATION: Toso-binding variable heavy chain

<400> SEQUENCE: 63

```
Ala Gly Ala Ala Gly Ala Val Trp Gly Gly Ser Val Gln Pro Gly Gly
1               5                   10                  15

Ser Leu Arg Leu Ser Cys Val Ala Ser Gly Phe Ser Ile Asn Gly Tyr
                20                  25                  30

Asp Leu Ser Trp Val Arg Gln Ala Arg Gly Lys Gly Leu Glu Trp Val
                35                  40                  45

Ser Tyr Ile Ser Pro Thr Gly Thr Thr Thr Arg Tyr Ser Asp Ser Val
            50                  55                  60

Lys Gly Arg Phe Thr Ile Ser Arg Asp Asn Ala Lys Asn Ser Leu His
65                  70                  75                  80

Leu Gln Met Asn Ser Leu Gln Asp Gly Asp Thr Ala Val Tyr Tyr Cys
                85                  90                  95

Ala Arg His Trp Val Trp Gly Gln Gly Thr Leu Val Thr Val Ser Ser
                100                 105                 110

Ala Ser Thr Lys Gly Pro Lys Leu Glu Glu Gly Glu Phe Ser Glu Ala
            115                 120                 125
```

<210> SEQ ID NO 64
<211> LENGTH: 123
<212> TYPE: PRT
<213> ORGANISM: Artificial Sequence
<220> FEATURE:
<223> OTHER INFORMATION: Toso-binding variable light chain

<400> SEQUENCE: 64

```
Arg Arg Tyr Cys Asp Ala Gln Thr Pro Leu Ser Leu Pro Val Thr Leu
1               5                   10                  15

Gly Gln Pro Ala Ser Ile Ser Cys Arg Ser Ser Gln Ser Leu Val Tyr
                20                  25                  30

Ser Asp Gly Asn Thr Tyr Leu Asn Trp Phe Gln Gln Arg Pro Gly Gln
                35                  40                  45

Ser Pro Arg Arg Leu Ile Tyr Lys Val Ser Asn Arg Asp Ser Gly Val
            50                  55                  60

Pro Asp Arg Phe Ser Gly Ser Gly Ser Gly Thr Asp Phe Thr Leu Lys
```

```
                65                  70                  75                  80
Ile Ser Arg Val Glu Ala Glu Asp Val Gly Val Tyr Tyr Cys Met Gln
                    85                  90                  95

Gly Thr His Trp Pro Pro Tyr Thr Phe Gly Gln Gly Thr Arg Leu Glu
            100                 105                 110

Ile Lys Arg Thr Val Ala Ala Pro Ser Val Phe
            115                 120
```

<210> SEQ ID NO 65
<211> LENGTH: 133
<212> TYPE: PRT
<213> ORGANISM: Artificial Sequence
<220> FEATURE:
<223> OTHER INFORMATION: Toso-binding variable heavy chain

<400> SEQUENCE: 65

```
Gln Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe Thr Asn Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Leu Glu Thr Arg Tyr Arg Pro Ser Phe
        50                  55                  60

Gln Gly Gln Val Thr Ile Ser Ala Asp Lys Ser Leu Ser Thr Ala Tyr
65                  70                  75                  80

Leu Gln Trp Ser Ser Leu Glu Ala Ser Asp Thr Ala Thr Tyr Tyr Cys
                85                  90                  95

Ala Arg Ala His Tyr Tyr Asp Thr Thr Ala Tyr Ser Leu Tyr Tyr Tyr
            100                 105                 110

Pro Met Asp Val Trp Gly Gln Gly Pro Arg Ser Ser Ser Pro Gln Pro
        115                 120                 125

Pro Pro Arg Ala Gln
        130
```

<210> SEQ ID NO 66
<211> LENGTH: 127
<212> TYPE: PRT
<213> ORGANISM: Artificial Sequence
<220> FEATURE:
<223> OTHER INFORMATION: Toso-binding variable light chain

<400> SEQUENCE: 66

```
Val Ser Tyr Glu Leu Thr Gln Pro Pro Ser Val Ser Val Ser Pro Gly
1               5                   10                  15

Gln Thr Ala Ser Ile Thr Cys Ser Gly Asp Lys Leu Gly Glu Lys Tyr
                20                  25                  30

Val Cys Trp Tyr Gln Gln Lys Pro Gly Gln Ser Pro Val Ala Val Ile
            35                  40                  45

Tyr Gln Asp Ser Lys Arg Pro Ser Gly Ile Pro Glu Arg Phe Ser Ala
        50                  55                  60

Ser Asn Ser Ala Asn Thr Ala Thr Leu Thr Ile Ser Gly Thr Gln Ala
65                  70                  75                  80

Met Asp Glu Ala Asp Tyr Tyr Cys Gln Ala Trp Asp Ala Trp Asp
                85                  90                  95

Ser Asn Thr Val Phe Phe Gly Gly Gly Thr Arg Leu Thr Val Leu Ser
            100                 105                 110
```

Gln Pro Lys Ala Ala His Ser Val Thr Leu Phe Pro Pro Ser Ser
            115                 120                 125

<210> SEQ ID NO 67
<211> LENGTH: 129
<212> TYPE: PRT
<213> ORGANISM: Artificial Sequence
<220> FEATURE:
<223> OTHER INFORMATION: Toso-binding variable heavy chain

<400> SEQUENCE: 67

Glu Val Gln Leu Leu Glu Ser Gly Gly Gly Leu Val Gln Pro Gly Gly
1               5                   10                  15

Ser Gln Arg Leu Ser Cys Ala Ala Ser Gly Phe Pro Phe Ser Asp Tyr
            20                  25                  30

Asp Met His Trp Val Arg Gln Gly Thr Gly Lys Gly Leu Glu Trp Val
        35                  40                  45

Ser Gly Ile Gly Thr Ala Ser Asp Thr His Tyr Ala Gly Thr Val Lys
50                  55                  60

Gly Arg Phe Thr Ile Ser Arg Glu Asn Ala Arg Asn Ser Leu Tyr Leu
65                  70                  75                  80

Gln Met Asn Ser Leu Arg Ala Gly Asp Thr Ala Val Tyr Tyr Cys Val
            85                  90                  95

Arg Gly Ser Ile Ala Ala His Val Val Gly Ile Asn Met Asp Val Trp
        100                 105                 110

Gly Arg Gly Thr Thr Val Thr Val Ser Ser Ala Ser Thr Lys Gly Pro
    115                 120                 125

Lys

<210> SEQ ID NO 68
<211> LENGTH: 130
<212> TYPE: PRT
<213> ORGANISM: Artificial Sequence
<220> FEATURE:
<223> OTHER INFORMATION: Toso-binding variable light chain

<400> SEQUENCE: 68

Val Asp Ile Glu Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
            85                  90                  95

Tyr Thr Phe Gly Gln Gly Thr Lys Leu Glu Ile Glu Asp Cys Gly Cys
        100                 105                 110

Thr Ile Cys Leu Arg Gly Arg Trp Ile Gln Arg Tyr Gln Ser Asn Cys
    115                 120                 125

Lys Leu
    130

<210> SEQ ID NO 69
<211> LENGTH: 133

```
<212> TYPE: PRT
<213> ORGANISM: Artificial Sequence
<220> FEATURE:
<223> OTHER INFORMATION: Toso-binding variable heavy chain
<220> FEATURE:
<221> NAME/KEY: misc_feature
<222> LOCATION: (84)..(84)
<223> OTHER INFORMATION: Xaa can be any naturally occurring amino acid

<400> SEQUENCE: 69

Ala Gly Glu Leu Val Gln Ser Gly Ala Glu Val Arg Lys Pro Gly Glu
1               5                   10                  15

Ser Leu Gln Ile Ser Cys Thr Ala Ser Gly Tyr Ile Phe Thr Asp Tyr
            20                  25                  30

Trp Ile Gly Trp Val Arg Gln Met Pro Gly Lys Gly Leu Glu Ser Met
        35                  40                  45

Gly Ile Ile Tyr Pro Gly Asp Ser Glu Thr Ser Ser Pro Ser Phe Gln
    50                  55                  60

Gly Gln Val Ile Met Ser Val Asp Lys Tyr Arg Asn Ile Ala Tyr Leu
65                  70                  75                  80

Gln Trp Asn Xaa Leu Lys Ala Ser Asp Thr Ala Thr Tyr Phe Cys Ala
                85                  90                  95

Arg His Gly Arg Gly Tyr Cys Gly Gly Ser Cys Gln Gly Thr Leu
            100                 105                 110

Ile Asp Asn Trp Gly Gln Gly Thr Leu Leu Thr Val Ser Ala Ala Ser
        115                 120                 125

Thr Lys Gly Pro Lys
    130

<210> SEQ ID NO 70
<211> LENGTH: 124
<212> TYPE: PRT
<213> ORGANISM: Artificial Sequence
<220> FEATURE:
<223> OTHER INFORMATION: Toso-binding variable light chain

<400> SEQUENCE: 70

Val Ser Glu Leu Thr Gln Asp Pro Ala Val Ser Val Ala Leu Gly Gln
1               5                   10                  15

Thr Gly Arg Ile Thr Cys Gln Gly Asp Ser Leu Arg Thr Tyr Tyr Ala
            20                  25                  30

Asn Trp Tyr Gln Gln Lys Pro Gly Gln Ala Pro Val Leu Val Ile Tyr
        35                  40                  45

Ala Lys Asn Lys Arg Pro Ser Gly Ile Pro Asp Arg Phe Ser Gly Ser
    50                  55                  60

Ser Ser Gly Asn Thr Ala Tyr Leu Thr Ile Thr Gly Ala Gln Ala Glu
65                  70                  75                  80

Asp Glu Ser Asp Tyr Tyr Cys Asn Ser Arg Asp Ser Ser Asp Asn Leu
                85                  90                  95

Val Val Phe Gly Gly Gly Thr Lys Leu Thr Val Leu Gly Ser Ala Gln
            100                 105                 110

Gly Cys Pro Leu Gly His Ser Val Pro Pro Ser Ser
        115                 120

<210> SEQ ID NO 71
<211> LENGTH: 8
<212> TYPE: PRT
<213> ORGANISM: Artificial Sequence
<220> FEATURE:
<223> OTHER INFORMATION: Toso antibodies heavy chain
```

```
<400> SEQUENCE: 71

Asp Phe Ile Phe Asn Asn Tyr Asn
1               5

<210> SEQ ID NO 72
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 72

Ile Asp Thr Ser Thr Tyr Thr Thr
1               5

<210> SEQ ID NO 73
<211> LENGTH: 20
<212> TYPE: PRT
<213> ORGANISM: Artificial Sequence
<220> FEATURE:
<223> OTHER INFORMATION: Toso antibodies heavy chain

<400> SEQUENCE: 73

Ala Arg Asp Arg Tyr Gly Ser Ser Tyr Trp Gly Gly His Tyr Phe His
1               5                   10                  15

Ala Met Asp Val
            20

<210> SEQ ID NO 74
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 74

Gly Phe Ser Phe Ser Asp Phe Gly
1               5

<210> SEQ ID NO 75
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 75

Val Arg Tyr Asp Gly Ser Lys Glu
1               5

<210> SEQ ID NO 76
<211> LENGTH: 25
<212> TYPE: PRT
<213> ORGANISM: Artificial Sequence
<220> FEATURE:
<223> OTHER INFORMATION: Toso antibodies heavy chain

<400> SEQUENCE: 76

Ala Lys Asp Glu Met Ala Arg Trp Ala Tyr Val Asp Trp Leu Pro His
1               5                   10                  15

Leu His His Ser Tyr Gly Met Asp Val
            20                  25

<210> SEQ ID NO 77
```

```
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 77

Gly Phe Ser Phe Ser Asp Phe Gly
1               5

<210> SEQ ID NO 78
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 78

Val Arg Tyr Asp Gly Ser Lys Glu
1               5

<210> SEQ ID NO 79
<211> LENGTH: 25
<212> TYPE: PRT
<213> ORGANISM: Artificial Sequence
<220> FEATURE:
<223> OTHER INFORMATION: Toso antibodies heavy chain

<400> SEQUENCE: 79

Ala Lys Asp Glu Met Ala Arg Trp Ala Tyr Val Asp Trp Leu Pro His
1               5                   10                  15

Leu His His Ser Tyr Gly Met Asp Val
            20                  25

<210> SEQ ID NO 80
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 80

Gly Phe Thr Phe Ser Asn His Trp
1               5

<210> SEQ ID NO 81
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 81

Ile Lys Arg Asp Ala Thr Ser Thr
1               5

<210> SEQ ID NO 82
<211> LENGTH: 19
<212> TYPE: PRT
<213> ORGANISM: Artificial Sequence
<220> FEATURE:
<223> OTHER INFORMATION: Toso antibodies heavy chain

<400> SEQUENCE: 82

Val Arg Glu Gly Gly Tyr Thr Tyr Gly Gly Val Tyr Tyr Tyr Asn Gly
1               5                   10                  15
```

Met Asp Val

<210> SEQ ID NO 83
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 83

Asp Phe Ile Phe Asn Asn Tyr Asn
1               5

<210> SEQ ID NO 84
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 84

Ile Asp Thr Ser Thr Tyr Thr Thr
1               5

<210> SEQ ID NO 85
<211> LENGTH: 20
<212> TYPE: PRT
<213> ORGANISM: Artificial Sequence
<220> FEATURE:
<223> OTHER INFORMATION: Toso antibodies heavy chain

<400> SEQUENCE: 85

Ala Arg Asp Arg Tyr Gly Ser Ser Tyr Trp Gly Gly His Tyr Phe His
1               5                   10                  15

Ala Met Asp Val
            20

<210> SEQ ID NO 86
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 86

Gly Phe Thr Phe Ser Ser Tyr Asp
1               5

<210> SEQ ID NO 87
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 87

Ile Ser Gly Ser Gly Gly Ser Pro
1               5

<210> SEQ ID NO 88
<211> LENGTH: 14
<212> TYPE: PRT
<213> ORGANISM: Artificial Sequence
<220> FEATURE:
<223> OTHER INFORMATION: Toso antibodies heavy chain

<400> SEQUENCE: 88

```
Ala Lys Pro Tyr Thr Ser Gly Trp Tyr Val Gly Cys Asp Ser
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 89

Gly Phe Thr Phe Ser Asp Cys Ala
1               5

<210> SEQ ID NO 90
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 90

Ile Ser Gly Ser Gly Leu Ser Thr
1               5

<210> SEQ ID NO 91
<211> LENGTH: 18
<212> TYPE: PRT
<213> ORGANISM: Artificial Sequence
<220> FEATURE:
<223> OTHER INFORMATION: Toso antibodies heavy chain

<400> SEQUENCE: 91

Thr Lys Ala Pro Trp Asp Tyr Tyr Gly Ser Gly Asn Thr Asp His Phe
1               5                   10                  15

Asp His

<210> SEQ ID NO 92
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 92

Gly Phe Thr Phe Ser Ser His Ala
1               5

<210> SEQ ID NO 93
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 93

Ile Ser Gly Arg Gly Ser Ser Ile
1               5

<210> SEQ ID NO 94
<211> LENGTH: 9
<212> TYPE: PRT
<213> ORGANISM: Artificial Sequence
<220> FEATURE:
<223> OTHER INFORMATION: Toso antibodies heavy chain
```

```
<400> SEQUENCE: 94

Ala Lys Gly Leu Ala Asp Phe Asp Tyr
1               5

<210> SEQ ID NO 95
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 95

Gly Tyr Asp Phe Ala Asn Phe Trp
1               5

<210> SEQ ID NO 96
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 96

Ile Tyr Pro Asp Asp Ser Asp Val
1               5

<210> SEQ ID NO 97
<211> LENGTH: 13
<212> TYPE: PRT
<213> ORGANISM: Artificial Sequence
<220> FEATURE:
<223> OTHER INFORMATION: Toso antibodies heavy chain

<400> SEQUENCE: 97

Thr Arg Arg Tyr Ser Gly Ala Gln Leu Gly Val Asp Ser
1               5                   10

<210> SEQ ID NO 98
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 98

Gly Tyr Thr Phe Thr Ser Tyr Gly
1               5

<210> SEQ ID NO 99
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 99

Ile Ser Val Tyr Asn Gly Asn Thr
1               5

<210> SEQ ID NO 100
<211> LENGTH: 15
<212> TYPE: PRT
<213> ORGANISM: Artificial Sequence
<220> FEATURE:
<223> OTHER INFORMATION: Toso antibodies heavy chain

<400> SEQUENCE: 100
```

```
Ala Arg Asp Gly Leu Arg Trp Leu Arg Pro Thr Gly Met Asp Val
1               5                   10                  15

<210> SEQ ID NO 101
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 101

Gly Phe Thr Phe Ser Ser Tyr Ala
1               5

<210> SEQ ID NO 102
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 102

Ile Ser Ser Ser Gly Thr Asn Thr
1               5

<210> SEQ ID NO 103
<211> LENGTH: 16
<212> TYPE: PRT
<213> ORGANISM: Artificial Sequence
<220> FEATURE:
<223> OTHER INFORMATION: Toso antibodies heavy chain

<400> SEQUENCE: 103

Val Lys Gly Ser Gly Val Gly Tyr Gln Tyr Tyr Tyr Gly Met Asp Val
1               5                   10                  15

<210> SEQ ID NO 104
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 104

Gly Tyr Ser Leu Ser Asp Tyr Ser
1               5

<210> SEQ ID NO 105
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 105

Ile Asn Pro Lys Thr Gly Gly Thr
1               5

<210> SEQ ID NO 106
<211> LENGTH: 17
<212> TYPE: PRT
<213> ORGANISM: Artificial Sequence
<220> FEATURE:
<223> OTHER INFORMATION: Toso antibodies heavy chain

<400> SEQUENCE: 106
```

```
Ala Arg Pro Gly Phe Cys Thr Ile Asp Asn Cys His Asp Phe Phe Asp
1               5                   10                  15

Ser
```

<210> SEQ ID NO 107
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 107

```
Gly Tyr Thr Phe Ser Asp Tyr Tyr
1               5
```

<210> SEQ ID NO 108
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 108

```
Ile Asn Pro Lys Thr Gly Gly Thr
1               5
```

<210> SEQ ID NO 109
<211> LENGTH: 15
<212> TYPE: PRT
<213> ORGANISM: Artificial Sequence
<220> FEATURE:
<223> OTHER INFORMATION: Toso antibodies heavy chain

<400> SEQUENCE: 109

```
Ala Arg Arg Ser Leu Asn Leu Tyr Tyr Asp Tyr Gly Met Asp Val
1               5                   10                  15
```

<210> SEQ ID NO 110
<211> LENGTH: 10
<212> TYPE: PRT
<213> ORGANISM: Artificial Sequence
<220> FEATURE:
<223> OTHER INFORMATION: Toso antibodies heavy chain

<400> SEQUENCE: 110

```
Gly Ala Leu Val Thr Asn Thr Ala Tyr Tyr
1               5                   10
```

<210> SEQ ID NO 111
<211> LENGTH: 7
<212> TYPE: PRT
<213> ORGANISM: Artificial Sequence
<220> FEATURE:
<223> OTHER INFORMATION: Toso antibodies heavy chain

<400> SEQUENCE: 111

```
Ile Tyr Ala Asn Gly Arg Thr
1               5
```

<210> SEQ ID NO 112
<211> LENGTH: 17
<212> TYPE: PRT
<213> ORGANISM: Artificial Sequence
<220> FEATURE:
<223> OTHER INFORMATION: Toso antibodies heavy chain

<400> SEQUENCE: 112

Val Arg Leu Val Pro Lys Arg Thr Ala Thr Leu His Tyr Tyr Ile Asp
1               5                   10                  15
Val

<210> SEQ ID NO 113
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 113

Gly Asp Thr Ser Ser Ile Tyr Ala
1               5

<210> SEQ ID NO 114
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 114

Ile Asn Pro Ile Pro Arg Ile Thr
1               5

<210> SEQ ID NO 115
<211> LENGTH: 17
<212> TYPE: PRT
<213> ORGANISM: Artificial Sequence
<220> FEATURE:
<223> OTHER INFORMATION: Toso antibodies heavy chain

<400> SEQUENCE: 115

Ala Arg Asp Cys Ser Gly Gly Ser Cys Phe Arg Gln Asp Ala Phe Asp
1               5                   10                  15
Ile

<210> SEQ ID NO 116
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 116

Gly Asp Thr Ser Ser Ile Tyr Ala
1               5

<210> SEQ ID NO 117
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 117

Ile Asn Pro Ile Pro Arg Ile Thr
1               5

<210> SEQ ID NO 118
<211> LENGTH: 17
<212> TYPE: PRT
<213> ORGANISM: Artificial Sequence
<220> FEATURE:

<223> OTHER INFORMATION: Toso antibodies heavy chain

<400> SEQUENCE: 118

Ala Arg Asp Cys Ser Gly Gly Ser Cys Phe Arg Gln Asp Ala Phe Asp
1               5                   10                  15
Ile

<210> SEQ ID NO 119
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 119

Gly Tyr Thr Leu Thr Ser Tyr Asp
1               5

<210> SEQ ID NO 120
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 120

Met Asn Pro Asn Ser Gly Asn Thr
1               5

<210> SEQ ID NO 121
<211> LENGTH: 15
<212> TYPE: PRT
<213> ORGANISM: Artificial Sequence
<220> FEATURE:
<223> OTHER INFORMATION: Toso antibodies heavy chain

<400> SEQUENCE: 121

Ala Arg Gly Arg Ser Ile Ile Asn His Tyr Tyr Gly Leu Asp Val
1               5                   10                  15

<210> SEQ ID NO 122
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 122

Asp Phe Ile Phe Asn Asn Tyr Asn
1               5

<210> SEQ ID NO 123
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 123

Ile Asp Thr Ser Thr Tyr Thr Thr
1               5

<210> SEQ ID NO 124
<211> LENGTH: 20
<212> TYPE: PRT
<213> ORGANISM: Artificial Sequence

```
<220> FEATURE:
<223> OTHER INFORMATION: Toso antibodies heavy chain

<400> SEQUENCE: 124

Ala Arg Asp Arg Tyr Gly Ser Ser Tyr Trp Gly Gly His Tyr Phe His
1               5                   10                  15

Ala Met Asp Val
            20

<210> SEQ ID NO 125
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 125

Gly Phe Ser Phe Ser Ser Tyr Asn
1               5

<210> SEQ ID NO 126
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 126

Ile Ser Ser Gly Ser Ser Tyr Ile
1               5

<210> SEQ ID NO 127
<211> LENGTH: 20
<212> TYPE: PRT
<213> ORGANISM: Artificial Sequence
<220> FEATURE:
<223> OTHER INFORMATION: Toso antibodies heavy chain

<400> SEQUENCE: 127

Thr Arg Asp Arg Tyr Tyr His Asp Ser Asp Glu Tyr Tyr Asp Ala Asp
1               5                   10                  15

Gly Phe Asp Val
            20

<210> SEQ ID NO 128
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 128

Gly Phe Thr Phe Asn Thr Tyr Ala
1               5

<210> SEQ ID NO 129
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 129

Ile Ser Ala Asn Gly Gly Thr Thr
1               5
```

-continued

```
<210> SEQ ID NO 130
<211> LENGTH: 14
<212> TYPE: PRT
<213> ORGANISM: Artificial Sequence
<220> FEATURE:
<223> OTHER INFORMATION: Toso antibodies heavy chain

<400> SEQUENCE: 130

Ala Arg Asp His Leu Trp Phe Gly Glu Tyr Ile Phe Asp Cys
1               5                   10

<210> SEQ ID NO 131
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 131

Gly Phe Thr Phe Thr Asp Ala Trp
1               5

<210> SEQ ID NO 132
<211> LENGTH: 10
<212> TYPE: PRT
<213> ORGANISM: Artificial Sequence
<220> FEATURE:
<223> OTHER INFORMATION: Toso antibodies heavy chain

<400> SEQUENCE: 132

Ile Lys Ser Arg Thr Gly Gly Gly Thr Thr
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Toso antibodies heavy chain

<400> SEQUENCE: 133

Val Trp Ser Gly Arg Asn Trp Phe Gly His
1               5                   10

<210> SEQ ID NO 134
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 134

Gly Tyr Thr Leu Thr Ser Tyr Asp
1               5

<210> SEQ ID NO 135
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 135

Met Asn Pro Asn Ser Gly Asn Thr
1               5
```

```
<210> SEQ ID NO 136
<211> LENGTH: 15
<212> TYPE: PRT
<213> ORGANISM: Artificial Sequence
<220> FEATURE:
<223> OTHER INFORMATION: Toso antibodies heavy chain

<400> SEQUENCE: 136

Ala Arg Gly Arg Ser Ile Ile Asn His Tyr Tyr Gly Leu Asp Val
1               5                   10                  15

<210> SEQ ID NO 137
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 137

Asp Phe Ile Phe Asn Asn Tyr Asn
1               5

<210> SEQ ID NO 138
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 138

Ile Asp Thr Ser Thr Tyr Thr Thr
1               5

<210> SEQ ID NO 139
<211> LENGTH: 19
<212> TYPE: PRT
<213> ORGANISM: Artificial Sequence
<220> FEATURE:
<223> OTHER INFORMATION: Toso antibodies heavy chain

<400> SEQUENCE: 139

Ala Arg Asp Arg Tyr Gly Ser Ser Tyr Trp Gly Ala Thr Ile Ser Thr
1               5                   10                  15

Leu Trp Thr

<210> SEQ ID NO 140
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 140

Gly Tyr Ile Phe Thr Asp Tyr Trp
1               5

<210> SEQ ID NO 141
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 141

Ile Tyr Pro Gly Asp Ser Glu Thr
1               5
```

<210> SEQ ID NO 142
<211> LENGTH: 20
<212> TYPE: PRT
<213> ORGANISM: Artificial Sequence
<220> FEATURE:
<223> OTHER INFORMATION: Toso antibodies heavy chain

<400> SEQUENCE: 142

Ala Arg His Gly Arg Gly Tyr Cys Gly Gly Gly Ser Cys Gln Gly Thr
1               5                   10                  15

Leu Ile Asp Asn
            20

<210> SEQ ID NO 143
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 143

Gly Tyr Ile Phe Thr Asp Tyr Trp
1               5

<210> SEQ ID NO 144
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 144

Ile Tyr Pro Gly Asp Ser Glu Thr
1               5

<210> SEQ ID NO 145
<211> LENGTH: 20
<212> TYPE: PRT
<213> ORGANISM: Artificial Sequence
<220> FEATURE:
<223> OTHER INFORMATION: Toso antibodies heavy chain

<400> SEQUENCE: 145

Ala Arg His Gly Arg Gly Tyr Cys Gly Gly Gly Ser Cys Gln Gly Thr
1               5                   10                  15

Leu Ile Asp Asn
            20

<210> SEQ ID NO 146
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 146

Gly Tyr Thr Leu Thr Ser Tyr Asp
1               5

<210> SEQ ID NO 147
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 147

Met Asn Pro Asn Ser Gly Asn Thr
1               5

<210> SEQ ID NO 148
<211> LENGTH: 15
<212> TYPE: PRT
<213> ORGANISM: Artificial Sequence
<220> FEATURE:
<223> OTHER INFORMATION: Toso antibodies heavy chain

<400> SEQUENCE: 148

Ala Arg Gly Arg Ser Ile Ile Asn His Tyr Tyr Gly Leu Asp Val
1               5                   10                  15

<210> SEQ ID NO 149
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 149

Gly Tyr Ile Phe Thr Asp Tyr Trp
1               5

<210> SEQ ID NO 150
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 150

Ile Tyr Pro Gly Asp Ser Glu Thr
1               5

<210> SEQ ID NO 151
<211> LENGTH: 20
<212> TYPE: PRT
<213> ORGANISM: Artificial Sequence
<220> FEATURE:
<223> OTHER INFORMATION: Toso antibodies heavy chain

<400> SEQUENCE: 151

Ala Arg His Gly Arg Gly Tyr Cys Gly Gly Gly Ser Cys Gln Gly Thr
1               5                   10                  15

Leu Ile Asp Asn
            20

<210> SEQ ID NO 152
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 152

Gly Tyr Ile Phe Thr Asp Tyr Trp
1               5

<210> SEQ ID NO 153
<211> LENGTH: 8
<212> TYPE: PRT
<213> ORGANISM: Artificial Sequence
<220> FEATURE:

-continued

<223> OTHER INFORMATION: Toso antibodies heavy chain

<400> SEQUENCE: 153

Ile Tyr Pro Gly Asp Ser Glu Thr
1               5

<210> SEQ ID NO 154
<211> LENGTH: 20
<212> TYPE: PRT
<213> ORGANISM: Artificial Sequence
<220> FEATURE:
<223> OTHER INFORMATION: Toso antibodies heavy chain

<400> SEQUENCE: 154

Ala Arg His Gly Arg Gly Tyr Cys Gly Gly Gly Ser Cys Gln Gly Thr
1               5                   10                  15

Leu Ile Asp Asn
            20

<210> SEQ ID NO 155
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 155

Gly Tyr Ile Phe Thr Asp Tyr Trp
1               5

<210> SEQ ID NO 156
<211> LENGTH: 8
<212> TYPE: PRT
<213> ORGANISM: Artificial Sequence
<220> FEATURE:
<223> OTHER INFORMATION: Toso antibodies heavy chain

<400> SEQUENCE: 156

Ile Tyr Pro Gly Asp Ser Glu Thr
1               5

<210> SEQ ID NO 157
<211> LENGTH: 20
<212> TYPE: PRT
<213> ORGANISM: Artificial Sequence
<220> FEATURE:
<223> OTHER INFORMATION: Toso antibodies heavy chain

<400> SEQUENCE: 157

Ala Arg His Gly Arg Gly Tyr Cys Gly Gly Gly Ser Cys Gln Gly Thr
1               5                   10                  15

Leu Ile Asp Asn
            20

<210> SEQ ID NO 158
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 158

Gln Ser Val Gly Thr Ser
1               5

```
<210> SEQ ID NO 159
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 159

Asp Ala Ser
1

<210> SEQ ID NO 160
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 160

Gln Gln Arg Ser Asn Gly Pro Pro Ser Trp Thr
1               5                   10

<210> SEQ ID NO 161
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 161

Gln Ser Val Ser Ser Asn
1               5

<210> SEQ ID NO 162
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 162

Gly Ala Ser
1

<210> SEQ ID NO 163
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 163

Gln Gln Tyr Asn Asn Trp Pro Tyr Thr
1               5

<210> SEQ ID NO 164
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 164

Gln Ser Val Ser Ser Asn
1               5

<210> SEQ ID NO 165
```

```
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 165

Gly Ala Ser
1

<210> SEQ ID NO 166
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 166

Gln Gln Tyr Asn Asn Trp Pro Tyr Thr
1               5

<210> SEQ ID NO 167
<211> LENGTH: 12
<212> TYPE: PRT
<213> ORGANISM: Artificial Sequence
<220> FEATURE:
<223> OTHER INFORMATION: Toso antibodies light chain

<400> SEQUENCE: 167

Gln Ser Val Phe Ser Ser Ser Tyr Ser Glu Asp Tyr
1               5                   10

<210> SEQ ID NO 168
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 168

Trp Ala Ser
1

<210> SEQ ID NO 169
<211> LENGTH: 8
<212> TYPE: PRT
<213> ORGANISM: Artificial Sequence
<220> FEATURE:
<223> OTHER INFORMATION: Toso antibodies light chain

<400> SEQUENCE: 169

Gln Tyr Tyr Ile Thr Pro Ile Thr
1               5

<210> SEQ ID NO 170
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 170

Gln Ser Val Gly Thr Ser
1               5

<210> SEQ ID NO 171
<211> LENGTH: 3
```

```
<212> TYPE: PRT
<213> ORGANISM: Artificial Sequence
<220> FEATURE:
<223> OTHER INFORMATION: Toso antibodies light chain

<400> SEQUENCE: 171

Asp Ala Ser
1

<210> SEQ ID NO 172
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 172

Gln Gln Arg Ser Thr Gly Leu Arg Val Gly Arg
1               5                   10

<210> SEQ ID NO 173
<211> LENGTH: 7
<212> TYPE: PRT
<213> ORGANISM: Artificial Sequence
<220> FEATURE:
<223> OTHER INFORMATION: Toso antibodies light chain

<400> SEQUENCE: 173

Gln Ser Val Ser Ser Ser Tyr
1               5

<210> SEQ ID NO 174
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 174

Gly Ala Ser
1

<210> SEQ ID NO 175
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 175

Gln Gln Tyr Gly Ser Ser Pro Trp Thr
1               5

<210> SEQ ID NO 176
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 176

Gln Ser Val Arg Ser Tyr
1               5

<210> SEQ ID NO 177
<211> LENGTH: 3
<212> TYPE: PRT
```

<213> ORGANISM: Artificial Sequence
<220> FEATURE:
<223> OTHER INFORMATION: Toso antibodies light chain

<400> SEQUENCE: 177

Asp Ala Thr
1

<210> SEQ ID NO 178
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 178

Gln Gln Arg Asn Asn Trp Pro Leu Thr
1               5

<210> SEQ ID NO 179
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 179

Gln Ser Val Ser Ser Tyr
1               5

<210> SEQ ID NO 180
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 180

Asp Ala Ser
1

<210> SEQ ID NO 181
<211> LENGTH: 10
<212> TYPE: PRT
<213> ORGANISM: Artificial Sequence
<220> FEATURE:
<223> OTHER INFORMATION: Toso antibodies light chain

<400> SEQUENCE: 181

Gln Gln Arg Ser Asn Trp Pro Pro Tyr Ser
1               5                   10

<210> SEQ ID NO 182
<211> LENGTH: 7
<212> TYPE: PRT
<213> ORGANISM: Artificial Sequence
<220> FEATURE:
<223> OTHER INFORMATION: Toso antibodies light chain

<400> SEQUENCE: 182

Gln Arg Val Asn Thr Gly Tyr
1               5

<210> SEQ ID NO 183
<211> LENGTH: 3
<212> TYPE: PRT
<213> ORGANISM: Artificial Sequence

```
<220> FEATURE:
<223> OTHER INFORMATION: Toso antibodies light chain

<400> SEQUENCE: 183

Gly Ala Ser
1

<210> SEQ ID NO 184
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 184

Gln Gln His Gly Thr Ser Pro Tyr Thr
1               5

<210> SEQ ID NO 185
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 185

Gln Asp Ile Thr His Ser
1               5

<210> SEQ ID NO 186
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 186

Asp Ala Ser
1

<210> SEQ ID NO 187
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 187

Gln Gln Tyr Asp Asn Val Pro Ile Thr
1               5

<210> SEQ ID NO 188
<211> LENGTH: 12
<212> TYPE: PRT
<213> ORGANISM: Artificial Sequence
<220> FEATURE:
<223> OTHER INFORMATION: Toso antibodies light chain

<400> SEQUENCE: 188

Gln Asn Val Leu Tyr Asn Ser Asn Lys Lys Asn Tyr
1               5                   10

<210> SEQ ID NO 189
<211> LENGTH: 3
<212> TYPE: PRT
<213> ORGANISM: Artificial Sequence
<220> FEATURE:
```

<223> OTHER INFORMATION: Toso antibodies light chain

<400> SEQUENCE: 189

Trp Ala Ser
1

<210> SEQ ID NO 190
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 190

Gln Gln Tyr Tyr Gly Thr Pro Leu Thr
1               5

<210> SEQ ID NO 191
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 191

Gln Arg Leu Val Tyr Ser Asp Gly Asn Thr Tyr
1               5                   10

<210> SEQ ID NO 192
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 192

Lys Val Ser
1

<210> SEQ ID NO 193
<211> LENGTH: 10
<212> TYPE: PRT
<213> ORGANISM: Artificial Sequence
<220> FEATURE:
<223> OTHER INFORMATION: Toso antibodies light chain

<400> SEQUENCE: 193

Met Gln Ser Ser Thr Asp Trp Pro Trp Thr
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Toso antibodies light chain

<400> SEQUENCE: 194

Arg Ser Val Leu Tyr Thr Ser Thr Asn Arg Tyr Leu
1               5                   10

<210> SEQ ID NO 195
<211> LENGTH: 3
<212> TYPE: PRT
<213> ORGANISM: Artificial Sequence
<220> FEATURE:
<223> OTHER INFORMATION: Toso antibodies light chain

```
<400> SEQUENCE: 195

Trp Ala Ser
1

<210> SEQ ID NO 196
<211> LENGTH: 10
<212> TYPE: PRT
<213> ORGANISM: Artificial Sequence
<220> FEATURE:
<223> OTHER INFORMATION: Toso antibodies light chain

<400> SEQUENCE: 196

Gln Gln Tyr Tyr Asn Pro Pro Val Tyr Thr
1               5                   10

<210> SEQ ID NO 197
<211> LENGTH: 8
<212> TYPE: PRT
<213> ORGANISM: Artificial Sequence
<220> FEATURE:
<223> OTHER INFORMATION: Toso antibodies light chain

<400> SEQUENCE: 197

Ser Gly His Ser Ser Tyr Ala Ile
1               5

<210> SEQ ID NO 198
<211> LENGTH: 7
<212> TYPE: PRT
<213> ORGANISM: Artificial Sequence
<220> FEATURE:
<223> OTHER INFORMATION: Toso antibodies light chain

<400> SEQUENCE: 198

Leu Asn Ser Asp Gly Ser His
1               5

<210> SEQ ID NO 199
<211> LENGTH: 10
<212> TYPE: PRT
<213> ORGANISM: Artificial Sequence
<220> FEATURE:
<223> OTHER INFORMATION: Toso antibodies light chain

<400> SEQUENCE: 199

Gln Thr Trp Gly Thr Gly Ile His Trp Val
1               5                   10

<210> SEQ ID NO 200
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 200

Gln Ser Val Ser Asp Tyr
1               5

<210> SEQ ID NO 201
<211> LENGTH: 3
<212> TYPE: PRT
<213> ORGANISM: Artificial Sequence
<220> FEATURE:
<223> OTHER INFORMATION: Toso antibodies light chain
```

```
<400> SEQUENCE: 201

Ala Ala Ser
1

<210> SEQ ID NO 202
<211> LENGTH: 9
<212> TYPE: PRT
<213> ORGANISM: Artificial Sequence
<220> FEATURE:
<223> OTHER INFORMATION: Toso antibodies light chain
<220> FEATURE:
<221> NAME/KEY: misc_feature
<222> LOCATION: (1)..(1)
<223> OTHER INFORMATION: Xaa can be any naturally occurring amino acid

<400> SEQUENCE: 202

Xaa Gln Ser Tyr Thr Thr Ala Tyr Thr
1               5

<210> SEQ ID NO 203
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 203

Gln Ser Val Ser Asp Tyr
1               5

<210> SEQ ID NO 204
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 204

Ala Ala Ser
1

<210> SEQ ID NO 205
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 205

Gln Gln Ser Tyr Thr Thr Ala Tyr Thr
1               5

<210> SEQ ID NO 206
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 206

Gln Ser Val Ser Ser Tyr
1               5

<210> SEQ ID NO 207
<211> LENGTH: 3
<212> TYPE: PRT
<213> ORGANISM: Artificial Sequence
```

<220> FEATURE:
<223> OTHER INFORMATION: Toso antibodies light chain

<400> SEQUENCE: 207

Asp Ala Ser
1

<210> SEQ ID NO 208
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 208

Gln Gln Arg Ser Asn Trp Pro Trp Thr
1               5

<210> SEQ ID NO 209
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 209

Gln Ser Val Gly Thr Ser
1               5

<210> SEQ ID NO 210
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 210

Asp Ala Ser
1

<210> SEQ ID NO 211
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 211

Gln Gln Arg Ser Asn Gly Pro Pro Ser Trp Thr
1               5                   10

<210> SEQ ID NO 212
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 212

Gln Ser Ile Ser Ser Tyr
1               5

<210> SEQ ID NO 213
<211> LENGTH: 3
<212> TYPE: PRT
<213> ORGANISM: Artificial Sequence
<220> FEATURE:

<223> OTHER INFORMATION: Toso antibodies light chain

<400> SEQUENCE: 213

Ala Ala Ser
1

<210> SEQ ID NO 214
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 214

Gln Gln Ser Tyr Ser Thr Leu Ser Leu
1               5

<210> SEQ ID NO 215
<211> LENGTH: 12
<212> TYPE: PRT
<213> ORGANISM: Artificial Sequence
<220> FEATURE:
<223> OTHER INFORMATION: Toso antibodies light chain

<400> SEQUENCE: 215

Gln Ser Val Phe Ser Ser Ser Tyr Ser Glu Asp Tyr
1               5                   10

<210> SEQ ID NO 216
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 216

Trp Ala Ser
1

<210> SEQ ID NO 217
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 217

Gln Gln Tyr Tyr Ile Thr Pro Ile Thr
1               5

<210> SEQ ID NO 218
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 218

Gln Ser Leu Val His Ser Asp Gly Asn Thr Tyr
1               5                   10

<210> SEQ ID NO 219
<211> LENGTH: 3
<212> TYPE: PRT
<213> ORGANISM: Artificial Sequence
<220> FEATURE:
<223> OTHER INFORMATION: Toso antibodies light chain

```
<400> SEQUENCE: 219

Lys Ile Ser
1

<210> SEQ ID NO 220
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 220

Cys Lys Leu His Asn Phe Leu Thr Leu
1               5

<210> SEQ ID NO 221
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 221

Gln Ser Ile Ser Asn Tyr
1               5

<210> SEQ ID NO 222
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 222

Ala Ala Ser
1

<210> SEQ ID NO 223
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 223

Gln Gln Ser Tyr Ser Thr Pro Glu Thr
1               5

<210> SEQ ID NO 224
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 224

Gln Ser Ile Ser Ser Tyr
1               5

<210> SEQ ID NO 225
<211> LENGTH: 3
<212> TYPE: PRT
<213> ORGANISM: Artificial Sequence
<220> FEATURE:
<223> OTHER INFORMATION: Toso antibodies light chain
```

```
<400> SEQUENCE: 225

Ala Ala Ser
1

<210> SEQ ID NO 226
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 226

Gln Gln Ser Tyr Ser Thr Pro Cys Thr
1               5

<210> SEQ ID NO 227
<211> LENGTH: 12
<212> TYPE: PRT
<213> ORGANISM: Artificial Sequence
<220> FEATURE:
<223> OTHER INFORMATION: Toso antibodies light chain

<400> SEQUENCE: 227

Gln Ser Val Phe Ser Ser Ser Tyr Ser Glu Asp Tyr
1               5                   10

<210> SEQ ID NO 228
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 228

Trp Ala Ser
1

<210> SEQ ID NO 229
<211> LENGTH: 9
<212> TYPE: PRT
<213> ORGANISM: Artificial Sequence
<220> FEATURE:
<223> OTHER INFORMATION: Toso antibodies light chain

<400> SEQUENCE: 229

Gln Gln Tyr Tyr Ile Thr Pro Ile Thr
1               5

<210> SEQ ID NO 230
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 230

Ser Leu Arg Thr Tyr Tyr
1               5

<210> SEQ ID NO 231
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 231
```

Ala Lys Thr
1

<210> SEQ ID NO 232
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 232

Asn Ser Arg Asp Ser Ser Asp Asn Leu Val Val
1               5                   10

<210> SEQ ID NO 233
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 233

Gln Asp Ile Ser Asn Tyr
1               5

<210> SEQ ID NO 234
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 234

Asp Ala Ser
1

<210> SEQ ID NO 235
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 235

Gln Gln Tyr Asp Asn Leu Pro Pro Gly Ser Pro
1               5                   10

<210> SEQ ID NO 236
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 236

Ser Leu Arg Thr Tyr Tyr
1               5

<210> SEQ ID NO 237
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 237

Ala Lys Asn
1

<210> SEQ ID NO 238
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 238

Asn Ser Arg Asp Ser Ser Asp Asn Leu Val Val
1               5                   10

<210> SEQ ID NO 239
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 239

Ser Leu Arg Thr Tyr Tyr
1               5

<210> SEQ ID NO 240
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 240

Ala Lys Thr
1

<210> SEQ ID NO 241
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 241

Asn Ser Arg Asp Ser Ser Asp Asn Leu Val Val
1               5                   10

<210> SEQ ID NO 242
<211> LENGTH: 6
<212> TYPE: PRT
<213> ORGANISM: Artificial Sequence
<220> FEATURE:
<223> OTHER INFORMATION: Toso antibodies light chain

<400> SEQUENCE: 242

Ser Leu Arg Thr Tyr Tyr
1               5

<210> SEQ ID NO 243
<211> LENGTH: 3
<212> TYPE: PRT
<213> ORGANISM: Artificial Sequence
<220> FEATURE:
<223> OTHER INFORMATION: Toso antibodies light chain

<400> SEQUENCE: 243

Ala Lys Asn

-continued

```
<210> SEQ ID NO 244
<211> LENGTH: 11
<212> TYPE: PRT
<213> ORGANISM: Artificial Sequence
<220> FEATURE:
<223> OTHER INFORMATION: Toso antibodies light chain

<400> SEQUENCE: 244

Asn Ser Arg Asp Ser Ser Asp Asn Leu Val Val
1               5                   10
```